US006693184B1

(12) United States Patent
Howard et al.

(10) Patent No.: US 6,693,184 B1
(45) Date of Patent: Feb. 17, 2004

(54) DNA MOLECULES ENCODING SPLICE VARIANTS OF THE HUMAN MELANOCORTIN 1 RECEPTOR PROTEIN

(75) Inventors: Andrew D. Howard, Park Ridge, NJ (US); Douglas J. MacNeil, Westfield, NJ (US); Leonardus H. T. Van Der Ploeg, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/868,552

(22) Filed: Jun. 18, 2001

Related U.S. Application Data
(60) Provisional application No. 60/113,401, filed on Dec. 23, 1998.

(51) Int. Cl.[7] .......................... C07K 1/00; C07H 21/04; C12N 1/20; C12P 21/06; G01N 33/566
(52) U.S. Cl. .......................... 536/23.5; 435/6; 435/7.21; 435/69.1; 435/252.3; 435/320.1; 436/501; 514/2; 530/300; 530/350
(58) Field of Search .................. 536/23.5; 530/300, 530/350; 514/2; 436/501; 435/6, 7.21, 69.5, 69.1, 252.3, 320.1

(56) References Cited

U.S. PATENT DOCUMENTS 5,532,347 A   7/1996   Cone et al.
5,703,220 A   12/1997  Yamada et al.
5,849,871 A   12/1998  Cone et al.

OTHER PUBLICATIONS

Alexander et al., Proc. Natl. Acad. Sci. 89(3352–3356)1992.*
Bowie et al., 1990, Science 247:1306–1310, especially p. 1306.*
Hillier, L. et al. Database GenBank Accession No. AA778295, Homo sapiens cDNA clone, 1998.
NCI–CGAP, Database GenBank Accession No. AI187892, Homo sapiens cDNA clone, Melanocyte Stimulating Hormone Receptor, 1998.
NCI–CGAP, Database GenBank Accession No. AI123000, Homo sapiens cDNA clone, Melanocyte Stimulating Hormone Receptor, 1998.
Theron, E. et al. "The molecular basis of an avian plumage polymorphism in the wild: A melanocortin–1–receptor point mutation is perfectly associated with the melanic plumage morph of the bananaquit, Coereba flaveola", Current Biology, 2001, vol. 11, pp. 550–557.
Peng, S. et al. "Melanocortin–1 receptor gene variants in four Chinese ethnic populations", Cell Research, 2001, vol. 11, pp. 81–84.
Bastiaens, M. et al. "Melanocortin–1 Receptor Gene Variants Determine the Risk of Nonmelanoma Skin Cancer Independently of Fair Skin and Red Hair", Am. J. Hum. Genet., 2001, vol. 68, pp. 884–894.

(List continued on next page.)

Primary Examiner—Yvonne Eyler
Assistant Examiner—Michael Brannock
(74) Attorney, Agent, or Firm—Alysia A. Finnegan; Joanne Giesser

(57) ABSTRACT

The present invention relates to DNA molecules encoding splice variants of the melanocortin-1 receptor (MC-R1) protein belonging to the rhodopsin sub-family of G-protein coupled receptors, recombinant vectors comprising DNA molecules encoding MC-R1B protein, recombinant host cells which contain a recombinant vector encoding MC-R1B, the human MC-R1B protein encoded by the DNA molecule, and methods of identifying selective agonists and antagonists of MC-R1B proteins disclosed throughout this specification.

18 Claims, 11 Drawing Sheets

OTHER PUBLICATIONS

Box, N. et al. "Melanocortin–1 Receptor Genotype is a Risk Factor for Basal and Squamous Cell Carcinoma", J. of Invest. Dermatol., 2001, vol. 116, pp. 224–229.

Mountjoy, K. et al. "The Cloning of a Family of Genes That Encode the Melanocortin Receptors", Science, 1992, vol. 257, pp. 1248–1251.

Chhajlani, V. et al. "Molecular cloning and expression of the human melanocyte stimulating hormone receptor cDNA", FEBS Letters, 1992, vol. 309, pp. 417–420.

Cone, R. et al. "The Melanocortin Receptors: Agonists, Antagonists, and the Hormonal Control of Pigmentation", Recent Progress in Hormone Research, 1996, vol. 51, pp 287–318.

Jackson, I. "Homologous pigmentation mutations in human, mouse and other model organisms", Human Molecular Genetics, 1997, vol. 6, pp. 1613–1624.

Koppula, S. et al. "Identification of Common Polymorphisms in the Coding Sequence of the Human MSH Receptor (MCIR) With Possible Biological Effects", Human Mutation, 1997, vol. 9, pp. 30–36.

Hillier, L. et al. Database Genbank Accession No. AA431397, Homo sapiens cDNA clone, 1997.

Bonaldo, et al., "Normalization and Subtraction: Two Approaches to Facilitate Gene Discovery", Genome Research, 6:791–806, 1996.

Box, et al., "Characterization of melanocyte stimulating hormone receptor variant alleles in twins with red hair", Human Molecular Genetics, vol. 6, No. 11, pp. 1891–1897, 1997.

Tan, et al., "Molecular analysis of a new splice variant of the human melanocortin–1 receptor", FEBS Letters, 451, pp. 137–141, 1999.

* cited by examiner

```
ATGGCTGTGC AGGGATCCCA GAGAAGACTT CTGGGCTCCC TCAACTCCAC CCCCACAGCC ATCCCCCAGC
TGGGCTGGC TGCCAACCAG ACAGGAGCCC GGTGCCTGGA GGTGTCCATC TCTGACGGGC TCTTCCTCAG
CCTGGGGCTG GTGAGCTTGG TGGAGAACGC GCTGGTGGTG GCCACCATCG CCAAGAACCG GAACGTGCTGG
TCACCATGT ACTGCTTCAT CTGCTGCCTG GCCTTGTCGG ACCTGCTGT GAGCGGGAGC AACGTGCTGG
AGACGGCCGT CATCCTCCTG CTGGAGGCCG GTCACTGGT GGCCCGGGCT GCGGTGCTGC AGCAGCTGGA
CAATGTCATT GACGTGATCA CCTGCAGTC CATGCTGTCC AGCCTCTGCT TCCTGGGCGC CATCGCCGTG
GACCGCTACA TCTCCATCTT CTACGCACTG CGCTACCACA GCATCGTGAC CCTGCCGCGG GCGCGGCAG
CCGTTGCGGC CCTCGGGTG GCCAGTGTCG TCTTCCATCT GCTCTTCATC GCCTACTACG ACCACGTGGC
CGTCCTGCTG TGCCTGTGG TCTTCTTCCT GGCTATGCTG GTGCTCATGG CCGTGCTGTA CGTCCACATG
CTGGCCCCGG CCTGCAGCA CGCCCAGGGC ATCGCCCGGC TCCACAAGAG GCAGCGCCCCG GTCCACCAGG
GCTTTGGCCT TAAAGGCGCT GTCACCCCCA CCATCCTGCT GGGCATTTC TTCCTCTGCT GGGCCCCCTT
CTTCCTCCAT CTCACACTCA TCGTCCTCTG CCCCGAGCAC CCCACGTGCG GCTGCATCTT CAAGAACTTC
AACCTCTTC TCGCCCTCAT CATCTGCAAT GCCTTCATCG ACCCCTCCAT CTACGCCTTC CACAGCCAGG
AGCTCCGCAG GACGCTCAAG GAGGTGCTGA CATGCTCCTG gtgagcgcgg tgcacgcggc tttaagtgtg
ctgggcagag ggaggtggtg atattgtgtg gtctgttcc tgtgtgacc tggcagttc cttacctccc
tggtcccgt ttgtcaaaga ggatggacta aatgatctct gaangtgttg aagcgcggac cctctggt
ccaggaggg gtccctgcaa aactccagc aggactttc accagcagtc gtggaacg gaggagaca
tggggaggtt gtggggcctc aggctccggg caccaggc caacctcagg ctcctaaaga gacattttc
gcccactcct gggacactcc gtctgctcca atgactgagc agcatccac ccacccatc tttgctgcca
gCTCTCAGGA CCGTGCCCTC GTCAGCTGGG ATGTGAAGTC TCTGGGTGA AGTGTGTGCC AAGAGCTACT
CCCACAGCAG CCCCAGGAGA AGGGGCTTTG TGACCAGAAA GCTTCATCCA CAGCCTTGCA GCGGCTCCTG
CAAAAGGAGG TGAAATCCCT GCCTCAGGCC AAGGACCAG GTTTGCAGGA GCCCCCCTAG (SEQ ID NO:21)
```

FIG.3

```
  1 ATG GCT GTG CAG GGA TCC CAG AGA AGA CTT CTG GGC TCC CTC AAC TCC ACC CCC ACA GCC    60
  1  M   A   V   Q   G   S   Q   R   R   L   L   G   S   L   N   S   T   P   T   A    20

61 ATC CCC CAG CTG GGG CTG GCT GCC AAC CAG ACA GGA GCC CGG TGC CTG GAG GTG TCC ATC   120
 21  I   P   Q   L   G   L   A   A   N   Q   T   G   A   R   C   L   E   V   S   I    40
                                                                          I

121 TCT GAC GGG CTC TTC CTG AGC CTG CTT GTG AGC CTG GTG GAG AAC GCG CTG GTG GTG       180
 41  S   D   G   L   F   L   S   L   L   V   S   L   V   E   N   A   L   V   V        60
     S D G L F L S L L                                     E N A L V V
                                                               II

181 GCC ACC ATC GCC AAG AAC CGG AAC CTG CAC TCA CCC ATG TAC TGC TTC ATC TGC TGC CTG   240
 61  A   T   I   A   K   N   R   N   L   H   S   P   M   Y   C   F   I   C   C   L    80
     A T I                                             M Y C F I C C L

241 GCC TTG TCG GAC CTG CTG GTG AGC GGG AGC AAC GTG CTG GAG ACG GCC GTC ATC CTC CTG   300
 81  A   L   S   D   L   L   V   S   G   S   N   V   L   E   T   A   V   I   L   L   100
     A L S D L L                                 N V L E T A V I L L
                                                           III

301 CTG GAG GCC GGT GCA CTG GTG GCT CGG GCG GCT GTG CTG CAG CAG CTG GAC AAT GTC ATT   360
101  L   E   A   G   A   L   V   A   R   A   A   V   L   Q   Q   L   D   N   V   I   120
     L E A G A L                             V L Q Q L D N V I

361 GAC GTG ATC ACC TGC AGC TCC ATG CTG TCC AGC CTC TGC TTC CTG GGC GCC ATC GCC GTG   420
121  D   V   I   T   C   S   S   M   L   S   S   L   C   F   L   G   A   I   A   V   140
     D V I T C S S M L S S L                       G A I A V
               IV

421 GAC CGC TAC ATC TCC ATC TTC TAC GCA CTC CGC TAC CAC AGT ATC GTC ACG CTC TTC ATC   480
141  D   R   Y   I   S   I   F   Y   A   L   R   Y   H   S   I   V   T   L   F   I   160
     D R Y                                     H S I V T L F I
                                                               V

481 GCG CGG CGA GTT GCC GCC CTG TGG GTG GCC AGT GTC TGG GTG TTC TTC CTG GCT ATG CTG   540
161  A   R   R   V   A   A   L   W   V   A   S   V   W   V   F   F   L   A   M   L   180
     A                         V A S V W V F F L A M L

541 GCC TAC TAC GAC CAC GTG GCC GTG CTG CTG TGC CTC GTG GTG TTC TTC CTG GCA ATG CTG   600
181  A   Y   Y   D   H   V   A   V   L   L   C   L   V   V   F   F   L   A   M   L   200
     A Y                       V L L C L V V F F L A M L

601 GTG CTC ATG GCC GTG CTG TAC GTC CAC ATG CTG GCC CGG GCC TGC CAG CAC GCC CAG GGC   660
201  V   L   M   A   V   L   Y   V   H   M   L   A   R   A   C   Q   H   A   Q   G   220
     V L M A V L Y V H M L                 A C Q H A Q G
                                                               VI

661 ATC GCC CGG CTC CAC AAG AGG CAG CGC CCC GTC CAC CAG GGC TTT GGC CTT AAA GGC GCT   720
221  I   A   R   L   H   K   R   Q   R   P   V   H   Q   G   F   G   L   K   G   A   240
     I A R L H K R                                                                                                    
```

FIG.4A

```
721 GTC ACC CCC ACC ATC CTG CTG GGC ATT TTC CTC TGC TGG GGC CCC TTC TTC CTG CAT   780
241  V   T   P   T   I   L   L   G   I   F   L   C   W   G   P   F   F   L   H    260
                             VII
781 CTC ACA CTC ATC CTC GTC TGC CCC GAG CAC CCC ACG TGC GGC TGC ATC TTC AAG AAC TTC   840
261  L   T   L   I   L   V   L   C   P   E   H   P   T   C   G   C   I   F   K   N   E    280

841 AAC CTC TTT CTC GCC ATC ATC TGC AAT GCC ATC ATC GAC CCC CTC ATC TAC GCC TTC   900
281  N   L   F   L   A   I   I   C   N   A   F   I   D   P   L   I   Y   A   F    300

901 CAC AGC CAG GAG CTC CGC AGG ACG CTC AAG GAG GTG CTG ACA TGC TCC TG/gt...ag/CT
301  H   S   Q   E   L   R   R   T   L   K   E   V   L   T   C   S                316
```

MC-R1 form A

```
    TGG TGA   (SEQ ID NO:45)
317  W   *    (SEQ ID NO:46)
```

MC-R1 form B

```
    TGC TCT CAG GAC CGT GCC CTC GTC AGC TGG GAT GTG AAG TCT CTG GGT GGA AGT GTG TGC
317  C   S   Q   D   R   A   L   V   S   W   D   V   K   S   L   G   G   S   V   C

CAA GAG CTA CTC CCA CAG CAG CCC CAG AAG GAG CTT TGT GAC CAG AAA GCT TCA TCC
337  Q   E   L   L   P   Q   Q   P   Q   K   E   L   C   D   Q   K   A   S   S

ACA GCC TTG CAG CGG CTC CAA CGG CTC CTG CAA AAA GAG GTG AAG CCT CAG GCC AAG GGA CCA
357  T   A   L   Q   R   L   Q   R   L   L   Q   K   E   V   K   P   Q   A   K   G   P

GGT TTG CAG GAG CCC CCC TAG                    (SEQ ID NO:21)
377  G   L   Q   E   P   P   *   382              (SEQ ID NO:23)
```

FIG.4B

| | | | | | | | | |
|---|---|---|---|---|---|---|---|---|
| MC-R1MO | 1 | MAVQGSQRRLLGSLNSTPTAIPQLGLAANQTGAR | 34 |
| MC-R1CH | 1 | MAVQGSQRRLLGSLNSTPTAIPQLGLAANQTGAR | 34 |
| MCR1ESTc1 | 1 | MAVQGSQRRLLGSLNSTPTAIPQLGLAANQTGAR | 34 |
| MCR1EST11.6 | 1 | MAVQGSQRRLLGSLNSTPTAIPQLGLAANQTGAR | 34 |
| MCR1ESTc12 | 1 | MAVQGSQRRLLGSLNSTPTAIPQLGLAANQTGAR | 34 |
| MCR1ESTc2 | 1 | MAVQGSQRRLLGSLNSTPTAIPQLGLAANQTGAR | 34 |
| MCR1ESTc4 | 1 | MAVQGSQRRLLGSLNSTPTAIPQLGLAANQTGAR | 34 |
| MCR1ESTc5 | 1 | MAVQGSQRRLLGSLNSTPTAIPQLGLAANQTGAR | 34 |
| MCR1ESTc6 | 1 | MAVQGSQRRLLGSLNSTPTAIPQLGLAANQTGAR | 34 |
| pro-mc1-3 | 1 | MAVQGSQRRLLGSLNSTPTAIPQLGLAANQTGAR | 34 |
| pro-mc1-6 | 1 | MAVQGSQRRLLGSLNSTPTAIPQLGLAANQTGAR | 34 |
| pro-mc1-8 | 1 | MAVQGSQRRLLGSLNSTPTAIPQLGLAANQTGAR | 34 |
| pro-mc1-9 | 1 | MAVQGSQRRLLGSLNSTPTAIPQLGLAANQTGAR | 34 |
| MC-R1MO | 35 | CLEVSISDGLFLSLGLVSLVENALVVATIAKNRN | 68 |
| MC-R1CH | 35 | CLEVSISDGLFLSLGLVSLVENALVVATIAKNRN | 68 |
| MCR1ESTc1 | 35 | CLEVSISDGLFLSLGLVSLVENALVVATIAKNRN | 68 |
| MCR1EST11.6 | 35 | CLEVSISDGLFLSLGLVSLVENALVVATIAKNRN | 68 |
| MCR1ESTc12 | 35 | CLEVSISDGLFLSLGLVSLV[K]NALVVATIAKNRN | 68 |
| MCR1ESTc2 | 35 | CLEVSISDGLFLSLGLVSLVENALVVATIAKNRN | 68 |
| MCR1ESTc4 | 35 | CLEVSISDGLFLSLGLVSLV[K]NALVVATIAKNRN | 68 |
| MCR1ESTc5 | 35 | CLEVSISDGLFLSLGLVSLVENALVVATIAKNRN | 68 |
| MCR1ESTc6 | 35 | CLEVSISDGLFLSLGLVSLVENALVVATIAKNRN | 68 |
| pro-mc1-3 | 35 | CLEVSISDGLFLSLGLVSLVENALVVATIAKNRN | 68 |
| pro-mc1-6 | 35 | CLEVSISDGLFLSLGLVSLVENALVVATIAKNRN | 68 |
| pro-mc1-8 | 35 | CLEVSISDGLFLSLGLVSLVENALVVATIAKNRN | 68 |
| pro-mc1-9 | 35 | CLEVSISDGLFLSLGLVSLVENALVVATIAKNRN | 68 |

FIG. 5A

|          |     |                                              |     |
|----------|-----|----------------------------------------------|-----|
| MC-R1MO  | 69  | LHS PMYCFI CCLA LSDLL VSG T N VLETAVILLLE    | 102 |
| MC-R1CH  | 69  | LHS PMYCFI CCLA LSDLL VSGSN VLETAVILLLE      | 102 |
| MC-R1ESTc1 | 69 | LHS PMYCFI CCLA LSDLL VSGSN VLETAVILLLE     | 102 |
| MC-R1EST11.6 | 69 | LHS PMYCFI CCLA LSDLL VSGSN VLETAVILLLE   | 102 |
| MC-R1ESTc12 | 69 | LHS PMYCFI CCLA LSDLL VSGSN VLETAVILLLE    | 102 |
| MC-R1ESTc2 | 69 | LHS PMYCFI CCLA LSDLL VSGSN VLETAVILLLE     | 102 |
| MC-R1ESTc4 | 69 | LHS PMYCFI CCLA LSDLL VSGSN VLETAVILLLE     | 102 |
| MC-R1ESTc5 | 69 | LHS PMYCFI CCLA LSDLL VSGSN VLETAVILLLE     | 102 |
| MC-R1ESTc6 | 69 | LHS PMYCFI CCLA LSDLL VSGSN VLETAVILLLE     | 102 |
| pro-mc1-3 | 69 | LHS PMYCFI CCLA LSDLL VSGSN VLETAVILLLE      | 102 |
| pro-mc1-6 | 69 | LHS PMYCFI CCLA LSDLL VSGSN VLETAVILLLE      | 102 |
| pro-mc1-8 | 69 | LHS PMYCFI CCLA LSDLL VSGSN VLETAVILLLE      | 102 |
| pro-mc1-9 | 69 | LHS PMYCFI CCLA LSDLL VSGSN VLETAVILLLE      | 102 |

|          |     |                                              |     |
|----------|-----|----------------------------------------------|-----|
| MC-R1MO  | 103 | AGAL VARAAV LQQ LDN VIDV ITCSSML SSLCFLG     | 136 |
| MC-R1CH  | 103 | AGAL VARAAV LQQ LDN VIDV ITCSSML SSLCFLG     | 136 |
| MC-R1ESTc1 | 103 | AGAL VARAAV LQQ LDN VIDV ITCSSML SSLCFLG   | 136 |
| MC-R1EST11.6 | 103 | AGAL VARAAV LQQ LDN VIDV ITCSSML SSLCFLG | 136 |
| MC-R1ESTc12 | 103 | AGAL VARAAV LQQ LDN VIDV ITCSSML SSLCFLG  | 136 |
| MC-R1ESTc2 | 103 | AGAL VARAAV LQQ LDN VIDV ITCSSML SSLCFLG   | 136 |
| MC-R1ESTc4 | 103 | AGAL VARAAV LQQ LDN VIDV ITCSSM F SSLCFLG  | 136 |
| MC-R1ESTc5 | 103 | AGAL VARAAV LQQ LDN VIDV ITCSSML SSLCFLG   | 136 |
| MC-R1ESTc6 | 103 | AGAL VARA Q V LQQ LDN VIDV ITCSSML SSLCFLG | 136 |
| pro-mc1-3 | 103 | AGAL VARAAV LQQ LDN VIDV ITCSSML SSLCFLG    | 136 |
| pro-mc1-6 | 103 | AGAL VARAAV LQQ LDN VIDV ITCSSML SSLCFLG    | 136 |
| pro-mc1-8 | 103 | AGAL VARAAV LQQ LDN VIDV ITCSSML SSLCFLG    | 136 |
| pro-mc1-9 | 103 | AGAL VARAAV LQQ LDN VIDV ITCSSML SSLCFLG    | 136 |

| | | | | | | | | |
|---|---|---|---|---|---|---|---|---|
| MC-R1MO | 137 | A I A V D R Y I S I F Y A L R Y H S I V T L P R A P A V A A I W V | 170 |
| MC-R1CH | 137 | A I A V D R Y I S I F Y A L R Y H S I V T L P R A R Q A V A A I W V | 170 |
| MCR1ESTc1 | 137 | A I A V D R Y I S I F Y A L R Y H S I V T L P R A R Q A V A A I W V | 170 |
| MCR1EST11.6 | 137 | A I A V D R Y I S I F Y A L R Y H S I V T L P R A R Q A V A A I W V | 170 |
| MCR1ESTc12 | 137 | A I A V D R Y I S I F Y A L R Y H S I V T L P R A R Q A V A A I W V | 170 |
| MCR1ESTc2 | 137 | A I A V D R Y I S I F Y A L R Y H S I V T L P R A R Q A V A A I W V | 170 |
| MCR1ESTc4 | 137 | A I A V D R Y I S I F Y A L R Y H S I V T L P R A R R A V A A I W V | 170 |
| MCR1ESTc5 | 137 | A I A V D R Y I S I F Y A L R Y H S I V T L P R A R Q A V A A I W V | 170 |
| MCR1ESTc6 | 137 | A I A V D R Y I S I F Y A L R Y H S I V T L P R A R Q A V A A I W V | 170 |
| pro-mc1-3 | 137 | A I A A D R Y I S I F Y A L C Y H S I V T L P R A R R A V A A I W V | 170 |
| pro-mc1-6 | 137 | A I A V D R Y I S I F Y A L R Y H S I V T L P R A R Q A V A A I W V | 170 |
| pro-mc1-8 | 137 | A I A V D R Y I S I F Y A L R Y H S I V T L P R A R R A V A A L W V | 170 |
| pro-mc1-9 | 137 | A V A V D R Y I S I F Y A L R Y H S I V T L P R A R Q A V A A I W V | 170 |

| | | | | | | | | |
|---|---|---|---|---|---|---|---|---|
| MC-R1MO | 171 | A S V V F S T L F I A Y Y D H V A V L L C L V F F L A M L V L M A | 204 |
| MC-R1CH | 171 | A S V V F S T L F I A Y Y D H V A V L L C L V F F L A M L V L M A | 204 |
| MCR1ESTc1 | 171 | A S V V F S T L F I A Y Y D H V A V L L C L V F F L A M L V L M A | 204 |
| MCR1EST11.6 | 171 | A S V V F S T L F I A Y Y D H V A V L L C L V F F L A M L V L M A | 204 |
| MCR1ESTc12 | 171 | A S V V F S T L F I A Y Y D H V A V L L C L V F F L A M L V L M A | 204 |
| MCR1ESTc2 | 171 | A S V V F S T L F I A Y Y D H V A V L L C L V F F L A M L V L M A | 204 |
| MCR1ESTc4 | 171 | A S V V F S T L F I A Y Y D H A A V L L C L V F F L A M L V L M A | 204 |
| MCR1ESTc5 | 171 | A S V V F S T L F I A Y Y D H V A V L L C L V F F L A M L V L M A | 204 |
| MCR1ESTc6 | 171 | A S V V F S T L F I A Y Y D H V A V L L C L V F F L A M L V L M A | 204 |
| pro-mc1-3 | 171 | A S V V F S T L F I A Y Y D H V A V L L C L V F F L A M L V L M A | 204 |
| pro-mc1-6 | 171 | A S V V F S T L F I A Y Y D H V A V L L C L V F F L A M L V L M A | 204 |
| pro-mc1-8 | 171 | A S V V F S T L F I A Y Y D H V A V L L C L V F F L A M L V L M A | 204 |
| pro-mc1-9 | 171 | A S V V F S T L F I A Y Y D H V A V L L C L V F F L A M L V L M A | 204 |

| | | | | | | | | | | | | | | | | | |
|---|---|---|---|---|---|---|---|---|---|---|---|---|---|---|---|---|---|
| MC-R1MO | 205 | V | L | Y | V | H | M | L | A | R | A | C | Q | H | A | Q | G | I | A | R | L | H | K | R | Q | R | P | V | H | Q | G | F | G | L | K | 238 |
| MC-R1CH | 205 | V | L | Y | V | H | M | L | A | R | A | C | Q | H | A | Q | G | I | A | R | L | H | K | R | Q | R | P | V | H | Q | G | F | G | L | K | 238 |
| MC-R1ESTc1 | 205 | V | L | Y | V | H | M | L | A | R | A | C | Q | H | A | Q | G | I | A | R | L | H | K | R | Q | R | P | V | H | Q | G | F | G | L | K | 238 |
| MC-R1ESTc11.6 | 205 | V | L | Y | V | H | M | L | A | R | A | C | Q | H | A | Q | G | I | A | R | L | H | K | R | Q | R | P | V | H | Q | G | F | G | L | K | 238 |
| MC-R1ESTc12 | 205 | V | L | Y | V | H | M | L | A | R | A | C | Q | H | A | Q | G | I | A | R | L | H | K | R | Q | R | P | V | H | Q | G | F | G | L | K | 238 |
| MC-R1ESTc2 | 205 | V | L | Y | V | H | M | L | A | R | A | C | Q | H | A | Q | G | I | A | R | L | H | K | R | Q | R | P | V | H | Q | C | F | G | L | K | 238 |
| MC-R1ESTc4 | 205 | V | L | Y | V | H | M | L | A | R | A | C | Q | H | A | Q | G | I | A | R | L | H | K | R | Q | R | P | V | H | Q | G | F | G | L | K | 238 |
| MC-R1ESTc5 | 205 | V | L | Y | V | H | M | L | A | R | A | C | Q | H | A | Q | G | I | A | R | L | H | K | R | Q | R | P | V | H | Q | G | F | G | L | K | 238 |
| MC-R1ESTc6 | 205 | V | L | Y | V | H | M | L | A | R | A | C | Q | H | A | Q | G | I | A | R | L | H | K | R | Q | R | P | V | H | Q | G | F | G | L | K | 238 |
| pro-mc1-3 | 205 | V | L | Y | V | H | M | L | A | R | A | C | Q | H | A | Q | G | I | A | R | L | H | K | R | Q | R | P | V | H | Q | G | F | G | L | K | 238 |
| pro-mc1-6 | 205 | V | L | Y | V | H | M | L | A | R | A | C | Q | H | A | Q | G | I | A | R | L | H | K | R | Q | R | P | V | H | Q | G | F | G | L | K | 238 |
| pro-mc1-8 | 205 | V | L | Y | V | H | M | L | A | R | A | C | Q | H | A | Q | G | I | A | R | L | H | K | R | Q | R | P | V | H | Q | G | F | G | L | K | 238 |
| pro-mc1-9 | 205 | V | L | Y | V | H | M | L | A | R | A | C | Q | H | A | Q | G | I | A | R | L | H | K | R | Q | R | P | V | H | Q | G | F | G | L | K | 238 |

| | | | | | | | | | | | | | | | | | |
|---|---|---|---|---|---|---|---|---|---|---|---|---|---|---|---|---|---|
| MC-R1MO | 239 | G | A | V | T | L | T | I | L | L | G | I | F | F | L | C | W | G | P | F | F | L | H | L | T | L | I | V | L | C | P | E | H | P | T | 272 |
| MC-R1CH | 239 | G | A | V | T | L | T | I | L | L | G | I | F | F | L | C | W | G | P | F | F | L | H | L | T | L | I | V | L | C | P | E | H | P | T | 272 |
| MC-R1ESTc1 | 239 | G | A | V | T | L | T | I | L | L | G | I | F | F | L | C | W | G | P | F | F | L | H | L | T | L | I | V | L | C | P | E | H | P | T | 272 |
| MC-R1ESTc11.6 | 239 | G | A | V | T | L | T | I | L | L | G | I | F | F | L | C | W | G | P | F | F | L | H | L | T | L | I | V | L | C | P | E | H | P | T | 272 |
| MC-R1ESTc12 | 239 | G | A | V | T | L | T | I | L | L | G | I | F | F | L | C | W | G | P | F | F | L | H | L | T | L | I | V | L | C | P | E | H | P | T | 272 |
| MC-R1ESTc2 | 239 | G | A | V | T | L | T | I | L | L | G | I | F | F | L | C | W | G | P | F | F | L | H | L | T | L | I | V | L | C | P | E | H | P | T | 272 |
| MC-R1ESTc4 | 239 | G | A | V | T | L | T | I | L | L | G | I | F | F | L | C | W | G | P | F | F | L | H | L | T | L | I | V | L | C | P | E | H | P | T | 272 |
| MC-R1ESTc5 | 239 | G | A | V | T | L | T | I | L | L | G | I | F | F | L | C | W | G | P | F | F | L | H | L | T | L | I | V | L | C | P | E | H | P | T | 272 |
| MC-R1ESTc6 | 239 | G | A | V | T | L | T | I | L | L | G | I | F | F | L | C | W | G | P | F | F | L | H | L | T | L | I | V | L | C | P | E | H | P | T | 272 |
| pro-mc1-3 | 239 | G | A | V | T | L | T | I | L | L | G | I | F | F | L | C | W | G | P | F | F | L | H | L | T | L | I | V | L | C | P | E | H | P | T | 272 |
| pro-mc1-6 | 239 | G | A | V | T | L | T | I | L | L | G | I | F | F | L | C | W | G | P | F | F | L | H | L | T | L | I | V | L | C | P | E | H | P | T | 272 |
| pro-mc1-8 | 239 | G | A | V | T | [P] | T | I | L | L | G | I | F | F | L | C | W | G | P | F | F | L | H | L | T | L | I | V | L | C | P | E | H | P | T | 272 |
| pro-mc1-9 | 239 | G | A | V | T | L | T | I | L | L | G | I | F | F | L | C | W | G | P | F | F | L | H | L | T | L | I | V | L | C | P | E | H | P | T | 272 |

FIG. 5D

| | | | | | | | | | | |
|---|---|---|---|---|---|---|---|---|---|---|
| MC-R1MO | 273 | CGC IFKNFNLFLAL ICNA I IDPL IYAFHSQELR | 306 |
| MC-R1CH | 273 | CGC IFKNFNLFLAL ICNA I IDPL IYAFHSQELR | 306 |
| MC-R1ESTc1 | 273 | CGC IFKNFNLFLAL ICNA I IDPL IYAFHSQELR | 306 |
| MC-R1EST11.6 | 273 | CGC IFKNFNLFLAL ICNA I IDPL IYAFHSQELR | 306 |
| MC-R1ESTc12 | 273 | CGC IFKNFNLFLAL ICNA I IDPL IYAFHSQELR | 306 |
| MC-R1ESTc2 | 273 | CGC IFKNFNLFLAL ICNA I IDPL IYAFHSQELR | 306 |
| MC-R1ESTc4 | 273 | CGC IFKNFNLFLAL ICNA I IDPL IYAFHSQELR | 306 |
| MC-R1ESTc5 | 273 | CGC IFKNFNLFLAL ICNA I IDPL IYAFHSQELR | 306 |
| MC-R1ESTc6 | 273 | CGC IFKNFNLFLAL ICNA I IDPL IYAFHSQELR | 306 |
| pro-mc1-3 | 273 | CGC IFKNFNLFLAL ICNA I IDPL IYAFHSQELR | 306 |
| pro-mc1-6 | 273 | CGC IFKNFNLFLAL ICNA [F] IDPL IYAFHSQELR | 306 |
| pro-mc1-8 | 273 | CGC IFKNFNLFLA[P]L ICNA I IDPL IYAFHSQELR | 306 |
| pro-mc1-9 | 273 | CGC IFKNFNLFLAL ICNA I IDPL IYAFHSQELR | 306 |

| | | | |
|---|---|---|---|
| MC-R1MO | 307 | RTLKEVLTCS · · · · · · · · · · · · · · · · · · · · · · · W SEQ ID NO:43 | 317 |
| MC-R1CH | 307 | RTLKEVLTCS · · · · · · · · · · · · · · · · · · · · · · · W SEQ ID NO:44 | 317 |
| MC-R1ESTc1 | 307 | RTLKEVLTCSCSQDRALVSWDVKSLGGSVCQELL | 340 |
| MC-R1EST11.6 | 307 | RTLKEVLTCSCSQDRALVSWDVKSLGGSVCQELL | 340 |
| MC-R1ESTc12 | 307 | RTLKEVLTCSCSQDRALVSWDVKSLGGSVCQELL | 340 |
| MC-R1ESTc2 | 307 | RTLKEVLTCSCSQDRALVSWDVKSLGGSVCQELL | 340 |
| MC-R1ESTc4 | 307 | RTLKEVLTCSCSQDRALVSWDVKSLGGSVC[R]ELL | 340 |
| MC-R1ESTc5 | 307 | RTLKEVLTCSCSQDRALVSWDVKSLGGSVCQELL | 340 |
| MC-R1ESTc6 | 307 | RTLKEVLTCSCSQDRALVSWDVKSLGGSVCQELL | 340 |
| pro-mc1-3 | 307 | RTLKEVLTCSCSQDRALVSWDVKSLGGSVCQELL | 340 |
| pro-mc1-6 | 307 | RTLKEVLTCS[R]SQDRALVSWDVKSLGGSVCQELL | 340 |
| pro-mc1-8 | 307 | RTLKEVLTCSCSQDRALVSWDVKSLGGSVCQELL | 340 |
| pro-mc1-9 | 307 | RTLKEVLTCSCSQDRALVSWDVKSLGGSVCQELL | 340 |

FIG.5E

| | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| MCR1ESTc1 | 341 | P | Q | Q | P | Q | E | K | G | P | C | D | Q | K | A | S | S | T | A | L | Q | R | L | L | L | Q | K | E | V | K | S | L | P | Q | A | K | 374 |
| MCR1EST11.6 | 341 | P | Q | Q | P | Q | E | K | G | L | C | D | Q | K | A | S | S | T | A | L | Q | R | L | L | L | Q | K | E | V | K | S | L | P | Q | A | K | 374 |
| MCR1ESTc12 | 341 | P | Q | Q | P | Q | E | K | G | L | C | D | Q | K | A | S | S | T | A | L | Q | R | L | L | L | Q | K | E | V | K | S | L | P | Q | A | K | 374 |
| MCR1ESTc2 | 341 | P | Q | Q | P | Q | E | K | G | L | C | D | Q | K | A | S | S | T | A | L | Q | R | L | L | L | Q | K | E | V | K | S | L | P | Q | A | K | 374 |
| MCR1ESTc4 | 341 | P | Q | Q | P | Q | E | K | G | L | C | D | Q | K | A | S | S | T | A | L | Q | R | L | L | L | Q | K | G | V | K | S | L | P | Q | A | K | 374 |
| MCR1ESTc5 | 341 | P | Q | Q | P | Q | E | K | G | L | C | D | Q | K | A | S | S | T | A | L | Q | R | L | L | L | Q | K | E | V | K | S | L | P | Q | A | K | 374 |
| MCR1ESTc6 | 341 | P | Q | Q | P | Q | E | K | G | L | C | D | Q | K | A | S | S | T | A | L | Q | R | L | L | L | Q | K | E | V | K | S | L | P | Q | A | K | 374 |
| pro-mc1-3 | 341 | P | Q | Q | P | Q | E | K | G | L | C | D | Q | K | A | S | S | T | A | L | Q | R | L | L | L | Q | K | E | V | K | S | L | P | Q | A | K | 374 |
| pro-mc1-6 | 341 | P | Q | Q | P | Q | E | K | G | L | C | D | Q | K | A | S | S | T | A | L | Q | R | L | L | L | Q | K | E | V | K | S | L | P | Q | A | K | 374 |
| pro-mc1-8 | 341 | P | Q | Q | P | Q | E | K | G | L | C | D | Q | K | A | S | S | T | A | L | Q | R | L | L | L | Q | K | E | V | K | S | L | P | Q | A | K | 374 |
| pro-mc1-9 | 341 | P | Q | Q | P | Q | E | K | G | L | C | D | Q | K | A | S | S | T | A | L | Q | R | L | L | L | Q | K | E | V | K | S | L | P | Q | A | K | 374 |

| | | | | | | | | | |
|---|---|---|---|---|---|---|---|---|---|
| MCR1ESTc1 | 375 | G | P | G | L | Q | E | P | P | 382 | SEQ ID NO:2 |
| MCR1EST11.6 | 375 | G | P | G | L | Q | E | P | P | 382 | SEQ ID NO:4 |
| MCR1ESTc12 | 375 | G | P | G | L | Q | E | P | P | 382 | SEQ ID NO:6 |
| MCR1ESTc2 | 375 | G | P | G | L | Q | E | P | P | 382 | SEQ ID NO:8 |
| MCR1ESTc4 | 375 | G | P | G | L | Q | E | P | P | 382 | SEQ ID NO:10 |
| MCR1ESTc5 | 375 | G | P | G | L | Q | E | P | P | 382 | SEQ ID NO:12 |
| MCR1ESTc6 | 375 | G | P | G | L | Q | E | P | P | 382 | SEQ ID NO:14 |
| pro-mc1-3 | 375 | G | P | G | L | Q | E | P | P | 382 | SEQ ID NO:17 |
| pro-mc1-6 | 375 | G | P | G | L | Q | E | P | P | 382 | SEQ ID NO:20 |
| pro-mc1-8 | 375 | G | P | G | L | Q | E | P | P | 382 | SEQ ID NO:23 |
| pro-mc1-9 | 375 | G | P | G | L | Q | E | P | P | 382 | SEQ ID NO:26 |

FIG.5F

DNA MOLECULES ENCODING SPLICE VARIANTS OF THE HUMAN MELANOCORTIN 1 RECEPTOR PROTEIN

CROSS-REFERENCE TO RELATED APPLICATIONS

The present application claims priority to U.S. Ser. No. 60/113,401, filed Dec. 23, 1998, which is hereby incorporated by reference.

FIELD OF THE INVENTION

The present invention relates to DNA molecules encoding splice variants of the melanocortin-1 receptor (MC-R1) protein belonging to the rhodopsin sub-family of G-protein coupled receptors, recombinant vectors comprising DNA molecules encoding MC-R1 splice variant proteins, recombinant host cells which contain a recombinant vector encoding MC-R1 splice variants, the human MC-R1 proteins encoded by the DNA molecule, and methods of identifying selective agonists and antagonists of MC-R1 splice variant proteins disclosed throughout this specification.

BACKGROUND OF THE INVENTION

Melanocortin receptors belong to the rhodopsin sub-family of G-protein coupled receptors (GPCR's). Five different subtypes are known. These melanocortin receptors bind and are activated by peptides such as α-, β-, or γ-melanocyte stimulating hormones (α-, β-, γ-MSH) derived from the pro-opiomelanocortin (POMC) gene. A wide range of physiological functions are believed to be mediated by melanocortin peptides and their receptors.

U.S. Pat. No. 5,532,347, issued on Jul. 2, 1996, to Cone and Mountjoy discloses and claims human and mouse DNA molecules which encode MC-R1 (also known in the art as α-MSH-R). The expressed human protein contains 317 amino acids.

U.S. Pat. No. 5,849,871, issued on Dec. 15, 1998, to Cone and Mountjoy discloses and claims human and mouse MC-R1. As noted in the previous paragraph, the expressed human protein contains 317 amino acid residues.

Mountjoy, et al. (1992, *Science* 257: 1248–1251) describe DNA molecules and the concomitant protein for human MC-R1 and human MC-R2.

Chhajlani, et al. (1992, *FEBS Letters* 309: 417–420) also disclose a human DNA molecule comprising an open reading frame which encodes human MC-R1.

Cone et al. (1996, *Recent Progress in Hormone Research* 51: 287–318) reviews the state of known mammalian melanocortin receptors, from MC-R1 through MC-R5.

Jackson (1997, *Human Molecular Genetics* 6: 1613–24) and Koppula, et al. (1997, *Human Mutation* 9:30–36) review the occurrence and potential significance of polymorphisms within the coding sequence of the human MC-R1 form A.

It is desirable to correlate in vivo data with in vitro biochemical activity of compounds.

It is also desirable to select compounds which activate one or more human melanocortin receptor proteins in vitro.

It is further desirable to discover new drugs which effect pathophysiological processes by modulating melanocortin receptor activity, followed by human clinical trials.

The present invention addresses and meets these needs by disclosing isolated nucleic acid molecules which express splice variants of human MC-R1, recombinant vectors which house these nucleic acid molecules, recombinant host cells which expresses these alternative forms of human MC-R1 and/or biologically active equivalents, and pharmacological properties of these human MC-R1 proteins.

SUMMARY OF THE INVENTION

The present invention relates to a series of isolated nucleic acid molecules (polynucleotides) which encode novel variants of the human melanocortin-1 receptor protein, referred to herein as MC-R1B proteins. The nucleic acid molecules of the present invention are substantially free from other nucleic acids. These isolated nucleic acid molecules encode a MC-R1 protein which contains an intracellular domain with an additional 65 amino acid residues in comparison to the previously disclosed human MC-R1, referred to herein also as MC-R1A. Therefore, the present invention relates to isolated nucleic acid molecules (polynucleotides) which encode a mRNA which expresses a novel human MC-R1 protein, these DNA molecules including but by no means being limited to DNA molecules comprising the nucleotide sequence disclosed herein as SEQ ID NO:1, SEQ ID NO:3, SEQ ID NO:5, SEQ ID NO:7, SEQ ID NO:9, SEQ ID NO:11, SEQ ID NO:13, SEQ ID NO:16, SEQ ID NO:19, SEQ ID NO:22, and SEQ ID NO:25.

The present invention also relates to isolated nucleic acid molecules which represent human genomic clones which comprise at least a single intron within the open reading frame which encodes novel variants of human MC-R1B protein. Therefore, the present invention relates to isolated nucleic acid molecules (polynucleotides) which encode a RNA molecule which is spliced to generate a mRNA molecule which encodes a novel human MC-R1 protein variant, these DNA molecules including but by no means being limited to DNA molecules comprising the nucleotide sequence disclosed herein as SEQ ID NO:15, SEQ ID NO:18, SEQ ID NO:21, and SEQ ID NO:24. To this end, the present invention also relates to the respective mRNA molecule generated from each of the DNA molecules depicted as SEQ ID NO:15, SEQ ID NO:18, SEQ ID NO:21, and SEQ ID NO:24.

The isolated nucleic acid molecules of the present invention comprise a 3' extension in the open reading frame which encodes a 65 amino acid COOH-terminal extension to known MC-R1. Therefore, the present invention relates to isolated nucleic acid molecules, both DNA and RNA molecules, that encode for a splice variant of known MC-R1 which encodes for this 65 amino acid COOH-terminal extension. The totality of nucleic acid molecules of the present invention, including genomic DNA, cDNA, RNA and mRNA, will be referred to herein as "MC-R1 splice variants", which will identify a disclosed nucleic acid molecule which encodes an protein with melanocortin 1 receptor activity in combination with this additional 3' exon which encodes a 65 amino acid COOH-terminal extension. These isolated nucleic acid molecules include but are by no means limited to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:16, SEQ ID NO:18; SEQ ID NO:19, SEQ ID NO:21, SEQ ID NO:22, SEQ ID NO:24, and SEQ ID NO:25.

The present invention also relates to biologically active fragments or mutants of MC-R1 splice variants which encodes mRNA expressing a novel human MC-R1. Any such biologically active fragment and/or mutant of the MC-R1 splice variants disclosed herein will encode either a protein or protein fragment which at least substantially mimics the pharmacological properties of a wild-type MC-R1 protein and comprises at least a portion of the COOH terminal amino acid extension disclosed as SEQ ID NO:27. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for agonists and/or antagonists for MC-R1B function.

A preferred aspect of this portion of the present invention is set forth as SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:16, SEQ ID NO:18; SEQ ID NO:19, SEQ ID NO:21, SEQ ID NO:22, SEQ ID NO:24, and SEQ ID NO:25, human nucleic acid molecules which comprise the complete open reading frame for the MC-R1B proteins of the present invention.

The isolated nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA).

The present invention also relates to recombinant vectors and recombinant hosts, both prokaryotic and eukaryotic, which contain the substantially purified nucleic acid molecules disclosed throughout this specification, including but not limited to the isolated nucleic acid molecules as set forth in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:16, SEQ ID NO:18; SEQ ID NO:19, SEQ ID NO:21, SEQ ID NO:22, SEQ ID NO:24, and SEQ ID NO:25.

The present invention also relates to subcellular membrane fractions of the recombinant host cells (both prokaryotic and eukaryotic as well as both stably and transiently transformed cells) which contain the proteins encoded by the nucleic acids of the present invention. These subcellular membrane fractions will comprise either wild-type or mutant forms of the human melanocortin-1 receptor proteins which comprise the COOH-terminal extension at levels substantially above endogenous levels and hence will be useful in various assays described throughout this specification.

The present invention also relates to a substantially purified form of the COOH-terminal variants of human melanocortin-1 receptor protein, which comprises the amino acid sequences as disclosed in FIGS. 5A–5F and as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:17, SEQ ID NO:20, SEQ ID NO:23, and SEQ ID NO:26. These MC-R1 proteins comprise a 65 amino acid extension at the COOH-terminus when compared to known human MC-R1 and are referred to throughout this specification as MC-R1B proteins or MC-R1 splice variant proteins.

The present invention also relates to biologically active fragments and/or mutants of the human MC-R1B proteins disclosed throughout this specification, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for agonists and/or antagonists for MC-R1B function.

The present invention also relates to isolated nucleic acid molecules which are fusion constructions expressing fusion proteins useful in assays to identify compounds which modulate wild-type vertebrate MC-R1B activity. A preferred aspect of this portion of the invention includes, but is not limited to, glutathione S-transferase (GST)-MC-R1B fusion constructs which include, but are not limited to, either the intracellular domain of human MC-1RB as an in-frame fusion at the carboxy terminus of the GST gene, or the extracellular and transmembrane ligand binding domain of MC-R1B fused to the amino terminus of GST, or the extracellular and transmembrane domain of MC-R1B fused to an immunoglobulin gene by methods known to one of ordinary skill in the art. Soluble recombinant GST-MC-R1B fusion proteins may be expressed in various expression systems, including *Spodoptera frugiperda* (Sf21) insect cells (Invitrogen) using a baculovirus expression vector (pAcG2T, Pharmingen).

Therefore, the present invention relates to methods of expressing the human MC-R1B proteins disclosed herein and biological equivalents, assays employing these gene products, recombinant host cells which comprise DNA constructs which express these receptor proteins, and compounds identified through these assays which act as agonists or antagonists of MC-R1B activity.

The present invention also relates to polyclonal and monoclonal antibodies raised in response to either the human form of a MC-R1B protein, or a biologically active fragment thereof.

It is an object of the present invention to provide an isolated nucleic acid molecule which encodes a novel form of human MC-R1B, or human MC-R1B fragments, mutants or derivatives of the human MC-R1B proteins as set forth in FIGS. 5A–5F and SEQ ID NO:2, SEQ ID NO:4, SEQ ID NO:6, SEQ ID NO:8, SEQ ID NO:10, SEQ ID NO:12, SEQ ID NO:14, SEQ ID NO:17, SEQ ID NO:20, SEQ ID NO:23, and SEQ ID NO:26. Any such polynucleotide includes but is not necessarily limited to nucleotide substitutions, deletions, additions, aminoterminal truncations and carboxy-terminal truncations such that these mutations encode mRNA which express a protein or protein fragment of diagnostic, therapeutic or prophylactic use and would be useful for screening for agonists and/or antagonists for vertebrate MC-R1B function.

It is a further object of the present invention to provide the human MC-R1B proteins or protein fragments encoded by the nucleic acid molecules referred to in the preceding paragraph.

It is a further object of the present invention to provide recombinant vectors and recombinant host cells which comprise a nucleic acid sequence encoding these human MC-R1B proteins or biological equivalents thereof.

It is an object of the present invention to provide a substantially purified form of any of the human MC-R1B proteins, including but not limited to the proteins as set forth in FIGS. 5A–5F and SEQ ID NO:2, SEQ ID NO:4, SEQ ID NO:6, SEQ ID NO:8, SEQ ID NO:10, SEQ ID NO:12, SEQ ID NO:14, SEQ ID NO:17, SEQ ID NO:20, SEQ ID NO:23, and SEQ ID NO:26.

It is an object of the present invention to provide for biologically active fragments and/or mutants of the human MC-R1B proteins disclosed herein, including but not necessarily limited to amino acid substitutions, deletions, additions, amino terminal truncations and carboxy-terminal truncations such that these mutations provide for proteins or protein fragments of diagnostic, therapeutic or prophylactic use.

It is also an object of the present invention to provide for MC-R1B-based assays to select for modulators of this receptor protein. These assays are preferably cell based assays whereby a DNA molecule encoding MC-R1B is transfected or transformed into a host cell tested wherein this recombinant host cell is allowed to grow for a time sufficient to express MC-R1B prior to use in various assays described herein.

Alternatively, an assay utilizing substantially purified membrane fractions from such a transfected host cell with a DNA vector encoding the MC-R1B protein, such that binding of test compounds in relation to a known MC-R1B ligand may be tested. To this end, it is a further object to provide for membrane preparations from host cells transfected or transformed with a DNA molecule encoding MC-R1B for use in assays to select for modulators of MC-R1B activity.

It is also an object of the present invention to provide for MC-R1B-based in-frame fussion constructions, methods of expressing these fusion constructs, biological equivalents disclosed herein, related assays, recombinant cells expressing these constructs, and agonistic and/or antagonistic compounds identified through the use of the nucleic acid encoding vertebrate MC-R1B protein as well as the expressed protein.

As used herein, "MC-R1 splice variants" and/or "MC-R1B splice variants", refers to a nucleic acid molecule which encodes a protein with melanocortin-1 receptor activity which comprises a 3' exon segment which encodes a 65 amino acid COOH-terminal extension identified in SEQ ID NO:27. Such nucleic acid molecules include but are not limited to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:16, SEQ ID NO:18; SEQ ID NO:19, SEQ ID NO:21, SEQ ID NO:22, SEQ ID NO:24, and SEQ ID NO:25.

As used herein, "MC-R1B" and/or "MC-R1 splice variant proteins" refers to the proteins translated from the MC-R1 splice variant nucleic acid molecules disclosed herein. These human MC-R1B proteins include but are not limited to SEQ ID NO:2, SEQ ID NO:4, SEQ ID NO:6, SEQ ID NO:8, SEQ ID NO:10, SEQ ID NO:12, SEQ ID NO:14, SEQ ID NO:17, SEQ ID NO:20, SEQ ID NO:23, and SEQ ID NO:26.

As used herein, "GPCR" refers to—G-protein coupled receptor—.

The terms "isolated" and "purified" are used interchangeably to denote a nucleic acid, protein, membrane fraction and such which is substantially free from other like components.

Whenever used herein, the term "mammalian host" will refer to any mammal, including a human being.

BRIEF DESCRIPTION OF THE FIGURES

FIG. 3 shows the DNA sequence of the genomic clone, mc1-8 (SEQ ID NO:21). Large cap letters represent exon regions while small cap nucleotides represent the single intron of the MC-R1 gene.

FIGS. 4A–4B show the DNA and deduced amino acid sequence of the mc1-8 genomic clone as a form A (SEQ ID Nos: 45 and 46) and form B (SEQ ID NOs: 21 and 23), illustrating spliced forms MCR1-A and MC-R1B.

FIGS. 5A–5F show the clustal alignment of amino acid sequences of various human MC-R1A and MCR1B clones.

DETAILED DESCRIPTION OF THE INVENTION

Figure 1:
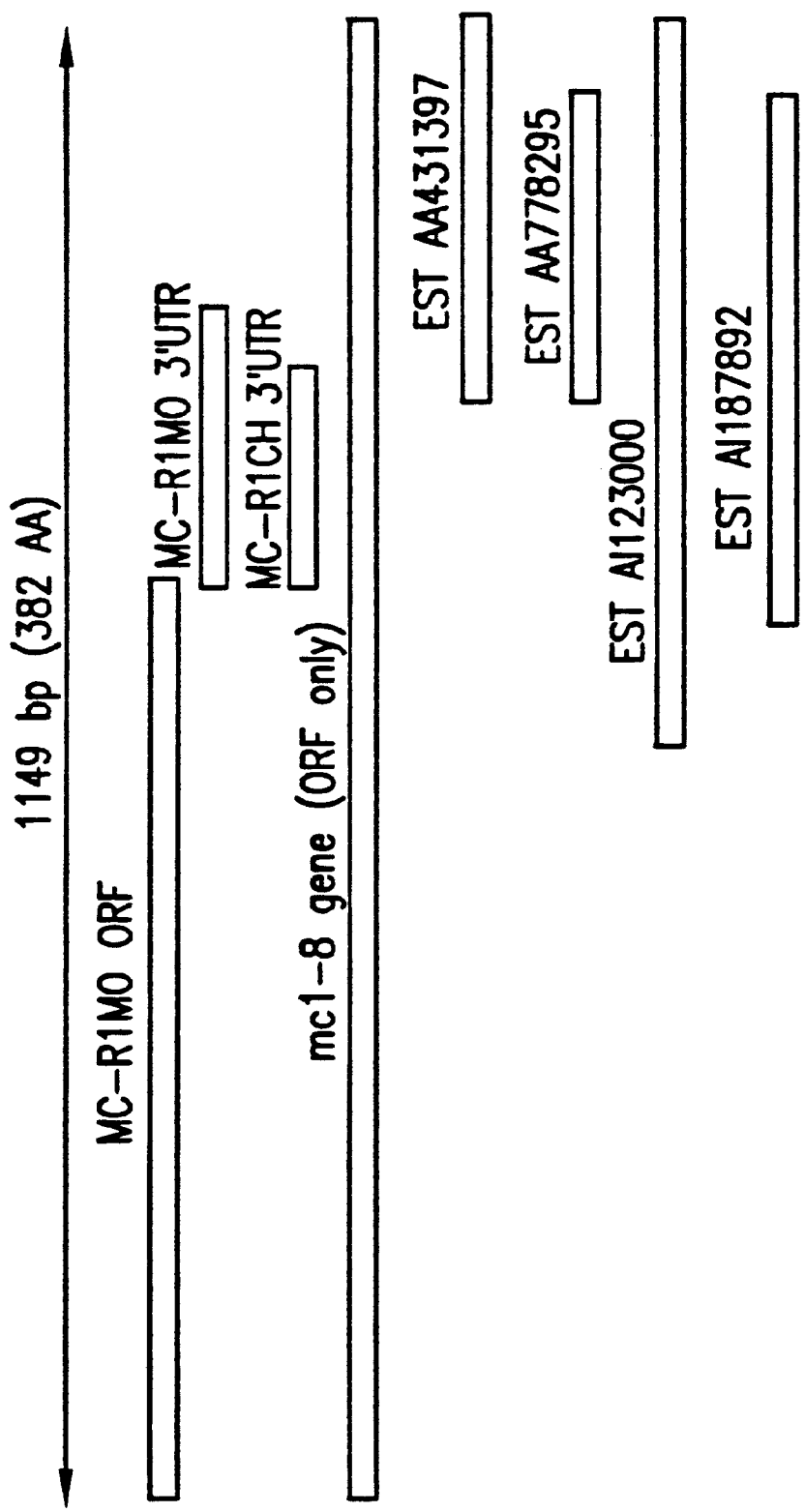
FIG. 1 shows a schematic representation of the human MC-R1 sequences. MC-R1MO (GenBank Accession #X65634) and MC-R1CH (GenBank Accession #X67594) are also referred to herein as MC-R1A genes. The nucleotide sequence of mc1-8 (including a single intron) is disclosed in SEQ ID NO:21. The depicted ESTs are described in Example Section 1.

The present invention relates to isolated nucleic acid molecules (polynucleotide) which encode human melanocortin-1 receptor variant proteins referred to as MC-R1B proteins. The nucleic acid molecules of the present invention are substantially free from other nucleic acids. For most cloning purposes, DNA is a preferred nucleic acid.

The present invention relates to a series of isolated nucleic acid molecules (polynucleotide) which encodes mRNA which express novel splice variants of MC-R1, referred to as MC-R1B proteins. These DNA molecules comprise nucleotide sequences disclosed below.

```
1. MC-R1ESTc11
ATGGCTGTGC AGGGATCCCA GAGAAGACTT CTGGGCTCCC TCAACTCCAC CCCCACAGCC

ATCCCCCAGC TGGGGCTGGC TGCCAACCAG ACAGGAGCCC GGTGCCTGGA GGTGTCCATC

TCTGACGGGC TCTTCCTCAG CCTGGGGCTG GTGAGCTTGG TGGAGAACGC GCTGGTGGTG

GCCACCATCG CCAAGAACCG GAACCTGCAC TCACCCATGT ACTGCTTCAT CTGCTGCCTG

GCCTTGTCGG ACCTGCTGGT GAGCGGGAGC AACGTGCTGG AGACGGCCGT CATCCTCCTG

CTGGAGGCCG GTGCACTGGT GGCCCGGGCT GCGGTGCTGC AGCAGCTGGA CAATGTCATT

GACGTGATCA CCTGCAGCTC CATGCTGTCC AGCCTCTGCT TCCTGGGCGC CATCGCCGTG

GACCGCTACA TCTCCATCTT CTACGCACTG CGTTACCACA GCATCGTGAC CCTGCCGCGG
```

-continued

```
GCGCGGCAAG CCGTTGCGGC CATCTGGGTG GCCAGTGTCG TCTTCAGCAC GCTCTTCATC

GCCTACTACG ACCACGTGGC CGTCCTGCTG TGCCTCGTGG TCTTCTTCCT GGCTATGCTG

GTGCTCATGG CCGTGCTGTA CGTCCACATG CTGGCCCGGG CCTGCCAGCA CGCCCAGGGC

ATCGCCCGGC TCCACAAGAG GCAGCGCCCG GTCCACCAGG GCTTTGGCCT TAAAGGCGCT

GTCACCCTCA CCATCCTGCT GGGCATTTTC TTCCTCTGCT GGGCCCCTT CTTCCTGCAT

CTCACACTCA TCGTCCTCTG CCCCGAGCAC CCCACGTGCG GCTGCATCTT CAAGAACTTC

AACCTCTTTC TCGCCCTCAT CATCTGCAAT GCCATCATCG ACCCCCTCAT CTACGCCTTC

CACAGCCAGG AGCTCCGCAG GACGCTCAAG GAGGTGCTGA CATGCTCCTG CTCTCAGGAC

CGTGCCCTCG TCAGCTGGGA TGTGAAGTCT CTGGGTGGAA GTGTGTGCCA AGAGCTACTC

CCACAGCAGC CCCAGGAGAA GGGGCCTTGT GACCAGAAAG CTTCATCCAC AGCCTTGCAG

CGGCTCCTGC AAAAGGAGGT GAAATCCCTG CCTCAGGCCA AGGGACCAGG TTTGCAGGAG

CCCCCCTAG (SEQ ID NO:1);
```

2. MC-R1ESTC11.6
```
ATGGCTGTGC AGGGATCCCA GAGAAGACTT CTGGGCTCCC TCAACTCCAC CCCCACAGCC

ATCCCCCAGC TGGGGCTGGC TGCCAACCAG ACAGGAGCCC GGTGCCTGGA GGTGTCCATC

TCTGACGGGC TCTTCCTCAG CCTGGGGCTG GTGAGCTTGG TGGAGAACGC GCTGGTGGTG

GCCACCATCG CCAAGAACCG GAACCTGCAC TCACCCATGT ACTGCTTCAT CTGCTGCCTG

GCCTTGTCGG ACCTGCTGGT GAGCGGGAGC AACGTGCTGG AGACGGCCGT CATCCTCCTG

CTGGAGGCCG GTGCACTGGT GGCCCGGGCT GCGGTGCTGC AGCAGCTGGA CAATGTCATT

GACGTGATCA CCTGCAGCTC CATGCTGTCC AGCCTCTGCT TCCTGGGCGC CATCGCCGTG

GACCGCTACA TCTCCATCTT CTACGCACTG CGTTACCACA GCATCGTGAC CCTGCCGCGG

GCGCGGCAAG CCGTTGCGGC CATCTGGGTG GCCAGTGTCG TCTTCAGCAC GCTCTTCATC

GCCTACTACG ACCACGTGGC CGTCCTGCTG TGCCTCGTGG TCTTCTTCCT GGCTATGCTG

GTGCTCATGG CCGTGCTGTA CGTCCACATG CTGGCCCGGG CCTGCCAGCA CGCCCAGGGC

ATCGCCCGGC TCCACAAGAG GCAGCGCCCG GTCCACCAGG GCTTTGGCCT TAAAGGCGCT

GTCACCCTCA CCATCCTGCT GGGCATTTTC TTCCTCTGCT GGGCCCCTT CTTCCTGCAT

CTCACACTCA TCGTCCTCTG CCCCGAGCAC CCCACGTGCG GCTGCATCTT CAAGAACTTC

AACCTCTTTC TCGCCCTCAT CATCTGCAAT GCCATCATCG ACCCCCTCAT CTACGCCTTC

CACAGCCAGG AGCTCCGCAG GACGCTCAAG GAGGTGCTGA CATGCTCCTG CTCTCAGGAC

CGTGCCCTCG TCAGCTGGGA TGTGAAGTCT CTGGGTGGAA GTGTGTGCCA AGAGCTACTC

CCACAGCAGC CCCAGGAGAA GGGGCTTTGT GACCAGAAAG CTTCATCCAC AGCCTTGCAG

CGGCTCCTGC AAAAGGAGGT GAAATCCCTG CCTCAGGCCA AGGGACCAGG TTTGCAGGAG

CCCCCCTAG (SEQ ID NO:3);
```

3. MC-R1ESTc12
```
ATGGCTGTGC AGGGATCCCA GAGAAGACTT CTGGGCTCCC TCAACTCCAC CCCCACAGCC

ATCCCCCAGC TGGGGCTGGC TGCCAACCAG ACAGGAGCCC GGTGCCTGGA GGTGTCCATC

TCTGACGGGC TCTTCCTCAG CCTGGGGCTG GTGAGCTTGG TGAAGAACGC GCTGGTGGTG

GCCACCATCG CCAAGAACCG GAACCTGCAC TCACCCATGT ACTGCTTCAT CTGCTGCCTG

GCCTTGTCGG ACCTGCTGGT GAGCGGGAGC AACGTGCTGG AGACGGCCGT CATCCTCCTG

CTGGAGGCCG GTGCACTGGT GGCCCGGGCT GCGGTGCTGC AGCAGCTGGA CAATGTCATT

GACGTGATCA CCTGCAGCTC CATGCTGTCC AGCCTCTGCT TCCTGGGCGC CATCGCCGTG
```

-continued

```
GACCGCTACA TCTCCATCTT CTACGCACTG CGCTACCACA GCATCGTGAC CCTGCCGCGG
GCGCGGCAAG CCGTTGCGGC CATCTGGGTG GCCAGTGTCG TCTTCAGCAC GCTCTTCATC
GCCTACTACG ACCACGTGGC CGTCCTGCTG TGCCTCGTGG TCTTCTTCCT GGCTATGCTG
GTGCTCATGG CCGTGCTGTA CGTCCACATG CTGGCCCGGG CCTGCCAGCA CGCCCAGGGC
ATCGCCCGGC TCCACAAGAG GCAGCGCCCG GTCCACCAGG GCTTTGGCCT TAAAGGCGCT
GTCACCCTCA CCATCCTGCT GGGCATTTTC TTCCTCTGCT GGGGCCCCTT CTTCCTGCAT
CTCACACTCA TCGTCCTCTG CCCCGAGCAC CCCACGTGCG GCTGCATCTT CAAGAACTTC
AACCTCTTTC TCGCCCTCAT CATCTGCAAT GCCATCATCG ACCCCCTCAT CTACGCCTTC
CACAGCCAGG AGCTCCGCAG GACGCTCAAG GAGGTGCTGA CATGCTCCTG CTCTCAGGAC
CGTGCCCTCG TCAGCTGGGA TGTGAAGTCT CTGGGTGGAA GTGTGTGCCA AGAGCTACTC
CCACAGCAGC CCCAGGAGAA GGGGCTTTGT GACCAGAAAG CTTCATCCAC AGCCTTGCAG
CGGCTCCTGC AAAAGGAGGT GAAATCCCTG CCTCAGGCCA AGGGACCAGG TTTGCAGGAG
CCCCCCTAG (SEQ ID NO:5);
```

4. MC-R1ESTc2
```
ATGGCTGTGC AGGGATCCCA GAGAAGACTT CTGGGCTCCC TCAACTCCAC CCCCACAGCC
ATCCCCCAGC TGGGGCTGGC TGCCAACCAG ACAGGAGCCC GGTGCCTGGA GGTGTCCATC
TCTGACGGGC TCTTCCTCAG CCTGGGGCTG GTGAGCTTGG TGGAGAACGC GCTGGTGGTG
GCCACCATCG CCAAGAACCG GAACCTGCAC TCACCCATGT ACTGCTTCAT CTGCTGCCTG
GCCTTGTCGG ACCTGCTGGT GAGCGGGAGC AACGTGCTGG AGACGGCCGT CATCCTCCTG
CTGGAGGCCG GTGCACTGGT GGCCCGGGCT GCGGTGCTGC AGCAGCTGGA CAATGTCATT
GACGTGATCA CCTGCAGCTT CATGCTGTCC AGCCTCTGCT TCCTGGGCGC CATCGCCGTG
GACCGCTACA TCTCCATCTT CTACGCACTG TGCTACCACA GCATCGTGAC CCTGCCGCGG
GCGCGGCGAG CCGTTGCGGC CATCTGGGTG GCCAGTGTCG TCTTCAGCAC GCTCTTCATC
GCCTACTACG ACCACGTGGC CGTCCTGCTG TGCCTCGTGG TCTTCTTCCT GGCTATGCTG
GTGCTCATGG CCGTGCTGTA CGTCCACATG CTGGCCCGGG CCTGCCAGCA CGCCCAGGGC
ATCGCCCGGC TCCACAAGAG GCAGCGCCCG GTCCACCAGG GCTTTGGCCT TAAAGGCGCT
GTCACCCTCA CCATCCTGCT GGGCATTTTC TTCCTCTGCT GGGGCCCCTT CTTCCTGCAT
CTCACACTCA TCGTCCTCTG CCCCGAGCAC CCCACGTGCG GCTGCATCTT CAAGAACTTC
AACCTCTTTC TCGCCCTCAT CATCTGCAAT GCCATCATCG ACCCCCTCAT CTACGCCTTC
CACAGCCAGG AGCTCCGCAG GACGCTCAAG GAGGTGCTGA CATGCTCCTG CTCTCAGGAC
CGTGCCCTCG TCAGCTGGGA TGTGAAGTCT CTGGGTGGAA GTGTGTGCCA AGAGCTACTC
CCACAGCAGC CCCAGGAGAA GGGGCTTTGT GACCAGAAAG CTTCATCCAC AGCCTTGCAG
CGGCTCCTGC AAAAGGAGGT GAAATCCCTG CCTCAGGCCA AGGGACCAGG TTTGCAGGAG
CCCCCCTAG (SEQ ID NO:7);
```

5. MC R1ESTc4
```
ATGGCTGTGC AGGGATCCCA GAGAAGACTT CTGGGCTCCC TCAACTCCAC CCCCACAGCC
ATCCCCCAGC TGGGGCTGGC TGCCAACCAG ACAGGAGCCC GGTGCCTGGA GGTGTCCATC
TCTGACGGGC TCTTCCTCAG CCTGGGGCTG GTGAGCTTGG TGGAGAACGC GCTGGTGGTG
GCCACCATCG CCAACAACCG GAACCTGCAC TCACCCATGT ACTGCTTCAT CTGCTGCCTG
GCCTTGTCGG ACCTGCTGGT GAGCGGGAGC AACGTGCTGG AGACGGCCGT CATCCTCCTG
CTGGAGGCCG GTGCACTGGT GGCCCGGGCT GCGGTGCTGC AGCAGCTGGA CAATGTCATT
```

```
GACGTGATCA CCTGCAGCTC CATGCTGTCC AGCCTCTGCT TCCTGGGCGC CATCGCCGTG

GACCGCTACA TCTCCATCTT CTACGCACTG CGCTACCACA GCATCGTGAC CCTGCCGCGG

GCGCGGCGAG CCGTTGCGGC CATCTGGGTG GCCAGTGTCG TCTTCAGCAC GCTCTTCATC

GCCTACTACG ACCACGCGGC CGTCCTGCTG TGCCTCGTGG TCTTCTTCCT GGCTATGCTG

GTGCTCATGG CCGTGCTGTA CGTCCACATG CTGGCCCGGG CCTGCCAGCA CGCCCAGGGC

ATCGCCCGGC TCCACAAGAG GCAGCGCCCG GTCCACCAGG GCTTTGGCCT TAAAGGCGCT

GTCACCCTCA CCATCCTGCT GGGCATTTTC TTCCTCTGCT GGGGCCCCTT CTTCCTGCAT

CTCACACTCA TCGTCCTCTG CCCCGAGCAC CCCACGTGCG GCTGCATCTT CAAGAACTTC

AACCTCTTTC TCGCCCTCAT CATCTGCAAT GCCATCATCG ACCCCCTCAT CTACGCCTTC

CACAGCCAGG AGCTCCGCAG GACGCTCAAG GAGGTGCTGA CATGCTCCTG CTCTCAGGAC

CGTGCCCTCG TCAGCTGGGA TGTGAAGTCT CTGGGTGGAA GTGTGTGCCA AGAGCGACTC

CCACAGCAGC CCCAGGAGAA GGGGCTTTGT GACCAGAAAG CTTCATCCAC AGCCTTGCAG

CGGCTCCTGC AAAAGGGGGT GAAATCCCTG CCTCAGGCCA AGGGACCAGG TTTGCAGGAG

CCCCCCTAG (SEQ ID NO:9);

6. MC-R1ESTc5
ATGGCTGTGC AGGGATCCCA GAGAAGACTT CTGGGCTCCC TCAACTCCAC CCCCACAGCC

ATCCCCCAGC TGGGGCTGGC TGCCAACCAG ACAGGAGCCC GGTGCCTGGA GGTGTCCATC

TCTGACGGGC TCTTCCTCAG CCTGGGGCTG GTGAGCTTGG TGAAGAACGC GCTGGTGGTG

GCCACCATCG CCAAGAACCG GAACCTGCAC TCACCCATGT ACTGCTTCAT CTGCTGCCTG

GCCTTGTCGG ACCTGCTGGT GAGCGGGAGC AACGTGCTGG AGACGGCCGT CATCCTCCTG

CTGGAGGCCG GTGCACTGGT GGCCCGGGCT GCGGTGCTGC AGCAGCTGGA CAATGTCATT

GACGTGATCA CCTGCAGCTC CATGCTGTCC AGCCTCTGCT TCCTGGGCGC CATCGCCGTG

GACCGCTACA TCTCCATCTT CTACGCACTG CGCTACCACA GCATCGTGAC CCTGCCGCGG

GCGCGGCAAG CCGTTGCGGC CATCTGGGTG GCCAGTGTCG TCTTCAGCAC GCTCTTCATC

GCCTACTACG ACCACGTGGC CGTCCTGCTG TGCCTCGTGG TCTTCTTCCT GGCTATGCTG

GTGCTCATGG CCGTGCTGTA CGTCCACATG CTGGCCCGGG CCTGCCAGCA CGCCCAGGGC

ATCGCCCGGC TCCACAAGAG GCAGCGCCCG GTCCACCAGG GCTTTGGCCT TAAAGGCGCT

GTCACCCTCA CCATCCTGCT GGGCATTTTC TTCCTCTGCT GGGGCCCCTT CTTCCTGCAT

CTCACACTCA TCGTCCTCTG CCCCGAGCAC CCCACGTGCG GCTGCATCTT CAAGAACTTC

AACCTCTTTC TCGCCCTCAT CATCTGCAAT GCCATCATCG ACCCCCTCAT CTACGCCTTC

CACAGCCAGG AGCTCCGCAG GACGCTCAAG GAGGTGCTGA CATGCTCCTG CTCTCAGGAC

CGTGCCCTCG TCAGCTGGGA TGTGAAGTCT CTGGGTGGAA GTGTGTGCCA AGAGCTACTC

CCACAGCAGC CCCAGGAGAA GGGGCTTTGT GACCAGAAAG CTTCATCCAC AGCCTTGCAG

CGGCTCCTGC AAAAGGAGGT GAAATCCCTG CCTCAGGCCA AGGGACCAGG TTTGCAGGAG

CCCCCCTAG (SEQ ID NO:11);

7. MC-R1ESTc6
ATGGCTGTGC AGGGATCCCA GAGAAGACTT CTGGGCTCCC TCAACTCCAC CCCCACAGCC

ATCCCCCAGC TGGGGCTGGC TGCCAACCAG ACAGGAGCCC GGTGCCTGGA GGTGTCCATC

TCTGACGGGC TCTTCCTCAG CCTGGGGCTG GTGAGCTTGG TGAAGAACGC GCTGGTGGTG

GCCACCATCG CCAAGAACCG GAACCTGCAC TCACCCATGT ACTGCTTCAT CTGCTGCCTG

GCCTTGTCGG ACCTGCTGGT GAGCGGGAGC AACGTGCTGG AGACGGCCGT CATCCTCCTG
```

-continued

```
CTGGAGGCCG GTGCACTGGT GGCCCGGGCT GCGGTGCTGC AGCAGCTGGA CAATGTCATT

GACGTGATCA CCTGCAGCTC CATGCTGTCC AGCCTCTGCT TCCTGGGCGC CATCGCCGTG

GACCGCTACA TCTCCATCTT CTACGCACTG CGCTACCACA GCATCGTGAC CCTGCCGCGG

GCGCGGCAAG CCGTTGCGGC CATCTGGGTG GCCAGTGTCG TCTTCAGCAC GCTCTTCATC

GCCTACTACG ACCACGTGGC CGTCCTGCTG TGCCTCGTGG TCTTCTTCCT GGCTATGCTG

GTGCTCATGG CCGTGCTGTA CGTCCACATG CTGGCCCGGG CCTGCCAGCA CGCCCAGGGC

ATCGCCCGGC TCCACAAGAG GCAGCGCCCG GTCCACCAGG GCTTTGGCCT TAAAGGCGCT

GTCACCCTCA CCATCCTGCT GGGCATTTTC TTCCTCTGCT GGGGCCCCTT CTTCCTGCAT

CTCACACTCA TCGTCCTCTG CCCCGAGCAC CCCACGTGCG GCTGCATCTT CAAGAACTTC

AACCTCTTTC TCGCCCTCAT CATCTGCAAT GCCATCATCG ACCCCCTCAT CTACGCCTTC

CACAGCCAGG AGCTCCGCAG GACGCTCAAG GAGGTGCTGA CATGCTCCTG CTCTCAGGAC

CGTGCCCTCG TCAGCTGGGA TGTGAAGTCT CTGGGTGGAA GTGTGTGCCA AGAGCTACTC

CCACAGCAGC CCCAGGAGAA GGGGCTTTGT GACCAGAAAG CTTCATCCAC AGCCTTGCAG

CGGCTCCTGC AAAAGGAGGT GAAATCCCTG CCTCAGGCCA AGGGACCAGG TTTGCAGGAG

CCCCCCCTAG (SEQ ID NO:13);
```

8. mc1-3 (genomic)
```
ATGGCTGTGC AGGGATCCCA GAGAAGACTT CTGGGCTCCC TCAACTCCAC CCCCACAGCC

ATCCCCCAGC TGGGGCTGGC TGCCAACCAG ACAGGAGCCC GGTGCCTGGA GGTGTCCATC

TCTGACGGGC TCTTCCTCAG CCTGGGGCTG GTGAGCTTGG TGGAGAACGC GCTGGTGGTG

GCCACCATCG CCAAGAACCG GAACCTGCAC TCACCCATGT ACTGCTTCAT CTGCTGCCTG

GCCTTGTCGG ACCTGCTGGT GAGCGGGAGC AACGTGCTGG AGACGGCCGT CATCCTCCTG

CTGGAGGCCG GTGCACTGGT GGCCCAGGCT GCGGTGCTGC AGCAGCTGGA CCTGCCGCGG

GACGTGATCA CCTGCAGCTC CATGCTGTCC AGCCTCTGCT TCCTGGGCGC CATCGCCGCG

GACCGCTACA TCTCCATCTT CTACGCACTG CGCTACCACA GCATCGTGAC CCTGCCGCGG

GCGCGGCGAG CCGTTGCGGC CATCTGGGTG GCCAGTGTCG TCTTCAGCAC GCTCTTCATC

GCCTACTACG ACCACGTGGC CGTCCTGCTG TGCCTCGTGG TCTTCTTCCT GGCTATGCTG

GTGCTCATGG CCGTGCTGTA CGTCCACATG CTGGCCCGGG CCTGCCAGCA CGCCCAGGGC

ATCGCCCGGC TCCACAAGAG GCAGCGCCCG GTCCACCAGG GCTTTGGCCT TAAAGGCGCT

GTCACCCTCA CCATCCTGCT GGGCATTTTC TTCCTCTGCT GGGGCCCCTT CTTCCTGCAT

CTCACACTCA TCGTCCTCTG CCCCGAGCAC CCCACGTGCG GCTGCATCTT CAAGAACTTC

AACCTCTTTC TCGCCCTCAT CATCTGCAAT GCCATCATCG ACCCCCTCAT CTACGCCTTC

CACAGCCAGG AGCTCCGCAG GACGCTCAAG GAGGTGCTGA CATGCTCCTG gtgagcgcgg tgcacgcggc tttaagtgtg ctgggcagag ggaggtggtg atattgtgtg gtctggttcc tgtgtgaccc tgggcagttc cttacctccc tggtccccgt ttgtcaaaga ggatggacta aatgatctct gaangtgttg aagcgcggac ccttctgggt ccagggaggg gtccctgcaa aactccaggc aggacttctc accagcagtc gtggggaacg gaggaggaca tggggaggtt gtggggcctc aggctccggg caccaggggc caacctcagg ctcctaaaga gacattttcc gcccactcct gggacactcc gtctgctcca atgactgagc agcatccacc ccaccccatc tttgctgcca gCTCTCAGGA CCGTGCCCTC GTCAGCTGGG ATGTGAAGTC TCTGGGTGGA

AGTGTGTGCC AAGAGCTACT CCCACAGCAG CCCCAGGAGA AGGGGCTTTG TGACCAGAAA
```

-continued

GCTTCATCCA CAGCCTTGCA GCGGCTCCTG CAAAAGGAGG TGAAATCCCT GCCTCAGGCC

AAGGGACCAG GTTTGCAGGA GCCCCCCTAG (SEQ ID NO:15);

9. mc1-3 (open reading frame)
ATGGCTGTGC AGGGATCCCA GAGAAGACTT CTGGGCTCCC TCAACTCCAC CCCCACAGCC

ATCCCCCAGC TGGGGCTGGC TGCCAACCAG ACAGGAGCCC GGTGCCTGGA GGTGTCCATC

TCTGACGGGC TCTTCCTCAG CCTGGGGCTG GTGAGCTTGG TGGAGAACGC GCTGGTGGTG

GCCACCATCG CCAAGAACCG GAACCTGCAC TCACCCATGT ACTGCTTCAT CTGCTGCCTG

GCCTTGTCGG ACCTGCTGGT GAGCGGGAGC AACGTGCTGG AGACGGCCGT CATCCTCCTG

CTGGAGGCCG GTGCACTGGT GGCCCAGGCT GCGGTGCTGC AGCAGCTGGA CAATGTCATT

GACGTGATCA CCTGCAGCTC CATGCTGTCC AGCCTCTGCT TCCTGGGCGC CATCGCCGCG

GACCGCTACA TCTCCATCTT CTACGCACTG CGCTACCACA GCATCGTGAC CCTGCCGCGG

GCGCGGCGAG CCGTTGCGGC CATCTGGGTG GCCAGTGTCG TCTTCAGCAC GCTCTTCATC

GCCTACTACG ACCACGTGGC CGTCCTGCTG TGCCTCGTGG TCTTCTTCCT GGCTATGCTG

GTGCTCATGG CCGTGCTGTA CGTCCACATG CTGGCCCGGG CCTGCCAGCA CGCCCAGGGC

ATCGCCCGGC TCCACAAGAG GCAGCGCCCG GTCCACCAGG GCTTTGGCCT TAAAGGCGCT

GTCACCCTCA CCATCCTGCT GGGCATTTTC TTCCTCTGCT GGGGCCCCTT CTTCCTGCAT

CTCACACTCA TCGTCCTCTG CCCCGAGCAC CCCACGTGCG GCTGCATCTT CAAGAACTTC

AACCTCTTTC TCGCCCTCAT CATCTGCAAT GCCATCATCG ACCCCCTCAT CTACGCCTTC

CACAGCCAGG AGCTCCGCAG GACGCTCAAG GAGGTGCTGA CATGCTCCTG CTCTCAGGAC

CGTGCCCTCG TCAGCTGGGA TGTGAAGTCT CTGGGTGGAA GTGTGTGCCA AGAGCTACTC

CCACAGCAGC CCCAGGAGAA GGGGCTTTGT GACCAGAAAG CTTCATCCAC AGCCTTGCAG

CGGCTCCTGC AAAAGGAGGT GAAATCCCTG CCTCAGGCCA AGGGACCAGG TTTGCAGGAG

CCCCCCTAG (SEQ ID NO:17);

10. mc1-6 (genomic)
ATGGCTGTGC AGGGATCCCA GAGAAGACTT CGGGGCTCCC TCAACTCCAC CCCCACAGCC

ATCCCCCAGC TGGGGCTGGC TGCCAACCAG ACAGGAGCCC GGTGCCTGGA GGTGTCCATC

TCTGACGGGC TCTTCCTCAG CCTGGGGCTG GTGAGCTTGG TGGAGAACGC GCTGGTGGTG

GCCACCATCG CCAAGAACCG GAACCTGCAC TCACCCATGT ACTGCTTCAT CTGCTGCCTG

GCCTTGTCGG ACCTGCTGGT GAGCGGGAGC AACGTGCTGG AGACGGCCGT CATCCTCCTG

CTGGAGGCCG GTGCACTGGT GGCCCGGGCT GCGGTGCTGC AGCAGCTGGA CAATGTCATT

GACGTGATCA CCTGCAGCTC CATGCTGTCC AGCCTCTGCT TCCTGGGCGC CATCGCCGTG

GACCGCTACA TCTCCATCTT CTACGCACTG CGCTACCACA GCATCGTGAC CCTGCCGCGG

GCGCGGCGAG CCGTTGCGGC CCTCTGGGTG GCCAGTGTCG TCTTCAGCAC GCTCTTCATC

GCCTACTACG ACCACGTGGC CGTCCTGCTG TGCCTCGTGG TCTTCTTCCT GGCTATGCTG

GTGCTCATGG CCGTGCTGTA CGTCCACATG CTGGCCCGGG CCTGCCAGCA CGCCCAGGGC

ATCGCCCGGC TCCACAAGAG GCAGCGCCCG GTCCACCAGG GCTTTGGCCT TAAAGGCGCT

GTCACCCCCA CCATCCTGCT GGGCATTTTC TTCCTCTGCT GGGGCCCCTT CTTCCTGCAT

CTCACACTCA TCGTCCTCTG CCCCGAGCAC CCCACGTGCG GCTGCATCTT CAAGAACTTC

AACCTCTTTC TCGCCCTCAT CATCTGCAAT GCCTTCATCG ACCCCCTCAT CTACGCCTTC

CACAGCCAGG AGCTCCGCAG GACGCTCAAG GAGGTGCTGA CATGCTCCTG CATGCTCCTG gtgagcgcgg tgcacgcggc tttaagtgtg ctgggcagag ggaggtggtg atattgtgtg -continued

```
gtctggttcc tgtgtgaccc tgggcagttc cttacctccc tggtccccgt ttgtcaaaga ggatggacta aatgatctct gaangtgttg aagcgcggac ccttctgggt ccagggaggg gtccctgcaa aactccaggc aggacttctc accagcagtc gtggggaacg gaggaggaca tggggaggtt gtggggcctc aggctccggg caccaggggc caacctcagg ctcctaaaga gacattttcc gcccactcct gggacactcc gtctgctcca atgactgagc agcatccacc ccaccccatc tttgctgcca gCTCTCAGGA CCGTGCCCTC GTCAGCTGGG ATGTGAAGTC

TCTGGGTGGA AGTGTGTGCC AAGAGCTACT CCCACAGCAG CCCCAGGAGA AGGGGCTTTG

TGACCAGAAA GCTTCATCCA CAGCCTTGCA GCGGCTCCTG CAAAAGGAGG TGAAATCCCT

GCCTCAGGCC AAGGGACCAG GTTTGCAGGA GCCCCCCTAG (SEQ ID NO:18);
```

11. mc1-6 (open reading frame)
```
ATGGCTGTGC AGGGATCCCA GAGAAGACTT CTGGGCTCCC TCAACTCCAC CCCCACAGCC

ATCCCCCAGC TGGGGCTGGC TGCCAACCAG ACAGGAGCCC GGTGCCTGGA GGTGTCCATC

TCTGACGGGC TCTTCCTCAG CCTGGGGCTG GTGAGCTTGG TGGAGAACGC GCTGGTGGTG

GCCACCATCG CCAAGAACCG GAACCTGCAC TCACCCATGT ACTGCTTCAT CTGCTGCCTG

GCCTTGTCGG ACCTGCTGGT GAGCGGGAGC AACGTGCTGG AGACGGCCGT CATCCTCCTG

CTGGAGGCCG GTGCACTGGT GGCCCGGGCT GCGGTGCTGC AGCAGCTGGA CAATGTCATT

GACGTGATCA CCTGCAGCTC CATGCTGTCC AGCCTCTGCT TCCTGGGCGC CATCGCCGTG

GACCGCTACA TCTCCATCTT CTACGCACTG CGCTACCACA GCATCGTGAC CCTGCCGCGG

GCGCGGCGAG CCGTTGCGGC CCTCTGGGTG GCCAGTGTCG TCTTCAGCAC GCTCTTCATC

GCCTACTACG ACCACGTGGC CGTCCTGCTG TGCCTCGTGG TCTTCTTCCT GGCTATGCTG

GTGCTCATGG CCGTGCTGTA CGTCCACATG CTGGCCCGGG CCTGCCAGCA CGCCCAGGGC

ATCGCCCGGC TCCACAAGAG GCAGCGCCCG GTCCACCAGG GCTTTGGCCT TAAAGGCGCT

GTCACCCCCA CCATCCTGCT GGGCATTTTC TTCCTCTGCT GGGGCCCCTT CTTCCTGCAT

CTCACACTCA TCGTCCTCTG CCCCGAGCAC CCCACGTGCG GCTGCATCTT CAAGAACTTC

AACCTCTTTC TCGCCCTCAT CATCTGCAAT GCCTTCATCG ACCCCCTCAT CTACGCCTTC

CACAGCCAGG AGCTCCGCAG GACGCTCAAG GAGGTGCTGA CATGCTCCTG CTCTCAGGAC

CGTGCCCTCG TCAGCTGGGA TGTGAAGTCT CTGGGTGGAA GTGTGTGCCA AGAGCTACTC

CCACAGCAGC CCCAGGAGAA GGGGCTTTGT GACCAGAAAG CTTCATCCAC AGCCTTGCAG

CGGCTCCTGC AAAAGGAGGT GAAATCCCTG CCTCAGGCCA AGGGACCAGG TTTGCAGGAG

CCCCCCTAG (SEQ ID NO:19);
```

12. mc1-8 (genomic)
```
ATGGCTGTGC AGGGATCCCA GAGAAGACTT CTGGGCTCCC TCAACTCCAC CCCCACAGCC

ATCCCCCAGC TGGGGCTGGC TGCCAACCAG ACAGGAGCCC GGTGCCTGGA GGTGTCCATC

TCTGACGGGC TCTTCCTCAG CCTGGGGCTG GTGAGCTTGG TGGAGAACGC GCTGGTGGTG

GCCACCATCG CCAAGAACCG GAACCTGCAC TCACCCATGT ACTGCTTCAT CTGCTGCCTG

GCCTTGTCGG ACCTGCTGGT GAGCGGGAGC AACGTGCTGG AGACGGCCGT CATCCTCCTG

CTGGAGGCCG GTGCACTGGT GGCCCGGGCT GCGGTGCTGC AGCAGCTGGA CAATGTCATT

GACGTGATCA CCTGCAGCTC CATGCTGTCC AGCCTCTGCT TCCTGGGCGC CATCGCCGTG

GACCGCTACA TCTCCATCTT CTACGCACTG CGCTACCACA GCATCGTGAC CCTGCCGCGG

GCGCGGCGAG CCGTTGCGGC CCTCTGGGTG GCCAGTGTCG TCTTCAGCAC GCTCTTCATC

GCCTACTACG ACCACGTGGC CGTCCTGCTG TGCCTCGTGG TCTTCTTCCT GGCTATGCTG
```

-continued

```
GTGCTCATGG CCGTGCTGTA CGTCCACATG CTGGCCCGGG CCTGCCAGCA CGCCCAGGGC

ATCGCCCGGC TCCACAAGAG GCAGCGCCCG GTCCACCAGG GCTTTGGCCT TAAAGGCGCT

GTCACCCCCA CCATCCTGCT GGGCATTTTC TTCCTCTGCT GGGGCCCCTT CTTCCTGCAT

CTCACACTCA TCGTCCTCTG CCCCGAGCAC CCCACGTGCG GCTGCATCTT CAAGAACTTC

AACCTCTTTC TCGCCCTCAT CATCTGCAAT GCCTTCATCG ACCCCCTCAT CTACGCCTTC

CACAGCCAGG AGCTCCGCAG GACGCTCAAG GAGGTGCTGA CATGCTCCTG gtgagcgcgg tgcacgcggc tttaagtgtg ctgggcagag ggaggtggtg atattgtgtg gtctggttcc tgtgtgaccc tgggcagttc cttacctccc tggtccccgt ttgtcaaaga ggatggacta aatgatctct gaangtgttg aagcgcggac ccttctgggt ccagggaggg gtccctgcaa aactccaggc aggacttctc accagcagtc gtggggaacg gaggaggaca tggggaggtt gtggggcctc aggctccggg caccaggggc caacctcagg ctcctaaaga gacattttcc gcccactcct gggacactcc gtctgctcca atgactgagc agcatccacc ccaccccatc tttgctgcca gCTCTCAGGA CCGTGCCCTC GTCAGCTGGG ATGTGAAGTC TCTGGGTGGA

AGTGTGTGCC AAGAGCTACT CCCACAGCAG CCCCAGGAGA AGGGGCTTTG TGACCAGAAA

GCTTCATCCA CAGCCTTGCA GCGGCTCCTG CAAAAGGAGG TGAAATCCCT GCCTCAGGCC

AAGGGACCAG GTTTGCAGGA GCCCCCCTAG (SEQ ID NO:21);
```

13. mc1-8 (open reading frame)
```
ATGGCTGTGC AGGGATCCCA GAGAAGACTT CTGGGCTCCC TCAACTCCAC CCCCACAGCC

ATCCCCCAGC TGGGGCTGGC TGCCAACCAG ACAGGAGCCC GGTGCCTGGA GGTGTCCATC

TCTGACGGGC TCTTCCTCAG CCTGGGGCTG GTGAGCTTGG TGGAGAACGC GCTGGTGGTG

GCCACCATCG CCAAGAACCG GAACCTGCAC TCACCCATGT ACTGCTTCAT CTGCTGCCTG

GCCTTGTCGG ACCTGCTGGT GAGCGGGAGC AACGTGCTGG AGACGGCCGT CATCCTCCTG

CTGGAGGCCG GTGCACTGGT GGCCCGGGCT GCGGTGCTGC AGCAGCTGGA CAATGTCATT

GACGTGATCA CCTGCAGCTC CATGCTGTCC AGCCTCTGCT TCCTGGGCGC CATCGCCGTG

GACCGCTACA TCTCCATCTT CTACGCACTG CGCTACCACA GCATCGTGAC CCTGCCGCGG

GCGCGGCGAG CCGTTGCGGC CCTCTGGGTG GCCAGTGTCG TCTTCAGCAC GCTCTTCATC

GCCTACTACG ACCACGTGGC CGTCCTGCTG TGCCTCGTGG TCTTCTTCCT GGCTATGCTG

GTGCTCATGG CCGTGCTGTA CGTCCACATG CTGGCCCGGG CCTGCCAGCA CGCCCAGGGC

ATCGCCCGGC TCCACAAGAG GCAGCGCCCG GTCCACCAGG GCTTTGGCCT TAAAGGCGCT

GTCACCCCCA CCATCCTGCT GGGCATTTTC TTCCTCTGCT GGGGCCCCTT CTTCCTGCAT

CTCACACTCA TCGTCCTCTG CCCCGAGCAC CCCACGTGCG GCTGCATCTT CAAGAACTTC

AACCTCTTTC TCGCCCTCAT CATCTGCAAT GCCTTCATCG ACCCCCTCAT CTACGCCTTC

CACAGCCAGG AGCTCCGCAG GACGCTCAAG GAGGTGCTGA CATGCTCCTG CTCTCAGGAC

CGTGCCCTCG TCAGCTGGGA TGTGAAGTCT CTGGGTGGAA GTGTGTGCCA AGAGCTACTC

CCACAGCAGC CCCAGGAGAA GGGGCTTTGT GACCAGAAAG CTTCATCCAC AGCCTTGCAG

CGGCTCCTGC AAAAGGAGGT GAAATCCCTG CCTCAGGCCA AGGGACCAGG TTTGCAGGAG

CCCCCCTAG (SEQ ID NO:22);
```

14. mc-19 (genomic)
```
ATGGCTGTGC AGGGATCCCA GAGAAGACTT CTGGGCTCCC TCAACTCCAC CCCCACAGCC

ATCCCCCAGC TGGGGCTGGC TGCCAACCAG ACAGGAGCCC GGTGCCTGGA GGTGTCCATC

TCTGACGGGC TCTTCCTCAG CCTGGGGCTG GTGAGCTTGG TGGAGAACGC GCTGGTGGTG
```

```
GCCACCATCG CCAAGAACCG GAACCTGCAC TCACCCATGT ACTGCTTCAT CTGCTGCCTG

GCCTTGTCGG ACCTGCTGGT GAGCGGGAGC AACGTGCTGG AGACGGCCGT CATCCTCCTG

CTGGAGGCCG GTGCACTGGT GGCCCGGGCT GCGGTGCTGC AGCAGCTGGA CAATGTCATT

GACGTGATCA CCTGCAGCTC CATGCTGTCC AGCCTCTGCT TCCTGGGCGC CGTCGCCGTG

GACCGCTACA TCTCCATCTT CTACGCACTG CGCTACCACA GCATCGTGAC CCTGCCGCGG

GCGCGGCAAG CCGTTGCGGC CATCTGGGTG GCCAGTGTCG TCTTCAGCAC GCTCTTCATC

GCCTACTACG ACCACGTGGC CGTCCTGCTG TGCCTCGTGG TCTTCTTCCT GGCTATGCTG

GTGCTCATGG CCGTGCTGTA CGTCCACATG CTGGCCCGGG CCTGCCAGCA CGCCCAGGGC

ATCGCCCGGC TCCACAAGAG GCAGCGCCCG GTCCACCAGG GCTTTGGCCT TAAAGGCGCT

GTCACCCTCA CCATCCTGCT GGGCATTTTC TTCCTCTGCT GGGGCCCCTT CTTCCTGCAT

CTCACACTCA TCGTCCTCTG CCCCGAGCAC CCACGTGCG GCTGCATCTT CAAGAACTTC

AACCTCTTTC TCGCCCCCAT CATCTGCAAC GCCATCATCG ACCCCCTCAT CTACGCCTTC

CACAGCCAGG AGCTCCGCAG GACGCTCAAG GAGGTACTGA CATGCTCCTG CATGCTCCTG gtgagcgcgg tgcacgcggc tttaagtgtg ctgggcagag ggaggtggtg atattgtgtg gtctggttcc tgtgtgaccc tgggcagttc cttacctccc tggtcccgt ttgtcaaaga ggatggacta aatgatctct gaangtgttg aagcgcggac ccttctgggt ccagggaggg gtccctgcaa aactccaggc aggacttctc accagcagtc gtggggaacg gaggaggaca tggggaggtt gtggggcctc aggctccggg caccagggc caacctcagg ctcctaaaga gacattttcc gcccactcct gggacactcc gtctgctcca atgactgagc agcatccacc Ccacccccatc tttgctgcca gCTCTCAGGA CCGTGCCCTC GTCAGCTGGG ATGTGAAGTC

TCTGGGTGGA AGTGTGTGCC AAGAGCTACT CCCACAGCAG CCCCAGGAGA AGGGGCTTTG

TGACCAGAAA GCTTCATCCA CAGCCTTGCA GCGGCTCCTG CAAAAGGAGG TGAAATCCCT

GCCTCAGGCC AAGGGACCAG GTTTGCAGGA GCCCCCTAG (SEQ ID NO:24);

15. mc1-8 (open reading frame)
ATGGCTGTGC AGGGATCCCA GAGAAGACTT CTGGGCTCCC TCAACTCCAC CCCCACAGCC

ATCCCCCAGC TGGGGCTGGC TGCCAACCAG ACAGGAGCCC GGTGCCTGGA GGTGTCCATC

TCTGACGGGC TCTTCCTCAG CCTGGGGCTG GTGAGCTTGG TGGAGAACGC GCTGGTGGTG

GCCACCATCG CCAAGAACCG GAACCTGCAC TCACCCATGT ACTGCTTCAT CTGCTGCCTG

GCCTTGTCGG ACCTGCTGGT GAGCGGGAGC AACGTGCTGG AGACGGCCGT CATCCTCCTG

CTGGAGGCCG GTGCACTGGT GGCCCGGGCT GCGGTGCTGC AGCAGCTGGA CAATGTCATT

GACGTGATCA CCTGCAGCTC CATGCTGTCC AGCCTCTGCT TCCTGGGCGC CGTCGCCGTG

GACCGCTACA TCTCCATCTT CTACGCACTG CGCTACCACA GCATCGTGAC CCTGCCGCGG

GCGCGGCAAG CCGTTGCGGC CATCTGGGTG GCCAGTGTCG TCTTCAGCAC GCTCTTCATC

GCCTACTACG ACCACGTGGC CGTCCTGCTG TGCCTCGTGG TCTTCTTCCT GGCTATGCTG

GTGCTCATGG CCGTGCTGTA CGTCCACATG CTGGCCCGGG CCTGCCAGCA CGCCCAGGGC

ATCGCCCGGC TCCACAAGAG GCAGCGCCCG GTCCACCAGG GCTTTGGCCT TAAAGGCGCT

GTCACCCTCA CCATCCTGCT GGGCATTTTC TTCCTCTGCT GGGGCCCCTT CTTCCTGCAT

CTCACACTCA TCGTCCTCTG CCCCGAGCAC CCACGTGCG GCTGCATCTT CAAGAACTTC

AACCTCTTTC TCGCCCCCAT CATCTGCAAC GCCATCATCG ACCCCCTCAT CTACGCCTTC

CACAGCCAGG AGCTCCGCAG GACGCTCAAG GAGGTACTGA CATGCTCCTG CTCTCAGGAC

CGTGCCCTCG TCAGCTGGGA TGTGAAGTCT CTGGGTGGAA GTGTGTGCCA AGAGCTACTC
```

-continued

```
CCACAGCAGC CCCAGGAGAA GGGGCTTTGT GACCAGAAAG CTTCATCCAC AGCCTTGCAG

CGGCTCCTGC AAAAGGAGGT GAAATCCCTG CCTCAGGCCA AGGGACCAGG TTTGCAGGAG

CCCCCCTAG (SEQ ID NO:25).
```

The above-exemplified isolated DNA molecules encode polymorphisms of human MC-R1B, clones comprising an open reading frame which encodes an additional 65 amino acids (from residue 318 to 382; SEQ ID NO:27), as well as a substitution of a Cys-317 residue for the Trp-317 residue of the MC-R1A protein. More specifically, SEQ ID NOs: 1, 3, 5, 7, 9, 11, and 13 represent cDNA clones which contain 1149 nucleotides, with an open reading frame nucleotide 1 to nucleotide 1146, with a "TAG" termination codon from nucleotides 1147–1149. These open reading frames encode a human MC-R1B protein 382 amino acids in length, as shown in FIGS. 5A–5F and as set forth in SEQ ID NOs: 2, 4, 6, 8, 10, 12, and 14, respectively.

The present invention also relates to MC-R1B genomic clones, the predicted open reading frames for these clones and the MC-R1B protein translated from the respective mRNA molecule of each genomic clone. This specification exemplifies, but is not necessarily limited to, MC-R1 polymorphic variations as disclosed in mc1-3 (SEQ ID NO:15), mc1-6 (SEQ ID NO:18), mc1-6 (SEQ ID NO:21), mc1-9 (SEQ ID NO:24). These DNA molecules represent human MC-R1B genomic clones which contain 1530 nucleotides, with an intron from nucleotides 951–1331 (see Example Section 1). The respective open reading frame of each of these genomic clones is disclosed in SEQ ID NO: 16 (mc1-3), SEQ ID NO: 19 (mc1-6), SEQ ID NO: 22 (mc1-6), and SEQ ID NO: 25 (mc1-9). Each of these open reading frames encodes a putative protein comprising 382 amino acids as disclosed in SEQ ID NO: 17 (pro-mc1-3), SEQ ID NO: 20 (pro-mc1-6), SEQ ID NO: 23 (pro-mc1-6), and SEQ ID NO: 25 (pro-mc1-9).

The present invention also relates to biologically active fragments or mutants of MC-R1 splice variants which encodes mRNA expressing a novel human MC-R1B. Any such biologically active fragment and/or mutant of the MC-R1 splice variants disclosed herein will encode either a protein or protein fragment which at least substantially mimics the pharmacological properties of a wild-type MC-R1 protein and comprises at least a portion of the COOH terminal amino acid extension disclosed as SEQ ID NO:27. Any such polynucleotide includes but is not necessarily limited to nucleotide substitutions, deletions, additions, amino-terminal truncations and carboxy-terminal truncations such that these mutations encode mRNA which express a protein or protein fragment of diagnostic, therapeutic or prophylactic use and would be useful for screening for agonists and/or antagonists for MC-R1 function.

A preferred aspect of this portion of the present invention is set forth as SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:16, SEQ ID NO:18; SEQ ID NO:19, SEQ ID NO:21, SEQ ID NO:22, SEQ ID NO:24, and SEQ ID NO:25, human nucleic acid molecules which comprise the complete open reading frame for the MC-R1 proteins of the present invention.

The isolated nucleic acid molecules of the present invention may include a deoxyribonucleic acid molecule (DNA), such as genomic DNA and complementary DNA (cDNA), which may be single (coding or noncoding strand) or double stranded, as well as synthetic DNA, such as a synthesized, single stranded polynucleotide. The isolated nucleic acid molecule of the present invention may also include a ribonucleic acid molecule (RNA), especially a mRNA molecule generated from a human MC-R1 splice variant genomic clone as disclosed in mc1-3 (SEQ ID NO:15), mc1-6 (SEQ ID NO:18), mc1-6 (SEQ ID NO:21), mc1-9 (SEQ ID NO:24) and their respective open reading frames, SEQ ID NO: 16 (mc1-3), SEQ ID NO: 19 (mc1-6), SEQ ID NO: 22 (mc1-6), and SEQ ID NO: 25 (mc1-9).

It is known that there is a substantial amount of redundancy in the various codons which code for specific amino acids. Therefore, this invention is also directed to those DNA sequences encode RNA comprising alternative codons which code for the eventual translation of the identical amino acid, as shown below:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asp=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser-Serine: codons AGC, AGU, UCA, UCC, UCG, UCU
T=Thr-Threonine: codons ACA, ACC, ACG, ACU
V=Val-Valine: codons GUA, GUC, GUG, GUU
W=Trp=Tryptophan: codon UGG
Y=Tyr=Tyrosine: codons UAC, UAU Therefore, the present invention discloses codon redundancy which may result in differing DNA molecules expressing an identical protein. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally occurring peptide. Methods of altering the DNA sequences include but are not limited to site directed mutagenesis. Examples of altered properties include but are not limited to changes in the affinity of an enzyme for a substrate or a receptor for a ligand.

Any of a variety of procedures may be used to clone human MC-R1 splice variant, including but not limited to the procedure outlined in the Example sections. These methods include, but are not limited to, (1) a RACE PCR cloning technique (Frohman, et al., 1988, *Proc. Natl. Acad. Sci. USA* 85: 8998–9002). 5' and/or 3' RACE may be performed to generate a full-length cDNA sequence. This strategy involves using gene-specific oligonucleotide primers for PCR amplification of human MC-R1B cDNA. These gene-specific primers are designed through identification of an expressed sequence tag (EST) nucleotide sequence which has been identified by searching any number of publicly available nucleic acid and protein databases; (2) direct functional expression of the human MC-R1B cDNA following the construction of a human MC-R1B-containing cDNA library in an appropriate expression vector system; (3) screening a human MC-R1B-containing cDNA library constructed in a bacteriophage or plasmid shuttle vector with a labeled degenerate oligonucleotide probe designed from the amino acid sequence of the human MC-R1B protein; (4) screening a human MC-R1B-containing cDNA library constructed in a bacteriophage or plasmid shuttle vector with a partial cDNA encoding the human MC-R1B protein. This partial cDNA is obtained by the specific PCR amplification of human MC-R1B DNA fragments through the design of degenerate oligonucleotide primers from the amino acid sequence known for other kinases which are related to the human MC-R1B protein; (5) screening a human MC-R1B-containing cDNA library constructed in a bacteriophage or plasmid shuttle vector with a partial cDNA or oligonucleotide with homology to a mammalian MC-R1B protein. This strategy may also involve using gene-specific oligonucleotide primers for PCR amplification of human MC-R1B cDNA identified as an EST as described above; or (6) designing 5' and 3' gene specific oligonucleotides using SEQ ID NO: 1 as a template so that either the full-length cDNA may be generated by known RACE techniques, or a portion of the coding region may be generated by these same known RACE techniques to generate and isolate a portion of the coding region to use as a probe to screen one of numerous types of cDNA and/or genomic libraries in order to isolate a full-length version of the nucleotide sequence encoding human MC-R1B.

It is readily apparent to those skilled in the art that other types of libraries, as well as libraries constructed from other cell types- or species types, may be useful for isolating a human MC-R1B-encoding DNA or a human MC-R1B homologue. Other types of libraries include, but are not limited to, cDNA libraries derived from other human cells.

It is also readily apparent to those skilled in the art that suitable cDNA libraries may be prepared from cells or cell lines which have MC-R1B activity. The selection of cells or cell lines for use in preparing a cDNA library to isolate a cDNA encoding human MC-R1B may be done by first measuring cell-associated MC-R1B activity using any known assay available for such a purpose.

Preparation of cDNA libraries can be performed by standard techniques well known in the art. Well known cDNA library construction techniques can be found for example, in Sambrook et al., 1989, *Molecular Cloning: A Laboratory Manual*; Cold Spring Harbor Laboratory, Cold Spring Harbor, N.Y. Complementary DNA libraries may also be obtained from numerous commercial sources, including but not limited to Clontech Laboratories, Inc. and Stratagene.

It is also readily apparent to those skilled in the art that DNA encoding human MC-R1B may also be isolated from a suitable genomic DNA library. Construction of genomic DNA libraries can be performed by standard techniques well known in the art. Well known genomic DNA library construction techniques can be found in Sambrook, et al., supra.

In order to clone the human MC-R1B gene by one of the preferred methods, the amino acid sequence or DNA sequence of human MC-R1B or a homologous protein may be necessary. To accomplish this, the MC-R1B protein or a homologous protein may be purified and partial amino acid sequence determined by automated sequenators. It is not necessary to determine the entire amino acid sequence, but the linear sequence of two regions of 6 to 8 amino acids can be determined for the PCR amplification of a partial human MC-R1B DNA fragment. Once suitable amino acid sequences have been identified, the DNA sequences capable of encoding them are synthesized. Because the genetic code is degenerate, more than one codon may be used to encode a particular amino acid, and therefore, the amino acid sequence can be encoded by any of a set of similar DNA oligonucleotides. Only one member of the set will be identical to the human MC-R1B sequence but others in the set will be capable of hybridizing to human MC-R1B DNA even in the presence of DNA oligonucleotides with mismatches. The mismatched DNA oligonucleotides may still sufficiently hybridize to the human MC-R1B DNA to permit identification and isolation of human MC-R1B encoding DNA. Alternatively, the nucleotide sequence of a region of an expressed sequence may be identified by searching one or more available genomic databases. Gene-specific primers may be used to perform PCR amplification of a cDNA of interest from either a cDNA library or a population of cDNAs. An appropriate nucleotide sequence for use in a PCR-based method may be obtained from any of the identified MC-R1B splice variants described herein, either for the purpose of isolating overlapping 5' and 3' RACE products for generation of a full-length sequence coding for human MC-R1B, or to isolate a portion of the nucleotide sequence coding for human MC-R1B for use as a probe to screen one or more cDNA- or genomic-based libraries to isolate a full-length sequence encoding human MC-R1B or human MC-R1B-like proteins.

Included in the present invention are DNA sequences that hybridize to the nucleotide sequences of the various described MC-R1B splice variants (i.e., SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:16, SEQ ID NO:18; SEQ ID NO:19, SEQ ID NO:21, SEQ ID NO:22, SEQ ID NO:24, and SEQ ID NO:25) under stringent conditions. By way of example, and not limitation, a procedure using conditions of high stringency is as follows: Prehybridization of filters containing DNA is carried out for 2 hours to overnight at 65° C. in buffer composed of 6×SSC, 5×Denhardt's solution, and 100 $\mu$g/ml denatured salmon sperm DNA. Filters are hybridized for 12 to 48 hrs at 65° C. in prehybridization mixture containing 100 $\mu$g/ml denatured salmon sperm DNA and 5–20×10$^6$ cpm of $^{32}$P-labeled probe. Washing of filters is done at 37° C. for 1 hr in a solution containing 2×SSC, 0.1% SDS. This is followed by a wash in 0.1×SSC, 0.1% SDS at 50° C. for 45 min. before autoradiography. Other procedures using conditions of high stringency would include either a hybridization step carried out in 5×SSC, 5×Denhardt's solution, 50% formamide at 42° C. for 12 to 48 hours or a washing step carried out in 0.2×SSPE, 0.2% SDS at 65° C. for 30 to 60 minutes.

Reagents mentioned in the foregoing procedures for carrying out high stringency hybridization are well known in the art. Details of the composition of these reagents can be found in, e.g., Sambrook et al., 1989, *Molecular Cloning: A Laboratory Manual*; Cold Spring Harbor Laboratory, Cold Spring Harbor, N.Y. In addition to the foregoing, other conditions of high stringency which may be used are well known in the art.

The present invention also relates to a substantially purified forms of the human MC-R1B protein which comprise the amino acid sequences disclosed in FIGS. 5A–5F and as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:17, SEQ ID NO:20, SEQ ID NO:23, and SEQ ID NO:26. These MC-R1 proteins comprise a 65 amino acid extension at the COOH-terminus when compared to known human MC-R1 and are referred to throughout this specification as MC-R1B proteins. The exemplified amino acid sequences are listed below:

1. MC-R1ESTc11

MAVQGSQRRL LGSLNSTPTA IPQLGLAANQ TGARCLEVSI SDGLFLSLGL VSLVENALVV

ATIAKNRNLH SPMYCFICCL ALSDLLVSGS NVLETAVILL LEAGALVARA AVLQQLDNVI

DVITCSSMLS SLCFLGAIAV DRYISIFYAL RYHSIVTLPR ARQAVAAIWV ASVVFSTLFI

AYYDHVAVLL CLVVFFLAML VLMAVLYVHM LARACQHAQG IARLHKRQRP VHQGFGLKGA

VTLTILLGIF FLCWGPFFLH LThIVLCPEH PTCGCIFKNF NLFLALIICN AIIDPLIYAF

HSQELRRTLK EVLTCSCSQD RALVSWDVKS LGGSVCQELL PQQPQEKGPC DQKASSTALQ

RLLQKEVKSL PQAKGPGLQE PP (SEQ ID NO:2);

2. MC-R1ESTC11.6

MAVQGSQRRL LGSLNSTPTA IPQLGLAANQ TGARCLEVSI SDGLFLSLGL VSLVENALVV

ATIAKNRNLH SPMYCFICCL ALSDLLVSGS NVLETAVILL LEAGALVARA AVLQQLDNVI

DVITCSSMLS SLCFLGAIAV DRYISIFYAL RYHSIVTLPR ARQAVAAIWV ASVVFSTLFI

AYYDHVAVLL CLVVFFLAML VLMAVLYVHM LARACQHAQG IARLHKRQRP VHQGFGLKGA

VTLTILLGIF FLCWGPFFLH LTLIVLCPEH PTCGCIFKNF NLFLALIICN AIIDPLIYAF

HSQELRRTLK EVLTCSCSQD RALVSWDVKS LGGSVCQELL PQQPQEKGLC DQKASSTALQ

RLLQKEVKSL PQAKGPGLQE PP (SEQ ID NO:4);

3. MC-R1ESTc12

MAVQGSQRRL LGSLNSTPTA IPQLGLAANQ TGARCLEVSI SDGLFLSLGL VSLVKNALVV

ATIAKNRNLH SPMYCFICCL ALSDLLVSGS NVLETAVILL LEAGALVARA AVLQQLDNVI

DVITCSSMLS SLCFLGAIAV DRYISIFYAL RYHSIVTLPR ARQAVAAIWV ASVVFSTLFI

AYYDHVAVLL CLVVFFLAML VLMAVLYVHM LAAACQHAQG IARLHKRQRP VHQGFGLKGA

VTLTILLGIF FLCWGPFFLH LTLIVLCPEH PTCGCIFKNF NLFLALIICN AIIDPLIYAF

HSQELRRTLK EVLTCSCSQD RALVSWDVKS LGGSVCQELL PQQPQEKGLC DQKASSTALQ

RLLQKEVKSL PQAKGPGLQE PP (SEQ ID NO:6);

4. MC-R1ESTc2

MAVQGSQRRL LGSLNSTPTA IPQLGLAANQ TGARCLEVSI SDGLFLSLGL VSLVENALVV

ATIAKNRNLH SPMYCFICCL ALSDLLVSGS NVLETAVILL LEAGALVARA AVLQQLDNVI

DVITCSFMLS SLCFLGAIAV DRYISIFYAL CYHSIVTLPR ARRAVAAIWV ASVVFSTLFI

AYYDHVAVLL CLVVFFLAML VLMAVLYVHM LARACQHAQG IARLHKRQRP VHQGFGLKGA

VTLTILLGIF FLCWGPFFLH LTLIVLCPEH PTCGCIFKNF NLFLALIICN AIIDPLIYAF

HSQELRRTLK EVLTCSCSQD RALVSWDVKS LGGSVCQELL PQQPQEKGLC DQKASSTALQ

RLLQKEVKSL PQAKGPGLQE PP (SEQ ID NO:8);

5. MC R1ESTc4

MAVQGSQPRL LGSLNSTPTA IPQLGLAANQ TGARCLEVSI SDGLFLSLGL VSLVENALVV

ATIAKNRNLH SPMYCFICCL ALSDLLVSGS NVLETAVILL LEAGALVARA AVLQQLDNVI

-continued

DVITCSSMLS SLCFLGAIAV DRYISIFYAL RYHSIVTLPR ARRAVAAIWV ASVVFSTLFI

AYYDHAAVLL CLVVFFLAML VLMAVLYVHM LARACQHAQG IARLHKRQRP VHQGFGLKGA

VTLTILLGIF FLCWGPFFLH LTLIVLCPEH PTCGCIFKNF NLFLALIICN AIIDPLIYAF

HSQELRRTLK EVLTCSCSQD RALVSWDVKS LGGSVCQERL PQQPQEKGLC DQKASSTALQ

RLLQKGVKSL PQAKGPGLQE PP (SEQ ID NO:10);

6. MC-R1ESTc5

MAVQGSQRRL LGSLNSTPTA IPQLGLAANQ TGARCLEVSI SDGLFLSLGL VSLVKNALVV

ATIAKNRNLH SPMYCFICCL ALSDLLVSGS NVLETAVILL LEAGALVARA AVLQQLDNVI

DVITCSSMLS SLCFLGAIAV DRYISIFYAL RYHSIVTLPR ARQAVAAIWV ASVVFSTLFI

AYYDHVAVLL CLVVFFLAML VLMAVLYVHM LARACQHAQG IARLHKRQRP VHQGFGLKGA

VTLTILLGIF FLCWGPFFLH LTLIVLCPEH PTCGCIFKNF NLFLALIICN AIIDPLIYAF

HSQELRRTLK EVLTCSCSQD RALVSWDVKS LGGSVCQELL PQQPQEKGLC DQKASSTALQ

RLLQKEVKSL PQAKGPGLQE PP (SEQ ID NO:12);

7. MC-R1ESTc6

MAVQGSQRRL LGSLNSTPTA IPQLGLAANQ TGARCLEVSI SDGLFLSLGL VSLVKNALVV

ATIAKNRNLH SPMYCFICCL ALSDLLVSGS NVLETAVILL LEAGALVARA AVLQQLDNVI

DVITCSSMLS SLCFLGATAV DRYISIFYAL RYHSIVTLPR ARQAVAAIWV ASVVFSTLFI

AYYDHVAVLL CLVVFFLAML VLMAVLYVHM LARACQHAQG IARLHKRQRP VHQGFGLKGA

VTLTILLGIF FLCWGPFFLH LTLIVLCPEH PTCGCIFKNF NLFLALIICN AIIDPLIYAF

HSQELRRTLK EVLTCSCSQD RALVSWDVKS LGGSVCQELL PQQPQEKGLC DQKASSTALQ

RLLQKEVKSL PQAKGPGLQE PP (SEQ ID NO:14);

8. pro mc1-3

MAVQGSQRRL LGSLNSTPTA IPQLGLAANQ TGARCLEVSI SDGLFLSLGL VSLVENALVV

ATIAKNRNLH SPMYCFICCL ALSDLLVSGS NVLETAVILL LEAGALVAQA AVLQQLDNVI

DVITCSSMLS SLCFLGAIAA DRYISIFYAL RYHSIVTLPR ARRAVAAIWV ASVVFSTLFI

AYYDHVAVLL CLVVFFLAML VLMAVLYVHM LARACQHAQG IARLHKRQRP VHQGFGLKGA

VTLTILLGIF FLCWGPFFLH LTLIVLCPEH PTCGCIFKNF NLFLALIICN AIIDPLIYAF

HSQELRRTLK EVLTCSCSQD RALVSWDVKS LGGSVCQELL PQQPQEKGLC DQKASSTALQ

RLLQKKVKSL PQAKGPGLQE PP (SEQ ID NO:17);

9. pro mc1-6

MAVQGSQRRL LGSLNSTPTA IPQLGLAANQ TGARCLEVSI SDGLFLSLGL VSLVENALVV

ATIAKNRNLH SPMYCFICCL ALSDLLVSGS NVLETAVILL LEAGALVARA AVLQQLDNVI

DVITCSSMLS SLCFLGAIAV DRYISIFYAL RYHSIVTLPR ARQAVAAIWV ASVVFSTLFI

AYYDHVAVLL CLVVFFLAML VLMAVLYVHM LARACQHAQG IARLHKRQRP VHQGFGLKGA

VTLTILLGIF FLCWGPFFLH LTLIVLCPEH PTCGCIFKNF NLFLALIICN AIIDPLIYAF

HSQELRRTLK EVLTCSRSQD RALVSWDVKS LGGSVCQELL PQQPQEKGLC DQKASSTALQ

RLLQKKVKSL PQAKGPGLQE PP (SEQ ID NO:20);

10. pro mc1-8

MAVQGSQRRL LGSLNSTPTA IPQLGLAANQ TGARCLEVSI SDGLFLSLGL VSLVENALVV

ATIAKNRNLH SPMYCFICCL ALSDLLVSGS NVLETAVILL LEAGALVARA AVLQQLDNVI

```
                        -continued
DVITCSSMLS  SLCFLGAIAV  DRYISIFYAL  RYHSIVTLPR  ARRAVAALWV  ASVVFSTLFI

AYYDHVAVLL  CLVVFFLAML  VLMAVLYVHM  LARACQHAQG  IARLHKRQRP  VHQGFGLKGA

VTPTILLGIF  FLCWGPFFLH  LTLIVLCPEH  PTCGCIFKNF  NLFLALIICN  AFIDPLTYAF

HSQELRRTLK  EVLTCSCSQD  RALVSWDVKS  LGGSVCQELL  PQQPQEKGLC  DQKASSTALQ

RLLQKEVKSL  PQAKGPGLQE  PP  (SEQ ID NO:23);

11. pro mc-1-9

MAVQGSQRRL  LGSLNSTPTA  IPQLGLAANQ  TGARCLEVSI  SDGLFLSLGL  VSLVENALVV

ATIAKNRNLH  SPMYCFICCL  ALSDLLVSGS  NVLETAVILL  LEAGALVARA  AVLQQLDNVI

DVITCSSMLS  SLCFLGAVAV  DRYISIFYAL  RYHSIVTLPR  ARQAVAAIWV  ASVVFSTLFI

AYYDHVAVLL  CLVVFFLAAL  VLLAVLYVHM  LARACQHAQG  IARLHKRQRP  VHQGFGLKGA

VTLTILLGIF  FLCWGPFFLH  LTLIVLCPEH  PTCGCIFKNF  NLFLAPIICN  AIIDPLIYAF

HSQELRRTLK  EVLTCSCSQD  RALVSWDVKS  LGGSVCQELL  PQQPQEKGLC  DQKASSTALQ

RLLQKKVKSL  PQAKGPGLQE  PP  (SEQ ID NO:26);
``` wherein M=Met (methionine), F=Phe (phenylalanine), L=Leu (leucine), I=Ile (isoleucine), V=Val (valine), S=Ser (serine), P=Pro (proline), T=Thr (threonine), A=Ala (alanine), Y=Tyr (tyrosine), H=His (histidine), Q=Gln (glutamine), N=Asn (asparagine), K=Lys (lysine), D=Asp (aspartic acid), E=Glu (glutamic acid); C=Cys (cysteine), W=Trp (tryptophan), R=Arg (arginine), and G=Gly (glycine).

These MC-R1B proteins comprise a 65 amino acid extension at the COOH-terminus when compared to known human MC-R1 and are referred to throughout this specification as MC-R1B proteins. More specifically, amino acid residue 317 of the MC-R1B proteins is Cys whereas the COOH-terminal amino acid residue 317 of known MC-R1A proteins is Trp. From amino acid residue 318 through the COOH-terminal amino acid at 382 of the MC-R1B proteins disclosed herein, the amino acid sequence is as set forth in SEQ ID NO:27, as shown below: SQD RALVSWDVKS LGGSVCQELL PQQPQEKGLC DQKASSTALQ RLLQKEVKSL PQAKGPGLQE PP (SEQ ID NO:27).

The present invention also relates to biologically active fragments and/or mutants of these human MC-R1B proteins comprising the amino acid sequence set forth as SEQ ID NO:2, including but not necessarily limited to amino acid substitutions, deletions, additions, amino terminal truncations and carboxy-terminal truncations such that these mutations provide for proteins or protein fragments of diagnostic, therapeutic or prophylactic use and would be useful for screening for agonists and/or antagonists for MC-R1B function.

Various preferred aspects of the invention represent human MC-R1B proteins as disclosed in FIGS. 5A–5F and as set forth as SEQ ID NO:2, SEQ ID NO:4, SEQ ID NO:6, SEQ ID NO:8, SEQ ID NO:10, SEQ ID NO:12, SEQ ID NO:14, SEQ ID NO:17, SEQ ID NO:20, SEQ ID NO:23, and SEQ ID NO:26, all of which comprise the 65 amino acid COOH-terminal extension as set forth in SEQ ID NO:27.

The present invention also relates to modified MC-R1B polypeptides which have amino acid deletions, additions, or substitutions but that still retain substantially the same biological activity as MC-R1B. It is generally accepted that single amino acid substitutions do not usually alter the biological activity of a protein (see, e.g., *Molecular Biology of the Gene*, Watson et al., 1987, Fourth Ed., The Benjamin/Cummings Publishing Co., Inc., page 226; and Cunningham & Wells, 1989, *Science* 244:1081–1085). Accordingly, the present invention includes isolated nucleic acid molecules and expressed MC-R1B proteins wherein one amino acid substitution is generated and which this protein retains substantially the same biological activity as wild-type MC-R1B. The present invention also includes isolated nucleic acid molecules and expressed MC-R1B proteins wherein two or more amino acid substitution is generated wherein this protein retains substantially the same biological activity as wild-type MC-R1B. In particular, the present invention includes embodiments where the above-described substitutions are conservative substitutions. In particular, the present invention includes embodiments where the above-described substitutions do not occur in the ligand-binding domain of MC-R1B.

Following expression of MC-R1B in a host cell, MC-R1B protein may be recovered to provide MC-R1B protein in active form. Several MC-R1B protein purification procedures are available and suitable for use. Recombinant MC-R1B protein may be purified from cell lysates and extracts by various combinations of, or individual application of salt fractionation, ion exchange chromatography, size exclusion chromatography, hydroxylapatite adsorption chromatography and hydrophobic interaction chromatography. In addition, recombinant MC-R1B protein can be separated from other cellular proteins by use of an immunoaffinity column made with monoclonal or polyclonal antibodies specific for full-length MC-R1B protein, or polypeptide fragments of MC-R1B protein.

The present invention also relates to isolated nucleic acid molecules which are fusion constructions expressing fusion proteins useful in assays to identify compounds which modulate wild-type vertebrate MC-R1B activity. One aspect of this portion of the invention includes, but is not limited to, glutathione S-transferase (GST)-MC-R1B fusion constructs which include, but are not limited to, either the intracellular domain of MC-R1B as an in-frame fusion at the carboxy terminus of the GST gene or the extracellular and transmembrane ligand binding domain of MC-R1B fused to an GST or immunoglobulin gene by methods known to one of ordinary skill in the art. Recombinant GST-MC-R1B fusion proteins may be expressed in various expression systems, including *Spodoptera frugiperda* (Sf21) insect cells (Invitrogen) using a baculovirus expression vector (pAcG2T, Pharmingen).

The present invention also relates to subcellular membrane fractions from the recombinant host cells (both prokaryotic and eukaryotic as well as both stably and transiently transformed cells) which contain the nucleic acids of the present invention. These subcellular membrane fractions will comprise either wild-type or mutant forms of MC-R1B proteins at levels substantially above endogenous levels and hence will be useful in various assays described throughout this specification.

The present invention also relates to recombinant vectors and recombinant hosts, both prokaryotic and eukaryotic, which contain the substantially purified nucleic acid molecules disclosed throughout this specification. The nucleic acid molecules of the present invention encoding MC-R1B splice variants, in whole or in part, can be linked with other DNA molecules, i.e., DNA molecules to which the MC-R1B are not naturally linked, to form "recombinant DNA molecules" containing the receptor. The novel DNA sequences of the present invention can be inserted into vectors which comprise nucleic acids encoding a MC-R1B or a functional equivalent. These vectors may be comprised of DNA or RNA; for most cloning purposes DNA vectors are preferred. Typical vectors include plasmids, modified viruses, bacteriophage and cosmids, yeast artificial chromosomes and other forms of episomal or integrated DNA that can encode a MC-R1B. It is well within the purview of the skilled artisan to determine an appropriate vector for a particular gene transfer or other use.

To this end, the present invention also includes vectors containing an MC-R1B gene, host cells containing the vectors, and methods of making substantially pure MC-R1B protein comprising the steps of introducing the MC-R1B gene into a host cell, and cultivating the host cell under appropriate conditions such that MC-R1B is produced. The MC-R1B so produced may be harvested from the host cells in conventional ways. Therefore, the present invention also relates to methods of expressing the MC-R1B protein and biological equivalents disclosed herein, assays employing these gene products, recombinant host cells which comprise DNA constructs which express these receptor proteins, and compounds identified through these assays which act as agonists or antagonists of MC-R1B activity.

The cloned MC-R1B cDNA obtained through the methods described above may be recombinantly expressed by molecular cloning into an expression vector (such as pcDNA3.neo, pcDNA3.1, pCR2.1, pBlueBacHis2 or pLITMUS28) containing a suitable promoter and other appropriate transcription regulatory elements, and transferred into prokaryotic or eukaryotic host cells to produce recombinant MC-R1B. Techniques for such manipulations can be found described in Sambrook, et al., supra, are discussed at length in the Example section and are well known and easily available to the artisan of ordinary skill in the art.

A variety of mammalian expression vectors may be used to express recombinant MC-R1B in mammalian cells. Expression vectors are defined herein as DNA sequences that are required for the transcription of cloned DNA and the translation of their mRNAs in an appropriate host. Such vectors can be used to express eukaryotic DNA in a variety of hosts such as bacteria, blue green algae, plant cells, insect cells and animal cells. Specifically designed vectors allow the shuttling of DNA between hosts such as bacteria-yeast or bacteria-animal cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses. Commercially available mammalian expression vectors which may be suitable for recombinant MC-R1B expression, include but are not limited to, pcDNA3.neo (Invitrogen), pcDNA3.1 (Invitrogen), pCI-neo (Promega), pLITMUS28, pLITMUS29, pLITMUS38 and pLITMUS39 (New England Bioloabs), pcDNAI, pcDNAIamp (Invitrogen), pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and IZD35 (ATCC 37565).

Also, a variety of bacterial expression vectors may be used to express recombinant MC-R1B in bacterial cells. Commercially available bacterial expression vectors which may be suitable for recombinant MC-R1B expression include, but are not limited to pCR2.1 (Invitrogen), pET11a (Novagen), lambda gt11 (Invitrogen), and pKK223-3 (Pharmacia).

In addition, a variety of fungal cell expression vectors may be used to express recombinant MC-R1B in fungal cells. Commercially available fungal cell expression vectors which may be suitable for recombinant MC-R1B expression include but are not limited to pYES2 (Invitrogen) and Pichia expression vector (Invitrogen).

Also, a variety of insect cell expression vectors may be used to express recombinant receptor in insect cells. Commercially available insect cell expression vectors which may be suitable for recombinant expression of MC-R1B include but are not limited to pBlueBacIII and pBlueBacHis2 (Invitrogen), and pAcG2T (Pharmingen).

Expression of MC-R1B DNA may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes, with microinjection into frog oocytes being preferred.

To determine the MC-R1B cDNA sequence(s) that yields optimal levels of MC-R1B, cDNA molecules including but not limited to the following can be constructed: a cDNA fragment containing the full-length open reading frame for MC-R1B as well as various constructs containing portions of the cDNA encoding only specific domains of the protein or rearranged domains of the protein. All constructs can be designed to contain none, all or portions of the 5' and/or 3' untranslated region of a MC-R1B cDNA. The expression levels and activity of MC-R1B can be determined following the introduction, both singly and in combination, of these constructs into appropriate host cells. Following determination of the MC-R1B cDNA cassette yielding optimal expression in transient assays, this MC-R1B cDNA construct is transferred to a variety of expression vectors (including recombinant viruses), including but not limited to those for mammalian cells, plant cells, insect cells, oocytes, bacteria, and yeast cells.

Therefore, another aspect of the present invention includes host cells that have been engineered to contain and/or express DNA sequences encoding the MC-R1B. Such recombinant host cells can be cultured under suitable conditions to produce MC-R1B or a biologically equivalent form. Recombinant host cells may be prokaryotic or eukaryotic, including but not limited to, bacteria such as *E. coli*, fungal cells such as yeast, mammalian cells including, but not limited to, cell lines of human, bovine, porcine, monkey and rodent origin, and insect cells including but not limited to Drosophila and silkworm derived cell lines. Therefore, an expression vector containing DNA encoding a MC-R1B-like protein may be used for expression of MC-R1B in a recombinant host cell. Recombinant host cells may be prokaryotic or eukaryotic, including but not limited to bacteria such as *E. coli*, fungal cells such as yeast, mammalian cells including but not limited to cell lines of human, bovine, porcine, monkey and rodent origin, and insect cells including but not limited to Drosophila- and silkworm-derived cell lines. For instance, one insect expression system utilizes *Spodoptera frugiperda* (Sf21) insect cells (Invitrogen) in tandem with a baculovirus expression vector (pAcG2T, Pharmingen). Also, mammalian species which may be suitable and which are commercially available, include but are not limited to, L cells L-M(TK$^-$) (ATCC CCL 1.3), L cells L-M (ATCC CCL 1.2), Saos-2 (ATCC HTB-85), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), MRC-5 (ATCC CCL 171), and CPAE (ATCC CCL 209). The expression vector may be introduced into host cells via any one of a number of techniques including but not limited to transformation, transfection, protoplast fusion, and electroporation. The expression vector-containing cells are individually analyzed to determine whether they produce MC-R1B protein. Identification of MC-R1B expressing cells may be done by several means, including but not limited to immunological reactivity with anti-MC-R1B antibodies, labeled ligand binding and the presence of host cell-associated MC-R1B activity.

The assays described herein as well as protein purification schemes can be carried out with cells that have been transiently or stably transfected or transformed with an expression vector which directs expression of MC-R1B. The expression vector may be introduced into host cells via any one of a number of techniques including but not limited to transformation, transfection, protoplast fusion, and electroporation. Transformation is meant to encompass a genetic change to the target cell resulting from an incorporation of DNA. Transfection is meant to include any method known in the art for introducing MC-R1B into the test cells. For example, transfection includes calcium phosphate or calcium chloride mediated transfection, lipofection, infection with a retroviral construct containing MC-R1B, and electroporation. The expression vector-containing cells are individually analyzed to determine whether they produce human MC-R1B protein. Identification of human MC-R1B expressing cells may be done by several means, including but not limited to immunological reactivity with anti-human MC-R1B antibodies, labeled ligand binding and the presence of host cell-associated human MC-R1B activity.

The specificity of binding of compounds showing affinity for MC-R1B is shown by measuring the affinity of the compounds for recombinant cells expressing the cloned receptor or for membranes from these cells. Expression of the cloned receptor and screening for compounds that bind to MC-R1B or that inhibit the binding of a known, radiolabeled ligand of MC-R1B to these cells, or membranes prepared from these cells, provides an effective method for the rapid selection of compounds with high affinity for MC-R1B. Such ligands need not necessarily be radiolabeled but can also be nonisotopic compounds that can be used to displace bound radiolabeled compounds or that can be used as activators in functional assays. Compounds identified by the above method are likely to be agonists or antagonists of MC-R1B and may be peptides, proteins, or non-proteinaceous organic molecules.

Melanocortin receptors belong to the odopsin sub-family of GPCR's. However, several features in the MC-R1B are shared with all other receptors and are absent in most other GPCR's, including the EN motif in TN1, the lack of Cys in the loop between TM2 and TM3 or between TM4 and TM5, the MxxxxxxxY motif in TM5, and the DPxxY motif in TM7. Since all melanocortin receptors lack Cys residues in the extracellular loops that are present in other members of the odopsin sub-family, interhelical disulfide bond (e.g., between the Cys residues near the top of TM3 and TM5) may play the same function as interloop disulfide bond in most other GPCR's. Accordingly, the present invention is directed to methods for screening for compounds which modulate the expression of DNA or RNA encoding a MC-R1B protein as well as compounds which effect the function of the MC-R1B protein. Methods for identifying agonists and antagonists of other receptors are well known in the art and can be adapted to identify agonists and antagonists of MC-R1B. For example, Cascieri et al. (1992, *Molec. Pharmacol*. 41:1096–1099) describe a method for identifying substances that inhibit agonist binding to rat neurokinin receptors and thus are potential agonists or antagonists of neurokinin receptors. The method involves transfecting COS cells with expression vectors containing rat neurokinin receptors, allowing the transfected cells to grow for a time sufficient to allow the neurokinin receptors to be expressed, harvesting the transfected cells and resuspending the cells in assay buffer containing a known radioactively labeled agonist of the neurokinin receptors either in the presence or the absence of the substance, and then measuring the binding of the radioactively labeled known agonist of the neurokinin receptor to the neurokinin receptor. If the amount of binding of the known agonist is less in the presence of the substance than in the absence of the substance, then the substance is a potential agonist or antagonist of the neurokinin receptor. Where binding of the substance such as an agonist or antagonist to MC-R1B is measured, such binding can be measured by employing a labeled substance or agonist. The substance or agonist can be labeled in any convenient manner known to the art, e.g., radioactively, fluorescently, enzymatically.

Therefore, the specificity of binding of compounds having affinity for MC-RLB is shown by measuring the affinity of the compounds for recombinant cells expressing the cloned receptor or for membranes from these cells. Expression of the cloned receptor and screening for compounds that bind to MC-R1B or that inhibit the binding of a known, radiolabeled ligand of MC-R1B to these cells, or membranes prepared from these cells, provides an effective method for the rapid selection of compounds with high affinity for MC-R1B. Such ligands need not necessarily be radiolabeled but can also be nonisotopic compounds that can be used to displace bound radiolabeled compounds or that can be used as activators in functional assays. Compounds identified by the above method are likely to be agonists or antagonists of MC-R1B and may be peptides, proteins, or non-proteinaceous organic molecules. Compounds may modulate by increasing or attenuating the expression of DNA or RNA encoding MC-R1B, or by acting as an agonist or antagonist of the MC-R1B receptor protein. These compounds that modulate the expression of DNA or RNA encoding MC-R1B or the biological function thereof may be detected by a variety of assays. The assay may be a simple "yes/no" assay to determine whether there is a change in expression or function. The assay may be made quantitative by comparing the expression or function of a test sample with the levels of expression or function in a standard sample. Kits containing MC-R1B, antibodies to MC-R1B, or modified MC-R1B may be prepared by known methods for such uses.

Therefore, the present invention relates to methods of expressing MC-R1B in recombinant systems and of identifying agonists and antagonists of MC-R1B. When screening compounds in order to identify potential pharmaceuticals that specifically interact with a target receptor, it is necessary to ensure that the compounds identified are as specific as possible for the target receptor. To do this, it is necessary to screen the compounds against as wide an array as possible of receptors that are similar to the target receptor. Thus, in order to find compounds that are potential pharmaceuticals that interact with receptor A, it is necessary not only to ensure that the compounds interact with receptor A (the "plus target") and produce the desired pharmacological effect through receptor A, it is also necessary to determine that the compounds do not interact with receptors B, C, D, etc. (the "minus targets"). In general, as part of a screening program, it is important to have as many minus targets as possible (see Hodgson, 1992, *Bio/Technology* 10:973–980, @ 980). MC-R1B proteins and the DNA molecules encoding this receptor protein have the additional utility in that they can be used as "minus targets" in screens designed to identify compounds that specifically interact with other G-protein coupled receptors. Due to homology to GPCRs, the MC-R1B of this invention is believed to function similarly to GPCRs and have similar biological activity. They are useful in understanding the biological and physiological effects and study to melanocortin active compounds in primates, followed by human clinical trials. More notable, MC-R1B agonists will be identified and evaluated for their effects on food intake, weight gain, and metabolic rate to identify novel-anti-obesity agents that are effective in primates. They may also be used to scan for monkey melanocortin agonists and antagonists; as in particular to test the specificity of identified ligands.

To this end, the present invention relates in part to methods of identifying a substance which modulates MC-R1B receptor activity, which involves:

(a) combining a test substance in the presence and absence of a MC-R1B receptor protein, including but not limited to the MC-R1B proteins comprising the amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:17, SEQ ID NO:20, SEQ ID NO:23, and SEQ ID NO:26; and, (b) measuring and comparing the effect of the test substance in the presence and absence of the MC-R1B receptor protein.

In addition, several specific embodiments are disclosed herein to show the diverse type of screening or selection assay which the skilled artisan may utilize in tandem with an expression vector directing the expression of the MC-R1B receptor protein. Methods for identifying agonists and antagonists of other receptors are well known in the art and can be adapted to identify agonists and antagonists of MC-R1B. Therefore, these embodiments are presented as examples and not as limitations. To this end, the present invention includes assays by which MC-R1B modulators (such as agonists and antagonists) may be identified. Accordingly, the present invention includes a method for determining whether a substance is a potential agonist or antagonist of MC-R1B that comprises:

(a) transfecting or transforming cells with an expression vector that directs expression of MC-R1B in the cells, resulting in test cells;

(b) allowing the test cells to grow for a time sufficient to allow MC-R1B to be expressed;

(c) exposing the cells to a labeled ligand of MC-R1B in the presence and in the absence of the substance;

(d) measuring the binding of the labeled ligand to MC-R1B; where if the amount of binding of the labeled ligand is less in the presence of the substance than in the absence of the substance, then the substance is a potential agonist or antagonist of MC-R1B.

The conditions under which step (c) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. The test cells may be harvested and resuspended in the presence of the substance and the labeled ligand. In a modification of the above-described method, step (c) is modified in that the cells are not harvested and resuspended but rather the radioactively labeled known agonist and the substance are contacted with the cells while the cells are attached to a substratum, e.g., tissue culture plates.

The present invention also includes a method for determining whether a substance is capable of binding to MC-R1B, i.e., whether the substance is a potential agonist or an antagonist of MC-R1B, where the method comprises:

(a) transfecting or transforming cells with an expression vector that directs the expression of MC-R1B in the cells, resulting in test cells;

(b) exposing the test cells to the substance;

(c) measuring the amount of binding of the substance to MC-R1B;

(d) comparing the amount of binding of the substance to MC-R1B in the test cells with the amount of binding of the substance to control cells that have not been transfected with MC-R1B;

wherein if the amount of binding of the substance is greater in the test cells as compared to the control cells, the substance is capable of binding to MC-R1B. Determining whether the substance is actually an agonist or antagonist can then be accomplished by the use of functional assays such as, e.g., the assay involving the use of promiscuous G-proteins described below.

The conditions under which step (b) of the method is practiced are conditions that are typically used in the art for the study of protein-ligand interactions: e.g., physiological pH; salt conditions such as those represented by such commonly used buffers as PBS or in tissue culture media; a temperature of about 4° C. to about 55° C. The test cells are harvested and resuspended in the presence of the substance.

Chen et al. (1995, *Analytical Biochemistry* 226: 349–354) describe a colorometric assay which utilizes a recombinant cell transfected with an expression vector encoding a G-protein coupled receptor with a second expression vector containing a promoter with a cAMP responsive element fused to the LacZ gene. Activity of the overexpressed G-protein coupled receptor is measured as the expression and OD measurement of β-Gal. Therefore, another aspect of this portion of the invention includes a non-radioactive method for determining whether a substance is a potential agonist or antagonist of MC-R1B that comprises:

(a) transfecting or transforming cells with an expression vector encoding MC-R1B, resulting in test cells;

(b) transfecting or transforming the test cells of step (a) with an expression vector which comprises a cAMP-inducible promoter fused to a colorometric gene such a LacZ;

(c) allowing the transfected cells to grow for a time sufficient to allow MC-R1B to be expressed;

(d) harvesting the transfected cells and resuspending the cells in the presence of a known agonist of MC-R1B and/or in both the presence and absence of the test compound;

(e) measuring the binding of the known agonist and test compound to overexpressed MC-R1B by a coloromet-ric assay which measures expression off the cAMP-inducible promoter and comparing expression levels in the presence of the known agonist as well as in the presence and absence of the unknown substance so as to determine whether the unknown substance acts as either a potential agonist or antagonist of MC-R1B.

Additional methods of identifying agonists or antagonists include but are by no means limited to the following:

I. (a) transfecting or transforming cells with a first expression vector which directs expression of MC-R1B and a second expression vector which directs the expression of a promiscuous G-protein, resulting in test cells;

(b) exposing the test cells to a substance that is a suspected agonist of MC-R1B;

(c) measuring the level of inositol phosphates in the cells;

where an increase in the level of inositol phosphates in the cells as compared to the level of inositol phosphates in the cells in the absence of the suspected agonist indicates that the substance is an agonist of MC-R1B.

II. (a) transfecting or transforming cells with a first expression vector which directs expression of MC-R1B and a second expression vector which directs the expression of a promiscuous G-protein, resulting in test cells;

(b) exposing the test cells to a substance that is an agonist of MC-R1B;

(c) subsequently or concurrently to step (b), exposing the test cells to a substance that is a suspected antagonist of MC-R1B;

(d) measuring the level of inositol phosphates in the cells;

where a decrease in the level of inositol phosphates in the cells in the presence of the suspected antagonist as compared to the level of inositol phosphates in the cells in the absence of the suspected antagonist indicates that the substance is an antagonist of MC-R1B.

III. the method of II wherein the first and second expression vectors of step (a) are replaced with a single expression vector which expresses a chimeric MC-R1B protein fused at its C-terminus to a promiscuous G-protein.

The above-described methods can be modified in that, rather than exposing the test cells to the substance, membranes can be prepared from the test cells and those membranes can be exposed to the substance. Such a modification utilizing membranes rather than cells is well known in the art and is described in, e.g., Hess et al., 1992, *Biochem. Biophys. Res. Comm.* 184:260–268. Accordingly, another embodiment of the present invention includes a method for determining whether a substance binds and/or is a potential agonist or antagonist of MC-R1B wherein membrane preparations from the test cells are utilized in place of the test cells. Such methods comprise the following and may utilized the physiological conditions as noted above:

(a) transfecting or transforming cells with an expression vector that directs the expression of MC-R1B in the cells, resulting in test cells;

(b) preparing membranes containing MC-R1B from the test cells and exposing the membranes to a ligand of MC-R1B under conditions such that the ligand binds to the MC-R1B in the membranes;

(c) subsequently or concurrently to step (b), exposing the membranes from the test cells to a substance;

(d) measuring the amount of binding of the ligand to the MC-R1B in the membranes in the presence and the absence of the substance;

(e) comparing the amount of binding of the ligand to MC-R1B in the membranes in the presence and the absence of the substance where a decrease in the amount of binding of the ligand to MC-R1B in the membranes in the presence of the substance indicates that the substance is capable of binding to MC-R1B.

The present invention also relates to a method for determining whether a substance is capable of binding to MC-R1B comprising:

(a) transfecting or transforming cells with an expression vector that directs the expression of MC-R1B in the cells, resulting in test cells;

(b) preparing membranes containing MC-R1B from the test cells and exposing the membranes from the test cells to the substance;

(c) measuring the amount of binding of the substance to the MC-R1B in the membranes from the test cells;

(d) comparing the amount of binding of the substance to MC-R1B in the membranes from the test cells with the amount of binding of the substance to membranes from control cells that have not been transfected with MC-R1B, where if the amount of binding of the substance to MC-R1B in the membranes from the test cells is greater than the amount of binding of the substance to the membranes from the control cells, then the substance is capable of binding to MC-R1B.

A preferred embodiment of the present invention is determining various ligand binding affinities using $^{125}$I-labeled NDP-α-MSH as the labeled ligand in the presence of varying concentration of unlabeled ligands. The activation of the second messenger pathway may be determined by measuring the intracellular cAMP elicited by agonist at various concentration.

The present invention also relates to polyclonal and monoclonal antibodies raised in response to either the form of MC-R1B, or a biologically active fragment thereof. Polyclonal or monoclonal antibodies may be raised against MC-R1B or a synthetic peptide (usually from about 9 to about 25 amino acids in length) from a portion of MC-R1B, for instance as disclosed in SEQ ID NO:2, SEQ ID NO:4, SEQ ID NO:6, SEQ ID NO:8, SEQ ID NO:10, SEQ ID NO:12, SEQ ID NO:14, SEQ ID NO:17, SEQ ID NO:20, SEQ ID NO:23, and SEQ ID NO:26. Monospecific antibodies to MC-R1B are purified from mammalian antisera containing antibodies reactive against MC-R1B or are prepared as monoclonal antibodies reactive with MC-R1B using the technique of Kohler and Milstein (1975, *Nature* 256: 495–497). Monospecific antibody as used herein is defined as a single antibody species or multiple antibody species with homogenous binding characteristics for MC-R1B. Homogenous binding as used herein refers to the ability of the antibody species to bind to a specific antigen or epitope, such as those associated with MC-R1B, as described above. MC-R1B-specific antibodies are raised by immunizing animals such as mice, rats, guinea pigs, rabbits, goats, horses and the like, with an appropriate concentration of MC-R1B protein or a synthetic peptide generated from a portion of MC-R1B with or without an immune adjuvant.

Preimmune serum is collected prior to the first immunization. Each animal receives between about 0.1 mg and about 1000 mg of MC-R1B protein associated with an acceptable immune adjuvant. Such acceptable adjuvants include, but are not limited to, Freund's complete, Freund's incomplete, alum-precipitate, water in oil emulsion containing *Corynebacterium parvum* and tRNA. The initial immunization consists of MC-R1B protein or peptide fragment thereof in, preferably, Freund's complete adjuvant at multiple sites either subcutaneously (SC), intraperitoneally (IP) or both. Each animal is bled at regular intervals, preferably weekly, to determine antibody titer. The animals may or may not receive booster injections following the initial immunization. Those animals receiving booster injections are generally given an equal amount of MC-R1B in Freund's incomplete adjuvant by the same route. Booster injections are given at about three week intervals until maximal titers are obtained. At about 7 days after each booster immunization or about weekly after a single immunization, the animals are bled, the serum collected, and aliquots are stored at about −20° C.

Monoclonal antibodies (mAb) reactive with MC-R1B are prepared by immunizing inbred mice, preferably Balb/c, with MC-R1B protein. The mice are immunized by the IP or SC route with about 1 mg to about 100 mg, preferably about 10 mg, of MC-R1B protein in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 1 to about 100 mg of MC-R1B in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/NS1/Ag 4-1; MPC-11; S-194 and Sp 2/0, with Sp 2/0 being preferred. The antibody producing cells and myeloma cells are fused in polyethylene glycol, about 1000 mol. wt., at concentrations from about 30% to about 50%. Fused hybridoma cells are selected by growth in hypoxanthine, thyrnidine and aminopterin supplemented Dulbecco's Modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using MC-R1B as the antigen. The culture fluids are also tested in the Ouchterlony precipitation assay to determine the isotype of the mAb. Hybridoma cells from antibody positive wells are cloned by a technique such as the soft agar technique of MacPherson, 1973, Soft Agar Techniques, in *Tissue Culture Methods and Applications*, Kruse and Paterson, Eds., Academic Press.

Monoclonal antibodies are produced in vivo by injection of pristine primed Balb/c mice, approximately 0.5 ml per mouse, with about $2\times10^6$ to about $6\times10^6$ hybridoma cells about 4 days after priming. Ascites fluid is collected at approximately 8–12 days after cell transfer and the monoclonal antibodies are purified by techniques known in the art.

In vitro production of anti-MC-R1B mAb is carried out by growing the hybridoma in DMEM containing about 2% fetal calf serum to obtain sufficient quantities of the specific mAb. The mAb are purified by techniques known in the art.

Antibody titers of ascites or hybridoma culture fluids are determined by various serological or immunological assays which include, but are not limited to, precipitation, passive agglutination, enzyme-linked immunosorbent antibody (ELISA) technique and radioimmunoassay RIA techniques. Similar assays are used to detect the presence of MC-R1B in body fluids or tissue and cell extracts.

It is readily apparent to those skilled in the art that the above described methods for producing monospecific antibodies may be utilized to produce antibodies specific for MC-R1B peptide fragments, or full-length MC-R1B.

MC-R1B antibody affinity columns are made, for example, by adding the antibodies to Affigel-10 (Biorad), a gel support which is pre-activated with N-hydroxysuccinimide esters such that the antibodies form covalent linkages with the agarose gel bead support. The antibodies are then coupled to the gel via amide bonds with the spacer arm. The remaining activated esters are then quenched with 1 M ethanolamine HCl (pH 8). The column is washed with water followed by 0.23 M glycine HCl (pH 2.6) to remove any non-conjugated antibody or extraneous protein. The column is then equilibrated in phosphate buffered saline (pH 7.3) and the cell culture supernatants or cell extracts containing full-length MC-R1B or MC-R1B protein fragments are slowly passed through the column. The column is then washed with phosphate buffered saline until the optical density ($A_{280}$) falls to background, then the protein is eluted with 0.23 M glycine-HCl (pH 2.6). The purified MC-R1B protein is then dialyzed against phosphate buffered saline.

The DNA molecules, RNA molecules, recombinant protein and antibodies of the present invention may be used to screen and measure levels of MC-R1B. The recombinant proteins, DNA molecules, RNA molecules and antibodies lend themselves to the formulation of kits suitable for the detection and typing of MC-R1B. Such a kit would comprise a compartmentalized carrier suitable to hold in close confinement at least one container. The carrier would further comprise reagents such as recombinant MC-R1B or anti-MC-R1B antibodies suitable for detecting MC-R1B. The carrier may also contain a means for detection such as labeled antigen or enzyme substrates or the like.

Pharmaceutically useful compositions comprising modulators of MC-R1B may be formulated according to known methods such as by the admixture of a pharmaceutically acceptable carrier. Examples of such carriers and methods of formulation may be found in Remington's Pharmaceutical Sciences. To form a pharmaceutically acceptable composition suitable for effective administration, such compositions will contain an effective amount of the protein, DNA, RNA, modified MC-R1B, or either MC-R1B agonists or antagonists including tyrosine kinase activators or inhibitors.

Therapeutic or diagnostic compositions of the invention are administered to an individual in amounts sufficient to treat or diagnose disorders. The effective amount may vary according to a variety of factors such as the individual's condition, weight, sex and age. Other factors include the mode of administration.

The pharmaceutical compositions may be provided to the individual by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages. Alternatively, co-administration or sequential administration of other agents may be desirable.

The present invention also has the objective of providing suitable topical, oral, systemic and parenteral pharmaceutical formulations for use in the novel methods of treatment of the present invention. The compositions containing compounds identified according to this invention as the active ingredient can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the present invention is selected in accordance with a variety of factors including type, species, age, weight, sex and medical condition of the patient; the severity of the condition to be treated; the route of administration; the renal, hepatic and cardiovascular function of the patient; and the particular compound thereof employed. A physician or veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

The following examples are provided to illustrate the present invention without, however, limiting the same hereto.

EXAMPLE 1

Isolation and Characterization of Human MC-1R Splice Variants

Expressed Sequence Tag (EST) Identification—Genbank databases were monitored using the Tblastn search program (Altschul et al., 1990, *J. Mol. Biol.* 215:403–410) with amino acid sequence from human melanocortin receptor proteins. A human EST (GenBank accession #AI123000; dbEST Id #1881544; GenBank gi: 3538766; Clone Id: Image:1509887 (3') deposited Aug. 18, 1997) derived from five normalized and pooled cDNA libraries was identified with a significant homology score. EST AI123000 exhibited sequence identity (>90% at the DNA level) to the 3' end of the gene for the human MC-1R. The nucleotide sequence of EST AA123000 is as follows:

```
TTTTTGATGC TGAGTCACAT TTATTACCAG ACTTTCCTGG CCCCATGCTC ACAGGCACTG

GTCACTGAGT CAGGCATTTG CACGGGCTGT CTGCTTGGGC GACTGCTGCA GGAAAGCAGG

CTGAGGCCCA GTGCCCAGTC TGAGCCTTAG AACCGGCCCT CAGGAGGGTC CAGCCTCACA

CCACTAGGGG GGCTCCTGCA AACCTGGTCC CTTGGCCTGA GGAGGGATTT CACCTCCTTT

TGCAGGAGCC GCTGCAAGGC TGTTGGATGA AGCTTTCTGG TCACAAAGCC CCTTCTCCTG

GGGCTGCTGT GGGAGTAGCT CTTGGCACAC ACTTCCACCC AGAGACTTCA CATCCCAGCT

GACGAGGGCA CGGTCCTGAG AGCAGGAGCA CGTCAGCACC TCCTTGAGCG TCCTGCGACG

TCCTGGCTGT GGAAGGCGTA GATGAGGGGG TCGATGATGG CATTGCAGAT GATGAGGGCG

AGAAAGAGGT TGAAAGTTCT TGAAGATGCA GCCGACGTGG GGTGCTCGGG GCAGAGGACG

ATGAGTGTGA GATGCAGGAA GAGGGGCCC CAGCAGAGGA GAAATTGCCA ACAGGATTGG

TGANGGTGAA GCNGCTTTTA AGCCANAGCC CT (SEQ ID NO:28).
```

An additional EST was subsequently deposited on Oct. 13, 1998 with similar sequence identity to the 3' end of the human MC-R1 gene. The GenBank accession number of this EST is #AI187892 (dbEST Id #826102; GenBank gi: 1774101; Clone Id: Image:625984 (3')). The nucleotide sequence of EST AA187892 is as follows:

this EST may represent a portion of an alternatively spliced form of the human MC-R1 gene, disclosed throughout this specification as an MC-R1B protein, containing 382 amino acids. The previously described MC-R1 protein containing 317 amino acids is referred to as MC-R1A (Mountjoy, et al., 1992, Science 257:1248–1251 [see also U.S. Pat. No. 5,532,

```
AACAAACTTT GGTAAGTAGT GAATGGCAAA GGCTCAGGGG GTTTGCAGCA GGACCTCCTT

GGGGTCAGAT CTGCCAGCCT CGGGTTGNCT TTCAGACCCC TCATCGTCTA TGAGGCATCC

TGTAAGTGCA GCTGTGGCCA GGGCTTGCAT ATGCAATCAA TTCCTGATTC ACCTAGTTCT

TGGCAGGAAG AGAAAATACT CGTTAATCAG AGGACTAAAC AATCCAAAAG CGCATTCTCT

CTCTGGGAAT GGAATATAAT TTATATTTCT GTTGCTATTG AATTATCCTT CTAATTCCAC

TGGACTAAAC TTAATACCAG TAATACTAAA ATTTTGTTTT GGGCAAAGCG ACTTGAAGGA

GGAGTCAGTG GCGCACTAAT NGCTGACTGT GAAAAATAAA CACCTCTGAG ATCAAGAATC

CCACAGTGAG AGCTAGGATT TGAAGGTATC CAGAGATTGC AAAACTCTGT GACTAACAGC

AANTTTTTAA CCAGGGCAAA CCAAACCACT CCTACTTGGA CTTAAACCTC AATCATTTAG

ATTTCATTCC C (SEQ ID NO:29).
```

Additional searching of the dbEST subset of Genbank identified two other human ESTs with sequence identity to the human MC-R1R: The first is available under GenBank accession number #AA431397 and was isolated from human testis mRNA and entered on May 22, 1997 (dbEST Id #1075968; GenBank gi: 2115105; Clone Id: Image:782133 (5')). The nucleotide sequence of EST AA431397 is as follows:

347]; Chhajlani and Wikberg, 1992, FEBS Letters 309:417–420). FIG. 1 shows alignment of these ESTs in relation to the MC-R1A and MC-R1B genes.

Cloning of the MC-R Spliced Variant MC-R1B) From Human Genomic DNA—Touchdown PCR was performed with sheared human genomic DNA (0.5 mg; Clontech, Palo Alto, Calif.) in a GeneAmp 9700 PCR system (Perkin Elmer, Foster City, Calif.). Two sense primers, MC1R-5' for 1 (5'

```
AAATGATCTC TGAAAGTGTT GAAGCGCGGA CCCTTCTGGG TCCCGGAGGG GTCCCTGCAA

AACTCCAGGC AGGACTTCTC ACCAGCAGTC GTGGGGAACC GAGGAGGACA TGGGGAGGTT

GTGGGGCCTC AGGCTCCGGG CACCAGGGGC CAACCTCAGG CTCCTAAAGA GACATTTTCC

GCCCACATCC TGGGACACTC CGTCTGCTCC AATGACTGAG CAGCATCCAC CCCACCCCAT

CTTTGCTGCC AGCTCTCAGG ACCGTGCGCT CGTCAGCTGG GATGTGAAGT CTCTGGGTGG

AAGTGTGTGC CAAGAGCTAC TCTCACAGCA GCCCCAGGAG AAGGGGCTTT GTGAC
(SEQ ID NO:30).
```

Another EST is available under GenBank accession number #AA778295 and was isolated from human fetal heart mRNA and was entered into the database on Feb. 5, 1998 (dbEST Id #1075968; GenBank gi: 2115105; Clone Id: Image:782133 (5')). The nucleotide sequence of EST AA431397 is as follows:

TCTCACACTCATCGTCCTCTGCCC3'; SEQ ID NO:32) and MC1R-5' for 2 (5' CATCGCCTACTACGAC-CACGTGGC3'; SEQ ID NO:33), were designed based on the published sequence of human MC-1RA (id). The antisense primers, MC1R-3' rev1 (5'CGCTGCAAGGCTGTTGGATGAAGC3'; SEQ ID

```
CGGGTGATGC TGAGTCACAT TTATTACCAG ACTTTCCTGG CCCCATGCTC ACAGGCACTG

GTCACTGAGT CAGGCATTTG CCAGGGCTGT CTGCTTGGGC GACTGCTGCA TGAAAGCAGG

CTGAGGCCCC AGTGCCCAGT CTGAGCCTTA GAACCGGCCC TCAGGAGGGC TCAGCCCTAT

ACCACTAGGG GGGCTCCTGC AAACCTGGTC CCTTGGCCTG AGGCAGGGAT TTCACCTCCT

TTTGCAGGAG CCGCTGCAAG GCT (SEQ ID NO:31).
```

DNA sequencing of both strands using dye terminator cycle sequencing ready reactions (Perkin Elmer-ABI), analyzed on a 377 ABI Prism cycle sequencer suggested that NO:34) and MC1R-3' rev2 (5' GTGGGAGTAGCTCTTG-GCACACAC; SEQ ID NO:35) were derived from EST AI123000. An Advantage cDNA PCR kit (Clontech, Palo Alto, Calif.) was used in the PCR reactions essentially following the manufacturer's instructions. Two exceptions were the addition of 5% DMSO to the PCR reactions and PCR cycling as described below: 1) 94° C. for 1 minute, 2) 5 cycles of 94° C. for 30 seconds, 72° C. for 3 minutes, 3) 5 cycles of 94° C. for 30 seconds, 70° C. for 3 minutes, 4) 20 cycles of for 30 seconds, 68° C. for 3 minutes. Subsequent sequencing of the PCR products using BIG DYE terminator cycle sequencing Ready Reactions (Perkin Elmer, Foster City, Calif.) and analysis on a 377 ABI Prism cycle sequencer (Perkin Elmer, Foster City, Calif.) revealed the presence of a cryptic 381 bp intron immediately upstream (at the C-terminal Trp-317 residue) of the TGA stop codon of the human MC-R1 gene. The nucleotide boundaries describing this intron using consensus splice junction sequences as a guide (Senapathy et al., 1990, *Meth. Enzymol.* 183: 252–278) are as follows. A conserved consensus splice donor site (A/C)AG/gt (nucleotides 950–952) was found which form the first two bases of the Trp triplet codon.

Figure 2:
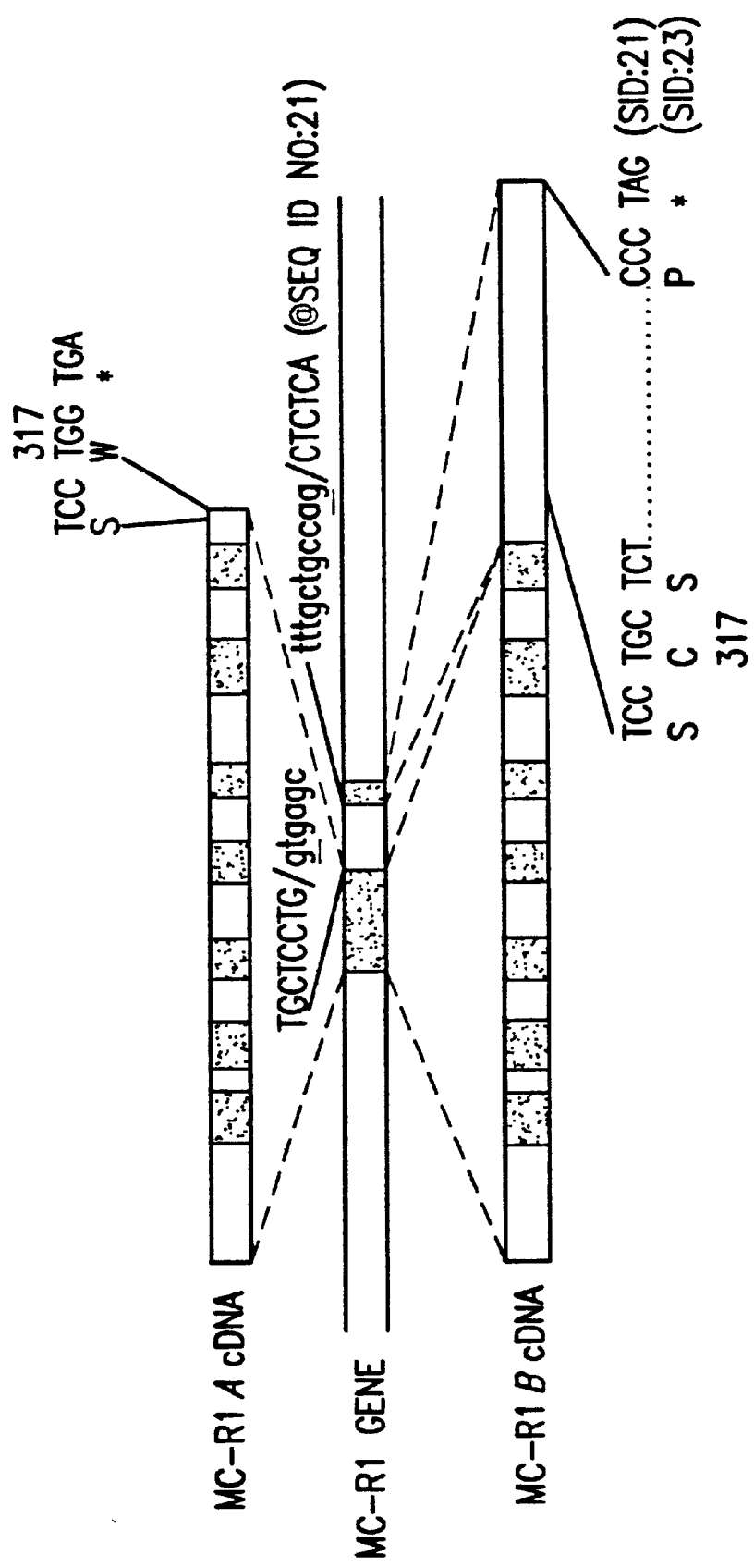
FIG. 2 shows the alternative splicing of the human MC-R1 gene. The MC-R1A cDNA is as known in the art. The MC-R1 gene intron junctions are as shown, for example, in SEQ ID NO:21 (mc1-8). The MC-R1B cDNA shows the additional exon at the 3' end of the gene, which encodes a 65 amino acid extension, beginning with the Ser residue at amino acid 318. MC-R1A contains a Trp-317 residue while MC-R1B contains a Cys-317 residue. The dark boxes for MC-R1A and MC-R1B represent portions of the cDNA which encode transmembrane domains, while the dark boxes of the MC-R1 gene represent the two exons which encode for the MCR1B protein(s).

FIG. 2 shows the alternative splicing of the two human forms of MC-R1, with the COOH-terminal regions of expressed protein shown as well as the splice junctions identified in the various genomic clones encoding human MC-R1B.

FIG. 3 shows a representative genomic clone for human MC-R1B, the DNA sequence of the genomic clone, mc1-8 (SEQ ID NO:21). Large cap letters represent exon regions while small cap nucleotides represent the single intron of the MC-R1 gene. A conserved consensus splice acceptor site cag/R was identified at nucleotides 1330–1332. Formation of this splice junction results from the donor supplying TG and the acceptor supplying C to form the triplet codon for Cys (instead of the C-terminal amino Trp of the MC-R1A). The novel coding sequence giving rise to an additional 65 amino acids (not including the Trp-317 to Cys substitution) occurs as result of this splicing event.

FIGS. 4A–4B show the nucleotide and amino acid sequence of the amino terminal portion of MC-R1A and MC-R1B forms of mc1-8, the 5' and 3' splice junction sequences, as well as the respective amino acid sequences of the carboxy terminal portions of MC-R1A and MC-R1B.

Overlapping PCR was then performed to generate a contiguous open reading frame (382 amino acids) devoid of the intron containing this novel carboxyl terminus. PCR products for exons I and II were produced each containing a small portion of the other exon. The primers for exon I were as follows:

1. mc1-like-1f (5' gggcccgaattcgccgccATGGCTGTG-CAGGGATCCCAGAG3'; SEQ ID NO:36); and,
2. mc1-like-1r (5' GGCACGGTCCTGAGAGCAGGAG-CATGTCAGCACCTCCTTG3'; SEQ ID NO:37), and contained an EcoRI site and a Kozak sequence (GCC GCC) for optimum translation. The primers for exonII were as follows:
1. mc1-like-2f (5' CTGACATGCTCCTGCTCTCAGGAC-CGTGCCCTCGTCAGC3'; SEQ ID NO:38); and,
2. mc1-like-2r (5' agtttagcggccgcCTAGGGGGGCTCCT-GCAAACCTGG3'; SEQ ID NO:39), which contains a NotI site. The MC1-like open reading frame was then generated from exon I and II templates and primers mc1-like 1f and MC1-like 2r. The MC1-like ORF fragment was digested with EcoRI and NotI, gel-purified, ligated into pcDNA3 vector and transformed into SCSI *E. coli* (Stratagene, La Jolla, Calif.). Each of the four exemplified genomic clones (mc1-3, mc1-6, mc1-8 and mc1-9) were isolated using the above disclosed methodology. ps Cloning of the MC-R Spliced Variant (MC-R1B) From Human Testes mRNA—Full-length cDNA encoding MC-R1B was isolated from human testis poly $(A)^+$ mRNA (pool of 25 male caucasians). RT-PCR using 1 mg of testis mRNA was performed using the Advantage RT for PCR kit with MMLV reverse transcriptase (Clontech, Palo Alto, Calif.) essentially following the manufacturer's instructions. PCR was then conducted with the Advantage cDNA PCR kit (Clontech, Palo Alto, Calif.) essentially following the manufacturer's instructions (cycling conditions: 94° C. for 1 min., 60° C. for 2 min., 72° C. for 2 min., 72° C. for 10 min. The forward sense primer utilized (appending EcoRI restriction site and optimized initiation sequence based on Kozak rules) was (5' GATCGAAT-TCGCCGCCATGGCTGTGCAGGGATCCCA-GAGAAG3'; SEQ ID NO:40) while the reverse antisense primers were (5' GATCGAATTCCTAGGGGGGCTCCTG-CAAACCTG3'; SEQ ID NO:41) or (5' GATCGAATTCGT-GCCCAGTCTGAGCCTTAGAACCG3': SEQ ID NO:42). Amplified products were agarose gel-purified, digested with EcoRI and ligated to the mammalian expression vector pcDNA-3.1 (−)(Invitrogen). This methodology was utilized to identify the MC-R1ESTc11, as well as the other cDNA clones,

EXAMPLE 2

Transient Expression of Human MC-R1B

Four 800 ml triple flasks (Nalge Nunc) containing 125 ml of Dulbecco's modified Eagle Medium (DMEM), (Gibco-BRL) supplemented with 10% fetal bovine serum (Sigma), L-glutamine (Gibco/BRL), and Pen/Strep (Gibco/BRL) were inoculated with COS 7 cells, and incubated for 4 days. The cells in each flask were collected by pouring off the media, adding 30 ml of trypsin/EDTA (0.05%, Gibco/BRL) to each flask and letting the flasks incubate at room temp for 2 min. Then the tyrpsin solution was removed, and the flasks incubated at 37° C. for 10 minutes, 30 ml of DMEM added, and the cells collected. The cells were pelleted at 1000 rpm for 8 min., washed twice with Delbecco's PBS lacking $Mg^{++}$ and $Ca^{++}$ (Gibco/BRL). The cells were counted and resuspended to a density of $1.2 \times 10^7$/ml of PBS lacking $Mg^{++}$ and $Ca^{++}$. DNA was introduced into the cells by electroporation; 0.85 ml of cells was mixed with 20 μg of MC-R1 expression plasmid, in an ice cold 0.4 cm cuvette (BioRad). The solution was electroporated with a BioRad Gene Pulsar electroporator set to 0.26 kV, 960 μFD. The cells from 30 electroporations were pooled into 1 liter of DMEM and dispensed 125 ml per triple flask and incubated at 37° C. Three days later the media from each flask was poured off, the cells were washed with 100 ml of Delbecco's PBS lacking $Mg^{++}$ and $Ca^{++}$, and 30 ml of enzyme-free dissociation buffer (Gibco/BRL) added. After incubation at room temperature for 10 min., cells were collected, centrifuged at 1000 rpm for 10 min. at 4° C., and resuspended into 15 ml of membrane buffer (10 mM Tris pH 7.4, with proteinase inhibitors). A 500×proteinase inhibitor solution contains Leupeptin (Sigma) 2 μg/ml, Phosphoramidon (Sigma) 5 μM, Bacitracin (Sigma) 20 μg/ml, Aprotinin (Sigma) 2.5 μg/ml, and 0.05 M AEBSF (Pefabloc). Cells are disrupted with 10 strokes of a motor driven dounce, the homogenate transferred to 50 ml Falcon tubes and spun at 2200 rpm, 4° C. for 10 min. The supernatant was transferred to 50 ml centrifuge tubes and spun at 18K for 20 min. in a Sorvall RC5B centrifuge. The membranes were resuspended into 0.6 ml of membrane buffer, passed 2 times through a 18 gauge needle and 5 times through a 25 gauge needle, aliquoted, frozen in liquid nitrogen, and stored at −80° C. until needed.

EXAMPLE 3

Pharmacological Properties of Human MC-R1B

Melanocortin Radioligand Binding Assay—Binding reactions (total volume=250 μl) contained MBB (50 mM Tris pH 7.2, 2 mM CaCl$_2$, 1 MM MgCl$_2$), 0.1% BSA, crude membranes prepared from cells expressing human MC-R1B receptor, 200 pM [$^{125}$I]-NDP αMSH (Amersham Corp.), and increasing concentrations of unlabelled test compounds dissolved in DMSO (DMSO final concentration=2%). Reactions were incubated for 1 hour without shaking and then filtered through 96-well filter plates (Packard Corp.). Filters were washed three times with TNE buffer (50 mM Tris pH 7.4, 5 mM EDTA, 150 mM NaCl), dried and counted using Microscint-20 in a Topcount scintillation counter (Packard). Inhibitory concentration 50% (IC$_{50}$ given in nM) is defined as the concentration of unlabeled melanocortin peptides which displaces 50% of the binding to the MC-1R expressing cell membranes. Non-specific binding was determined in the presence of 2 μM unlabelled NDP αMSH (Peninsula laboratories). COS-7 cells transiently expressing MC-R1B bound [$^{125}$I]-NDP-αMSH with high affinity and specificity (specific binding, defined as the difference in binding observed in the absence and presence of 1 μM unlabeled NDP-αMSH was >90% of total binding). Little, or no specific binding was observed in sham-transfected COS-7 cells. As shown below in Table 1, several melanocortin-derived peptides (amino acid sequence defined below in single letter IUPAC code) displaced the binding of [$^{125}$I]-NDP-αMSH potently indicating the presence of a high affinity binding site conferred by MC-1RB expression.

TABLE 1

| Peptide | IC$_{50}$ (nM) |
| --- | --- |
| αMSH | 5 |
| γMSH | 5 |
| NDP-αMSH | 0.7 |
| SHU-9119 | 0.7 |
| MT-II | 0.2 |
| ACTH | 5 | cAMP Functional Receptor Assay—Receptor-mediated stimulation of cyclic AMP (cAMP) formation was assayed in COS-7 cells transfected with MC-1RB expression plasmids. Cells expressing MC-1RB were dissociated from tissue culture flasks by rinsing with Ca and Mg free phosphate buffered saline (Life Technologies, Gaithersburg, Md.) and detached following 5 min. incubation with enzyme-free dissociation buffer (Specialty Media, Lavellette, N.J.). Cells were collected by centrifugation and resuspended in Earle's Balanced Salt Solution (EBSS) (Life Technologies, Gaithersburg, Md.) with additions of 10 mM HEPES pH 7.5, 5 mM MgCl$_2$, 1 mM glutamine and 1 mg/ml bovine serum albumin. Cells are counted and diluted to 2 to 4×10$^6$/ml. The phosphodiesterace inhibitor 3-isobutyl-1-methylxanthine was added at a concentration of 0.6 mM. Test peptides were diluted in EBSS with above additions and 10% DMSO; 0.1 vol of compounds added to 0.9 vol of cells. After room temperature incubation for 40 min., cells are lysed by incubation at 100° C. for 5 min. to release accumulated cAMP. cAMP is measured in an aliquot of the cell lysate with the Amersham (Arlington Heights, Ill.) cAMP detection assay (RPA556). The amount of cAMP production which results from an unknown compound is compared to that amount of cAMP produced in response to αMSH which is defined as a 100% agonist.

Previous studies (Mountjoy, et al., 1992, *Science* 257:1248–1251 [see also U.S. Pat. No. 5,532,347]; Chhajlani and Wikberg, 1992, *FEBS Letters* 309:417–420) has documented that activation of the MC-1RA isoform by melanocortin agonists results in an elevation of intracellular cAMP production through the coupling of G-proteins to activation of membrane-bound adenylate cyclase. Expression of MC-R1B protein transiently in COS-7 also gives a rise (~3-fold at maximum agonist concentration compared to background response measured in sham-transfected COS-7 cells) in intracellular cAMP formation specifically evoked by several melanocortin agonists or mixed agonists/antagonists including αMSH, MT-II, SHU-9119, γMSH, NDP-αmsh, and βMSH. This result indicates that MC-R1B cDNA encodes a functional receptor for melanocortins. The approximate rack order of potency of the above peptides in eliciting the cAMP response was MT-II>NDP-MSH>SHU-9119>αMSH>βMSH>γMSH.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A purified nucleic acid molecule encoding a human melanocortin 1 receptor protein, wherein the human melanocortin-1 receptor protein comprises a carboxy terminal region having an amino acid sequence as set forth in SEQ ID NO:27.

2. A purified nucleic acid molecule of claim 1 wherein the nucleic acid molecule is selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:16, SEQ ID NO:18; SEQ ID NO:19, SEQ ID NO:21, SEQ ID NO:22, SEQ ID NO:24, and SEQ ID NO:25.

3. A purified nucleic acid molecule encoding human MC-R1B protein wherein the nucleic acid molecule encodes a protein comprising an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:17, SEQ ID NO:20, SEQ ID NO:23, and SEQ ID NO:26.

4. An expression vector for the expression of a human MC-R1B protein in a recombinant host cell wherein the expression vector comprises a DNA molecule which encodes the amino acid sequence of claim 1.

5. An expression vector of claim 4 which is a eukaryotic expression vector.

6. An expression vector of claim 4 which is a prokaryotic expression vector.

7. A host cell which expresses a recombinant human MC-R1B protein wherein said host cell contains the expression vector of claim 4.

8. A host cell which expresses a recombinant human MC-R1B protein wherein said host cell contains the expression vector of claim 5.

9. A host cell which expresses a recombinant human MC-R1B protein wherein said host cell contains the expression vector of claim 6.

10. A host cell of claim 7 wherein said human MC-R1B protein is overexpressed from said expression vector.

11. A host cell of claim 8 wherein said human MC-R1B protein is overexpressed from said expression vector.

12. A host cell of claim 9 wherein said human MC-R1B protein is overexpressed from said expression vector.

13. A subcellular membrane fraction obtained from the host cell of claim 10 which contains recombinant human MC-R1B protein.

14. A subcellular membrane fraction obtained from the host cell of claim 11 which contains recombinant human MC-R1B protein.

15. A subcellular membrane fraction obtained from the host cell of claim 12 which contains recombinant human MC-R1B protein.

16. A purified nucleic acid molecule encoding human MC-R1B protein wherein the nucleic acid molecule encodes a protein consisting of an amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:17, SEQ ID NO:20, SEQ ID NO:23, and SEQ ID NO:26.

17. A purified human melanocortin 1 receptor protein which comprises a carboxy terminal amino acid domain as set forth in SEQ ID NO:27.

18. A purified human melanocortin 1 receptor protein of claim 17 which comprises the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:17, SEQ ID NO:20, SEQ ID NO:23, and SEQ ID NO:26.

* * * * *

UNITED STATES PATENT AND TRADEMARK OFFICE
CERTIFICATE OF CORRECTION

PATENT NO.    : 6,693,184 B1
DATED         : February 17, 2004
INVENTOR(S)   : Andrew D. Howard et al.

It is certified that error appears in the above-identified patent and that said Letters Patent is hereby corrected as shown below:

Title page,
Item [22], delete "Filed:     Jun. 18, 2001" and insert therefor:

--     PCT Filed:        Dec. 16, 1999
      PCT No.:          PCT/US99/17930
      § 371 (c) (1),
      (2), (4) Date:    Jun. 18, 2001
      PCT Pub. No.:     WO 00/39147
      PCT Pub. Date:    Jul. 6, 2000 --

Column 1,
Line 5, CROSS-REFERENCE TO RELATED APPLICATIONS, delete "The present application claims priority to U.S. Ser. No. 60/113,401, filed Dec. 23, 1998, which is hereby incorporated by reference," and insert therefor -- This application is a 371 of PCT/US99/17930, international filing date of December 16, 1999, which claims priority to U.S. Serial No. 60/113,401, filed Dec. 23, 1998, now abandoned, which is hereby incorporated by reference. --

Signed and Sealed this

Eighteenth Day of May, 2004

JON W. DUDAS
*Acting Director of the United States Patent and Trademark Office*

SEQUENCE LISTING

<160> NUMBER OF SEQ ID NOS: 46

<210> SEQ ID NO 1
<211> LENGTH: 1149
<212> TYPE: DNA
<213> ORGANISM: Homo sapien

<400> SEQUENCE: 1

```
atggctgtgc agggatccca gagaagactt ctgggctccc tcaactccac ccccacagcc      60
atcccccagc tggggctggc tgccaaccag acaggagccc ggtgcctgga ggtgtccatc     120
tctgacgggc tcttcctcag cctggggctg gtgagcttgg tggagaacgc gctggtggtg    180
gccaccatcg ccaagaaccg gaacctgcac tcacccatgt actgcttcat ctgctgcctg    240
```

-continued

```
gccttgtcgg acctgctggt gagcgggagc aacgtgctgg agacggccgt catcctcctg    300
ctggaggccg gtgcactggt ggcccgggct gcggtgctgc agcagctgga caatgtcatt    360
gacgtgatca cctgcagctc catgctgtcc agcctctgct tcctgggcgc catcgccgtg    420
gaccgctaca tctccatctt ctacgcactg cgttaccaca gcatcgtgac cctgccgcgg    480
gcgcggcaag ccgttgcggc catctgggtg gccagtgtcg tcttcagcac gctcttcatc    540
gcctactacg accacgtggc cgtcctgctg tgcctcgtgg tcttcttcct ggctatgctg    600
gtgctcatgg ccgtgctgta cgtccacatg ctggcccggg cctgccagca cgcccagggc    660
atcgcccggc tccacaagag gcagcgcccg gtccaccagg gctttggcct taaaggcgct    720
gtcaccctca ccatcctgct gggcattttc ttcctctgct ggggcccctt cttcctgcat    780
ctcacactca tcgtcctctg ccccgagcac cccacgtgcg gctgcatctt caagaacttc    840
aacctctttc tcgccctcat catctgcaat gccatcatcg accccctcat ctacgccttc    900
cacagccagg agctccgcag gacgctcaag gaggtgctga catgctcctg ctctcaggac    960
cgtgccctcg tcagctggga tgtgaagtct ctgggtggaa gtgtgtgcca agagctactc   1020
ccacagcagc cccaggagaa ggggccttgt gaccagaaag cttcatccac agccttgcag   1080
cggctcctgc aaaaggaggt gaaatccctg cctcaggcca agggaccagg tttgcaggag   1140
ccccccctag                                                         1149
```

<210> SEQ ID NO 2
<211> LENGTH: 382
<212> TYPE: PRT
<213> ORGANISM: Homo sapien

<400> SEQUENCE: 2

```
Met Ala Val Gln Gly Ser Gln Arg Arg Leu Leu Gly Ser Leu Asn Ser
 1               5                  10                  15

Thr Pro Thr Ala Ile Pro Gln Leu Gly Leu Ala Ala Asn Gln Thr Gly
             20                  25                  30

Ala Arg Cys Leu Glu Val Ser Ile Ser Asp Gly Leu Phe Leu Ser Leu
         35                  40                  45

Gly Leu Val Ser Leu Val Glu Asn Ala Leu Val Val Ala Thr Ile Ala
     50                  55                  60

Lys Asn Arg Asn Leu His Ser Pro Met Tyr Cys Phe Ile Cys Cys Leu
 65                  70                  75                  80

Ala Leu Ser Asp Leu Leu Val Ser Gly Ser Asn Val Leu Glu Thr Ala
             85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
        115                 120                 125

Leu Ser Ser Leu Cys Phe Leu Gly Ala Ile Ala Val Asp Arg Tyr Ile
    130                 135                 140

Ser Ile Phe Tyr Ala Leu Arg Tyr His Ser Ile Val Thr Leu Pro Arg
145                 150                 155                 160

Ala Arg Gln Ala Val Ala Ala Ile Trp Val Ala Ser Val Val Phe Ser
                165                 170                 175

Thr Leu Phe Ile Ala Tyr Tyr Asp His Val Ala Val Leu Leu Cys Leu
            180                 185                 190

Val Val Phe Phe Leu Ala Met Leu Val Leu Met Ala Val Leu Tyr Val
        195                 200                 205
```

```
His Met Leu Ala Arg Ala Cys Gln His Ala Gln Gly Ile Ala Arg Leu
    210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
            260                 265                 270

Cys Gly Cys Ile Phe Lys Asn Phe Asn Leu Phe Leu Ala Leu Ile Ile
        275                 280                 285

Cys Asn Ala Ile Ile Asp Pro Leu Ile Tyr Ala Phe His Ser Gln Glu
    290                 295                 300

Leu Arg Arg Thr Leu Lys Glu Val Leu Thr Cys Ser Cys Ser Gln Asp
305                 310                 315                 320

Arg Ala Leu Val Ser Trp Asp Val Lys Ser Leu Gly Gly Ser Val Cys
                325                 330                 335

Gln Glu Leu Leu Pro Gln Gln Pro Glu Lys Gly Pro Cys Asp Gln
            340                 345                 350

Lys Ala Ser Ser Thr Ala Leu Gln Arg Leu Leu Gln Lys Glu Val Lys
        355                 360                 365

Ser Leu Pro Gln Ala Lys Gly Pro Gly Leu Gln Glu Pro Pro
    370                 375                 380

<210> SEQ ID NO 3
<211> LENGTH: 1149
<212> TYPE: DNA
<213> ORGANISM: Homo sapien

<400> SEQUENCE: 3
atggctgtgc agggatccca gagaagactt ctgggctccc tcaactccac ccccacagcc      60 atccccagc tggggctggc tgccaaccag acaggagccc ggtgcctgga ggtgtccatc      120
tctgacgggc tcttcctcag cctggggctg gtgagcttgg tggagaacgc gctggtggtg      180
gccaccatcg ccaagaaccg gaacctgcac tcacccatgt actgcttcat ctgctgcctg      240
gccttgtcgg acctgctggt gagcgggagc aacgtgctgg agacggccgt catcctcctg      300
ctggaggccg tgcactggt ggcccgggct gcggtgctgc agcagctgga caatgtcatt      360
gacgtgatca cctgcagctc catgctgtcc agcctctgct tcctgggcgc catcgccgtg      420
gaccgctaca tctccatctt ctacgcactg cgttaccaca gcatcgtgac cctgccgcgg      480
gcgcggcaag ccgttgcggc catctgggtg gccagtgtcg tcttcagcac gctcttcatc      540
gcctactacg accacgtggc cgtcctgctg tgcctcgtgg tcttcttcct ggctatgctg      600
gtgctcatgg ccgtgctgta cgtccacatg ctggcccggg cctgccagca cgcccagggc      660
atcgcccggc tccacaagag gcagcgcccg gtccaccagg gctttggcct taaaggcgct      720 gtcacccctca ccatcctgct gggcattttc ttcctctgct ggggcccctt cttcctgcat      780
ctcacactca tcgtcctctg ccccgagcac cccacgtgcg gctgcatctt caagaacttc      840
aacctctttc tcgccctcat catctgcaat gccatcatcg accccctcat ctacgccttc      900
cacagccagg agctccgcag gacgctcaag gaggtgctga catgctcctg ctctcaggac      960
cgtgccctcg tcagctggga tgtgaagtct ctgggtggaa gtgtgtgcca agagctactc     1020
ccacagcagc ccaggagaa ggggcttttgt gaccagaaag cttcatccac agccttgcag     1080
cggctcctgc aaaaggaggt gaaatccctg cctcaggcca agggaccagg tttgcaggag     1140
``` cccccctag 1149

<210> SEQ ID NO 4
<211> LENGTH: 382
<212> TYPE: PRT
<213> ORGANISM: Homo sapien

<400> SEQUENCE: 4

```
Met Ala Val Gln Gly Ser Gln Arg Arg Leu Leu Gly Ser Leu Asn Ser
 1               5                  10                  15
Thr Pro Thr Ala Ile Pro Gln Leu Gly Leu Ala Ala Asn Gln Thr Gly
            20                  25                  30
Ala Arg Cys Leu Glu Val Ser Ile Ser Asp Gly Leu Phe Leu Ser Leu
        35                  40                  45
Gly Leu Val Ser Leu Val Glu Asn Ala Leu Val Val Ala Thr Ile Ala
    50                  55                  60
Lys Asn Arg Asn Leu His Ser Pro Met Tyr Cys Phe Ile Cys Cys Leu
65                  70                  75                  80
Ala Leu Ser Asp Leu Leu Val Ser Gly Ser Asn Val Leu Glu Thr Ala
                85                  90                  95
Val Ile Leu Leu Leu Glu Ala Gly Ala Leu Val Ala Arg Ala Ala Val
            100                 105                 110
Leu Gln Gln Leu Asp Asn Val Ile Asp Val Ile Thr Cys Ser Ser Met
        115                 120                 125
Leu Ser Ser Leu Cys Phe Leu Gly Ala Ile Ala Val Asp Arg Tyr Ile
    130                 135                 140
Ser Ile Phe Tyr Ala Leu Arg Tyr His Ser Ile Val Thr Leu Pro Arg
145                 150                 155                 160
Ala Arg Gln Ala Val Ala Ala Ile Trp Val Ala Ser Val Val Phe Ser
                165                 170                 175
Thr Leu Phe Ile Ala Tyr Tyr Asp His Val Ala Val Leu Leu Cys Leu
            180                 185                 190
Val Val Phe Phe Leu Ala Met Leu Val Leu Met Ala Val Leu Tyr Val
        195                 200                 205
His Met Leu Ala Arg Ala Cys Gln His Ala Gln Gly Ile Ala Arg Leu
    210                 215                 220
His Lys Arg Gln Arg Pro Val His Gln Gly Phe Gly Leu Lys Gly Ala
225                 230                 235                 240
Val Thr Leu Thr Ile Leu Leu Gly Ile Phe Phe Leu Cys Trp Gly Pro
                245                 250                 255
Phe Phe Leu His Leu Thr Leu Ile Val Leu Cys Pro Glu His Pro Thr
            260                 265                 270
Cys Gly Cys Ile Phe Lys Asn Phe Asn Leu Phe Leu Ala Leu Ile Ile
        275                 280                 285
Cys Asn Ala Ile Ile Asp Pro Leu Ile Tyr Ala Phe His Ser Gln Glu
    290                 295                 300
Leu Arg Arg Thr Leu Lys Glu Val Leu Thr Cys Ser Cys Ser Gln Asp
305                 310                 315                 320
Arg Ala Leu Val Ser Trp Asp Val Lys Ser Leu Gly Gly Ser Val Cys
                325                 330                 335
Gln Glu Leu Leu Pro Gln Gln Pro Gln Glu Lys Gly Leu Cys Asp Gln
            340                 345                 350
Lys Ala Ser Ser Thr Ala Leu Gln Arg Leu Leu Gln Lys Glu Val Lys
        355                 360                 365
```

Ser Leu Pro Gln Ala Lys Gly Pro Gly Leu Gln Glu Pro Pro
    370                 375                 380

<210> SEQ ID NO 5
<211> LENGTH: 1149
<212> TYPE: DNA
<213> ORGANISM: Homo sapien

<400> SEQUENCE: 5

| | | | | |
|---|---|---|---|---|
| atggctgtgc | agggatccca | gagaagactt | ctgggctccc | tcaactccac cccacagcc | 60 |
| atccccagc | tggggctggc | tgccaaccag | acaggagccc | ggtgcctgga ggtgtccatc | 120 |
| tctgacgggc | tcttcctcag | cctggggctg | gtgagcttgg | tgaagaacgc gctggtggtg | 180 |
| gccaccatcg | ccaagaaccg | gaacctgcac | tcacccatgt | actgcttcat ctgctgcctg | 240 |
| gccttgtcgg | acctgctggt | gagcgggagc | aacgtgctgg | agacggccgt catcctcctg | 300 |
| ctggaggccg | gtgcactggt | ggcccgggct | gcggtgctgc | agcagctgga caatgtcatt | 360 |
| gacgtgatca | cctgcagctc | catgctgtcc | agcctctgct | tcctgggcgc catcgccgtg | 420 |
| gaccgctaca | tctccatctt | ctacgcactg | cgctaccaca | gcatcgtgac cctgccgcgg | 480 |
| gcgcggcaag | ccgttgcggc | catctgggtg | gccagtgtcg | tcttcagcac gctcttcatc | 540 |
| gcctactacg | accacgtggc | cgtcctgctg | tgcctcgtgg | tcttcttcct ggctatgctg | 600 |
| gtgctcatgg | ccgtgctgta | cgtccacatg | ctggcccggg | cctgccagca cgcccagggc | 660 |
| atcgcccggc | tccacaagag | gcagcgcccc | gtccaccagg | gctttggcct taaaggcgct | 720 |
| gtcaccctca | ccatcctgct | gggcattttc | ttcctctgct | ggggccccctt cttcctgcat | 780 |
| ctcacactca | tcgtcctctg | ccccgagcac | cccacgtgcg | gctgcatctt caagaacttc | 840 |
| aacctctttc | tcgccctcat | catctgcaat | gccatcatcg | accccctcat ctacgccttc | 900 |
| cacagccagg | agtccgcag | gacgctcaag | gaggtgctga | catgctcctg ctctcaggac | 960 |
| cgtgccctcg | tcagctggga | tgtgaagtct | ctgggtggaa | gtgtgtgcca agagctactc | 1020 |
| ccacagcagc | cccaggagaa | ggggctttgt | gaccagaaag | cttcatccac agccttgcag | 1080 |
| cggctcctgc | aaaaggaggt | gaaatccctg | cctcaggcca | agggaccagg tttgcaggag | 1140 |
| ccccctag | | | | | 1149 |

<210> SEQ ID NO 6
<211> LENGTH: 382
<212> TYPE: PRT
<213> ORGANISM: Homo sapien

<400> SEQUENCE: 6

Met Ala Val Gln Gly Ser Gln Arg Arg Leu Leu Gly Ser Leu Asn Ser
 1               5                  10                  15

Thr Pro Thr Ala Ile Pro Gln Leu Gly Leu Ala Ala Asn Gln Thr Gly
            20                  25                  30

Ala Arg Cys Leu Glu Val Ser Ile Ser Asp Gly Leu Phe Leu Ser Leu
        35                  40                  45

Gly Leu Val Ser Leu Val Lys Asn Ala Leu Val Val Ala Thr Ile Ala
    50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Ser Asn Val Leu Glu Thr Ala
                85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
    115                 120                 125

Leu Ser Ser Leu Cys Phe Leu Gly Ala Ile Ala Val Asp Arg Tyr Ile
130                 135                 140

Ser Ile Phe Tyr Ala Leu Arg Tyr His Ser Ile Val Thr Leu Pro Arg
145                 150                 155                 160

Ala Arg Gln Ala Val Ala Ile Trp Val Ala Ser Val Val Phe Ser
                165                 170                 175

Thr Leu Phe Ile Ala Tyr Tyr Asp His Val Ala Val Leu Leu Cys Leu
                180                 185                 190

Val Val Phe Phe Leu Ala Met Leu Val Leu Met Ala Val Leu Tyr Val
            195                 200                 205

His Met Leu Ala Arg Ala Cys Gln His Ala Gln Gly Ile Ala Arg Leu
        210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
            260                 265                 270

Cys Gly Cys Ile Phe Lys Asn Phe Asn Leu Phe Leu Ala Leu Ile Ile
        275                 280                 285

Cys Asn Ala Ile Ile Asp Pro Leu Ile Tyr Ala Phe His Ser Gln Glu
290                 295                 300

Leu Arg Arg Thr Leu Lys Glu Val Leu Thr Cys Ser Cys Ser Gln Asp
305                 310                 315                 320

Arg Ala Leu Val Ser Trp Asp Val Lys Ser Leu Gly Gly Ser Val Cys
                325                 330                 335

Gln Glu Leu Leu Pro Gln Gln Pro Gln Glu Lys Gly Leu Cys Asp Gln
            340                 345                 350

Lys Ala Ser Ser Thr Ala Leu Gln Arg Leu Leu Gln Lys Glu Val Lys
        355                 360                 365

Ser Leu Pro Gln Ala Lys Gly Pro Gly Leu Gln Glu Pro Pro
370                 375                 380

<210> SEQ ID NO 7
<211> LENGTH: 1149
<212> TYPE: DNA
<213> ORGANISM: Homo sapien

<400> SEQUENCE: 7
atggctgtgc agggatccca gagaagactt ctgggctccc tcaactccac ccccacagcc    60
atcccccagc tggggctggc tgccaaccag acaggagccc ggtgcctgga ggtgtccatc   120
tctgacgggc tcttcctcag cctggggctg gtgagcttgg tggagaacgc gctggtggtg   180
gccaccatcg ccaagaaccg gaacctgcac tcacccatgt actgcttcat ctgctgcctg   240
gccttgtcgg acctgctggt gagcgggagc aacgtgctgg agacggccgt catcctcctg   300
ctggaggccg gtgcactggt ggcccgggct gcggtgctgc agcagctgga caatgtcatt   360
gacgtgatca cctgcagctt catgctgtcc agcctctgct cctgggcgc catcgccgtg   420 gaccgctaca tctccatctt ctacgcactg tgctaccaca gcatcgtgac cctgccgcgg   480
gcgcggcgag ccgttgcggc catctgggtg gccagtgtcg tcttcagcac gctcttcatc   540
gcctactacg accacgtggc cgtcctgctg tgcctcgtgg tcttcttcct ggctatgctg   600

-continued

```
gtgctcatgg ccgtgctgta cgtccacatg ctggcccggg cctgccagca cgcccagggc    660
atcgcccggc tccacaagag gcagcgcccg gtccaccagg gctttggcct taaaggcgct    720
gtcaccctca ccatcctgct gggcattttc ttcctctgct ggggcccctt cttcctgcat    780
ctcacactca tcgtcctctg ccccgagcac cccacgtgcg gctgcatctt caagaacttc    840
aacctctttc tcgccctcat catctgcaat gccatcatcg accccctcat ctacgccttc    900
cacagccagg agctccgcag gacgctcaag gaggtgctga catgctcctg ctctcaggac    960
cgtgccctcg tcagctggga tgtgaagtct ctgggtggaa gtgtgtgcca agagctactc    1020
ccacagcagc cccaggagaa ggggctttgt gaccagaaag cttcatccac agccttgcag    1080
cggctcctgc aaaaggaggt gaaatccctg cctcaggcca agggaccagg tttgcaggag    1140
ccccccctag                                                          1149
```

<210> SEQ ID NO 8
<211> LENGTH: 382
<212> TYPE: PRT
<213> ORGANISM: Homo sapien

<400> SEQUENCE: 8

```
Met Ala Val Gln Gly Ser Gln Arg Arg Leu Leu Gly Ser Leu Asn Ser
  1               5                  10                  15

Thr Pro Thr Ala Ile Pro Gln Leu Gly Leu Ala Ala Asn Gln Thr Gly
                 20                  25                  30

Ala Arg Cys Leu Glu Val Ser Ile Ser Asp Gly Leu Phe Leu Ser Leu
             35                  40                  45

Gly Leu Val Ser Leu Val Glu Asn Ala Leu Val Val Ala Thr Ile Ala
         50                  55                  60

Lys Asn Arg Asn Leu His Ser Pro Met Tyr Cys Phe Ile Cys Cys Leu
 65                  70                  75                  80

Ala Leu Ser Asp Leu Leu Val Ser Gly Ser Asn Val Leu Glu Thr Ala
                 85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Phe Met
        115                 120                 125

Leu Ser Ser Leu Cys Phe Leu Gly Ala Ile Ala Val Asp Arg Tyr Ile
    130                 135                 140

Ser Ile Phe Tyr Ala Leu Cys Tyr His Ser Ile Val Thr Leu Pro Arg
145                 150                 155                 160

Ala Arg Arg Ala Val Ala Ala Ile Trp Val Ala Ser Val Val Phe Ser
                165                 170                 175

Thr Leu Phe Ile Ala Tyr Tyr Asp His Val Ala Val Leu Leu Cys Leu
            180                 185                 190

Val Val Phe Phe Leu Ala Met Leu Val Leu Met Ala Val Leu Tyr Val
        195                 200                 205

His Met Leu Ala Arg Ala Cys Gln His Ala Gln Gly Ile Ala Arg Leu
    210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
            260                 265                 270
```

```
Cys Gly Cys Ile Phe Lys Asn Phe Asn Leu Phe Leu Ala Leu Ile Ile
            275                 280                 285

Cys Asn Ala Ile Ile Asp Pro Leu Ile Tyr Ala Phe His Ser Gln Glu
        290                 295                 300

Leu Arg Arg Thr Leu Lys Glu Val Leu Thr Cys Ser Cys Ser Gln Asp
305                 310                 315                 320

Arg Ala Leu Val Ser Trp Asp Val Lys Ser Leu Gly Gly Ser Val Cys
                325                 330                 335

Gln Glu Leu Leu Pro Gln Pro Gln Glu Lys Gly Leu Cys Asp Gln
            340                 345                 350

Lys Ala Ser Ser Thr Ala Leu Gln Arg Leu Leu Gln Lys Glu Val Lys
                355                 360                 365

Ser Leu Pro Gln Ala Lys Gly Pro Gly Leu Gln Glu Pro Pro
        370                 375                 380
```

<210> SEQ ID NO 9
<211> LENGTH: 1149
<212> TYPE: DNA
<213> ORGANISM: Homo sapien

<400> SEQUENCE: 9

```
atggctgtgc agggatccca gagaagactt ctgggctccc tcaactccac ccccacagcc      60
atcccccagc tggggctggc tgccaaccag acaggagccc ggtgcctgga ggtgtccatc     120
tctgacgggc tcttcctcag cctggggctg gtgagcttgg tggagaacgc gctggtggtg     180
gccaccatcg ccaagaaccg gaacctgcac tcacccatgt actgcttcat ctgctgcctg     240
gccttgtcgg acctgctggt gagcgggagc aacgtgctgg agacggccgt catcctcctg     300
ctggaggccg gtgcactggt ggcccgggct gcggtgctgc agcagctgga caatgtcatt     360
gacgtgatca cctgcagctc catgctgtcc agcctctgct tcctgggcgc catcgccgtg     420
gaccgctaca tctccatctt ctacgcactg cgctaccaca gcatcgtgac cctgccgcgg     480
gcgcggcgag ccgttgcggc catctgggtg gccagtgtcg tcttcagcac gctcttcatc     540
gcctactacg accacgcggc cgtcctgctg tgcctcgtgg tcttcttcct ggctatgctg     600
gtgctcatgg ccgtgctgta cgtccacatg ctggcccggg cctgccagca cgcccagggc     660
atcgcccggc tccacaagag gcagcgcccg gtccaccagg gctttggcct taaaggcgct     720
gtcaccctca ccatcctgct gggcattttc ttcctctgct ggggcccctt cttcctgcat     780
ctcacactca tcgtcctctg ccccgagcac cccacgtgcg gctgcatctt caagaacttc     840
aacctctttc tcgccctcat catctgcaat gccatcatcg accccctcat ctacgccttc     900
cacagccagg agctccgcag gacgctcaag gaggtgctga catgctcctg ctctcaggac     960
cgtgccctcg tcagctggga tgtgaagtct ctgggtggaa gtgtgtgcca agagcgactc    1020
ccacagcagc cccaggagaa ggggctttgt gaccagaaag cttcatccac agccttgcag    1080
cggctccctgc aaaaggggggt gaaatccctg cctcaggcca agggaccagg tttgcaggag    1140
ccccccctag                                                           1149
```

<210> SEQ ID NO 10
<211> LENGTH: 382
<212> TYPE: PRT
<213> ORGANISM: Homo sapien

<400> SEQUENCE: 10

Met Ala Val Gln Gly Ser Gln Arg Arg Leu Leu Gly Ser Leu Asn Ser

```
  1               5                    10                      15
Thr Pro Thr Ala Ile Pro Gln Leu Gly Leu Ala Ala Asn Gln Thr Gly
             20                 25                  30
Ala Arg Cys Leu Glu Val Ser Ile Ser Asp Gly Leu Phe Leu Ser Leu
         35                  40                  45
Gly Leu Val Ser Leu Val Glu Asn Ala Leu Val Val Ala Thr Ile Ala
    50                  55                  60
Lys Asn Arg Asn Leu His Ser Pro Met Tyr Cys Phe Ile Cys Cys Leu
65                  70                  75                  80
Ala Leu Ser Asp Leu Leu Val Ser Gly Ser Asn Val Leu Glu Thr Ala
                85                  90                  95
Val Ile Leu Leu Leu Glu Ala Gly Ala Leu Val Ala Arg Ala Ala Val
            100                 105                 110
Leu Gln Gln Leu Asp Asn Val Ile Asp Val Ile Thr Cys Ser Ser Met
        115                 120                 125
Leu Ser Ser Leu Cys Phe Leu Gly Ala Ile Ala Val Asp Arg Tyr Ile
    130                 135                 140
Ser Ile Phe Tyr Ala Leu Arg Tyr His Ser Ile Val Thr Leu Pro Arg
145                 150                 155                 160
Ala Arg Arg Ala Val Ala Ala Ile Trp Val Ala Ser Val Val Phe Ser
                165                 170                 175
Thr Leu Phe Ile Ala Tyr Tyr Asp His Ala Ala Val Leu Leu Cys Leu
            180                 185                 190
Val Val Phe Phe Leu Ala Met Leu Val Leu Met Ala Val Leu Tyr Val
        195                 200                 205
His Met Leu Ala Arg Ala Cys Gln His Ala Gln Gly Ile Ala Arg Leu
    210                 215                 220
His Lys Arg Gln Arg Pro Val His Gln Gly Phe Gly Leu Lys Gly Ala
225                 230                 235                 240
Val Thr Leu Thr Ile Leu Leu Gly Ile Phe Phe Leu Cys Trp Gly Pro
                245                 250                 255
Phe Phe Leu His Leu Thr Leu Ile Val Leu Cys Pro Glu His Pro Thr
            260                 265                 270
Cys Gly Cys Ile Phe Lys Asn Phe Asn Leu Phe Leu Ala Leu Ile Ile
        275                 280                 285
Cys Asn Ala Ile Ile Asp Pro Leu Ile Tyr Ala Phe His Ser Gln Glu
    290                 295                 300
Leu Arg Arg Thr Leu Lys Glu Val Leu Thr Cys Ser Cys Ser Gln Asp
305                 310                 315                 320
Arg Ala Leu Val Ser Trp Asp Val Lys Ser Leu Gly Gly Ser Val Cys
                325                 330                 335
Gln Glu Arg Leu Pro Gln Gln Pro Gln Glu Lys Gly Leu Cys Asp Gln
            340                 345                 350
Lys Ala Ser Ser Thr Ala Leu Gln Arg Leu Leu Gln Lys Gly Val Lys
        355                 360                 365
Ser Leu Pro Gln Ala Lys Gly Pro Gly Leu Gln Glu Pro Pro
    370                 375                 380

<210> SEQ ID NO 11
<211> LENGTH: 1149
<212> TYPE: DNA
<213> ORGANISM: Homo sapien

<400> SEQUENCE: 11
```

-continued

| | |
|---|---|
| atggctgtgc agggatccca gagaagactt ctgggctccc tcaactccac ccccacagcc | 60 |
| atcccccagc tgggctggc tgccaaccag acaggagccc ggtgctggaa ggtgtccatc | 120 |
| tctgacgggc tcttcctcag cctggggctg gtgagcttgg tgaagaacgc gctggtggtg | 180 |
| gccaccatcg ccaagaaccg aacctgcac tcacccatgt actgcttcat ctgctgcctg | 240 |
| gccttgtcgg acctgctggt gagcgggagc aacgtgctgg agacggccgt catcctcctg | 300 |
| ctggaggccg gtgcactggt ggcccgggct gcggtgctgc agcagctgga caatgtcatt | 360 |
| gacgtgatca cctgcagctc catgctgtcc agcctctgct tcctgggcgc catcgccgtg | 420 |
| gaccgctaca tctccatctt ctacgcactg cgctaccaca gcatcgtgac cctgccgcgg | 480 |
| gcgcggcaag ccgttgcggc catctgggtg gccagtgtcg tcttcagcac gctcttcatc | 540 |
| gcctactacg accacgtggc cgtcctgctg tgcctcgtgg tcttcttcct ggctatgctg | 600 |
| gtgctcatgg ccgtgctgta cgtccacatg ctggcccggg cctgccagca cgcccagggc | 660 |
| atcgcccggc tccacaagag gcagcgcccg gtccaccagg gctttggcct taaaggcgct | 720 |
| gtcaccctca ccatcctgct gggcattttc ttcctctgct ggggcccctt cttcctgcat | 780 |
| ctcacactca tcgtcctctg ccccgagcac cccacgtgcg gctgcatctt caagaacttc | 840 |
| aacctctttc tcgccctcat catctgcaat gccatcatcg acccctcat ctacgccttc | 900 |
| cacagccagg agctccgcag gacgctcaag gaggtgctga catgctcctg ctctcaggac | 960 |
| cgtgccctcg tcagctggga tgtgaagtct ctgggtggaa gtgtgtgcca agagctactc | 1020 |
| ccacagcagc cccaggagaa ggggctttgt gaccagaaag cttcatccac agccttgcag | 1080 |
| cggctcctgc aaaaggaggt gaaatccctg cctcaggcca agggaccagg tttgcaggag | 1140 |
| cccccctag | 1149 |

<210> SEQ ID NO 12
<211> LENGTH: 382
<212> TYPE: PRT
<213> ORGANISM: Homo sapien

<400> SEQUENCE: 12

```
Met Ala Val Gln Gly Ser Gln Arg Arg Leu Leu Gly Ser Leu Asn Ser
 1               5                  10                  15

Thr Pro Thr Ala Ile Pro Gln Leu Gly Leu Ala Ala Asn Gln Thr Gly
            20                  25                  30

Ala Arg Cys Leu Glu Val Ser Ile Ser Asp Gly Leu Phe Leu Ser Leu
        35                  40                  45

Gly Leu Val Ser Leu Val Lys Asn Ala Leu Val Val Ala Thr Ile Ala
    50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Ser Asn Val Leu Glu Thr Ala
                85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
        115                 120                 125

Leu Ser Ser Leu Cys Phe Leu Gly Ala Ile Ala Val Asp Arg Tyr Ile
    130                 135                 140

Ser Ile Phe Tyr Ala Leu Arg Tyr His Ser Ile Val Thr Leu Pro Arg
145                 150                 155                 160

Ala Arg Gln Ala Val Ala Ala Ile Trp Val Ala Ser Val Val Phe Ser
```

|     |     |     |     |     | 165 |     |     |     | 170 |     |     |     |     | 175 |     |
| --- | --- | --- | --- | --- | --- | --- | --- | --- | --- | --- | --- | --- | --- | --- | --- |
| Thr | Leu | Phe | Ile | Ala | Tyr | Tyr | Asp | His | Val | Ala | Val | Leu | Leu | Cys | Leu |
|     |     |     |     | 180 |     |     |     |     | 185 |     |     |     |     | 190 |     |
| Val | Val | Phe | Phe | Leu | Ala | Met | Leu | Val | Leu | Met | Ala | Val | Leu | Tyr | Val |
|     |     |     | 195 |     |     |     |     | 200 |     |     |     |     | 205 |     |     |
| His | Met | Leu | Ala | Arg | Ala | Cys | Gln | His | Ala | Gln | Gly | Ile | Ala | Arg | Leu |
|     |     | 210 |     |     |     |     | 215 |     |     |     |     | 220 |     |     |     |
| His | Lys | Arg | Gln | Arg | Pro | Val | His | Gln | Gly | Phe | Gly | Leu | Lys | Gly | Ala |
| 225 |     |     |     |     | 230 |     |     |     |     | 235 |     |     |     |     | 240 |
| Val | Thr | Leu | Thr | Ile | Leu | Leu | Gly | Ile | Phe | Phe | Leu | Cys | Trp | Gly | Pro |
|     |     |     |     | 245 |     |     |     |     | 250 |     |     |     |     | 255 |     |
| Phe | Phe | Leu | His | Leu | Thr | Leu | Ile | Val | Leu | Cys | Pro | Glu | His | Pro | Thr |
|     |     |     | 260 |     |     |     |     | 265 |     |     |     |     | 270 |     |     |
| Cys | Gly | Cys | Ile | Phe | Lys | Asn | Phe | Asn | Leu | Phe | Leu | Ala | Leu | Ile | Ile |
|     |     | 275 |     |     |     |     | 280 |     |     |     |     | 285 |     |     |     |
| Cys | Asn | Ala | Ile | Ile | Asp | Pro | Leu | Ile | Tyr | Ala | Phe | His | Ser | Gln | Glu |
|     | 290 |     |     |     |     | 295 |     |     |     |     | 300 |     |     |     |     |
| Leu | Arg | Arg | Thr | Leu | Lys | Glu | Val | Leu | Thr | Cys | Ser | Cys | Ser | Gln | Asp |
| 305 |     |     |     |     | 310 |     |     |     |     | 315 |     |     |     |     | 320 |
| Arg | Ala | Leu | Val | Ser | Trp | Asp | Val | Lys | Ser | Leu | Gly | Gly | Ser | Val | Cys |
|     |     |     |     | 325 |     |     |     |     | 330 |     |     |     |     | 335 |     |
| Gln | Glu | Leu | Leu | Pro | Gln | Gln | Pro | Gln | Glu | Lys | Gly | Leu | Cys | Asp | Gln |
|     |     |     | 340 |     |     |     |     | 345 |     |     |     |     | 350 |     |     |
| Lys | Ala | Ser | Ser | Thr | Ala | Leu | Gln | Arg | Leu | Leu | Gln | Lys | Glu | Val | Lys |
|     |     | 355 |     |     |     |     | 360 |     |     |     |     | 365 |     |     |     |
| Ser | Leu | Pro | Gln | Ala | Lys | Gly | Pro | Gly | Leu | Gln | Glu | Pro | Pro |     |     |
|     | 370 |     |     |     |     | 375 |     |     |     |     | 380 |     |     |     |     |

<210> SEQ ID NO 13
<211> LENGTH: 1149
<212> TYPE: DNA
<213> ORGANISM: Homo sapien

<400> SEQUENCE: 13

```
atggctgtgc agggatccca gagaagactt ctgggctccc tcaactccac ccccacagcc      60
atcccccagc tggggctggc tgccaaccag acaggagccc ggtgcctgga ggtgtccatc     120
tctgacgggc tcttcctcag cctggggctg gtgagcttgg tgaagaacgc gctggtggtg     180
gccaccatcg ccaagaaccg gaacctgcac tcacccatgt actgcttcat ctgctgcctg     240
gccttgtcgg acctgctggt gagcgggagc aacgtgctgg agacggccgt catcctcctg     300
ctggaggccg tgcactggt ggcccgggct gcggtgctgc agcagctgga caatgtcatt     360
gacgtgatca cctgcagctc catgctgtcc agcctctgct tcctgggcgc catcgccgtg     420
gaccgctaca tctccatctt ctacgcactg cgctaccaca gcatcgtgac cctgcgcgg     480
gcgcggcaag ccgttgcggc catctgggtg ccagtgtcg tcttcagcac gctcttcatc     540
gcctactacg accacgtggc cgtcctgctg tgcctcgtgg tcttcttcct ggctatgctg     600
gtgctcatgg ccgtgctgta cgtccacatg ctggcccggg cctgccagca cgcccagggc     660
atcgcccggc tccacaagag gcagcgcccg gtccaccagg gctttggcct taaaggcgct     720
gtcaccctca ccatcctgct gggcattttc ttcctctgct ggggcccctt cttcctgcat     780
ctcacactca tcgtcctctg ccccgagcac cccacgtgcg gctgcatctt caagaacttc     840
aacctctttc tcgccctcat catctgcaat gccatcatcg accccctcat ctacgccttc     900
```

-continued

```
cacagccagg agctccgcag gacgctcaag gaggtgctga catgctcctg ctctcaggac      960
cgtgccctcg tcagctggga tgtgaagtct ctgggtggaa gtgtgtgcca agagctactc     1020
ccacagcagc cccaggagaa ggggctttgt gaccagaaag cttcatccac agccttgcag     1080
cggctcctgc aaaaggaggt gaaatccctg cctcaggcca agggaccagg tttgcaggag     1140
ccccccctag                                                            1149
```

<210> SEQ ID NO 14
<211> LENGTH: 382
<212> TYPE: PRT
<213> ORGANISM: Homo sapien

<400> SEQUENCE: 14

| Met | Ala | Val | Gln | Gly | Ser | Gln | Arg | Arg | Leu | Leu | Gly | Ser | Leu | Asn | Ser |
|---|---|---|---|---|---|---|---|---|---|---|---|---|---|---|---|
| 1 | | | | 5 | | | | | 10 | | | | | 15 | |

| Thr | Pro | Thr | Ala | Ile | Pro | Gln | Leu | Gly | Leu | Ala | Ala | Asn | Gln | Thr | Gly |
|---|---|---|---|---|---|---|---|---|---|---|---|---|---|---|---|
| | | | 20 | | | | | 25 | | | | | 30 | | |

| Ala | Arg | Cys | Leu | Glu | Val | Ser | Ile | Ser | Asp | Gly | Leu | Phe | Leu | Ser | Leu |
|---|---|---|---|---|---|---|---|---|---|---|---|---|---|---|---|
| | | 35 | | | | | 40 | | | | | 45 | | | |

| Gly | Leu | Val | Ser | Leu | Val | Lys | Asn | Ala | Leu | Val | Val | Ala | Thr | Ile | Ala |
|---|---|---|---|---|---|---|---|---|---|---|---|---|---|---|---|
| 50 | | | | | 55 | | | | | 60 | | | | | |

| Lys | Asn | Arg | Asn | Leu | His | Ser | Pro | Met | Tyr | Cys | Phe | Ile | Cys | Cys | Leu |
|---|---|---|---|---|---|---|---|---|---|---|---|---|---|---|---|
| 65 | | | | 70 | | | | | 75 | | | | | 80 | |

| Ala | Leu | Ser | Asp | Leu | Leu | Val | Ser | Gly | Ser | Asn | Val | Leu | Glu | Thr | Ala |
|---|---|---|---|---|---|---|---|---|---|---|---|---|---|---|---|
| | | | 85 | | | | | 90 | | | | | 95 | | |

| Val | Ile | Leu | Leu | Leu | Glu | Ala | Gly | Ala | Leu | Val | Ala | Arg | Ala | Ala | Val |
|---|---|---|---|---|---|---|---|---|---|---|---|---|---|---|---|
| | | 100 | | | | | 105 | | | | | 110 | | | |

| Leu | Gln | Gln | Leu | Asp | Asn | Val | Ile | Asp | Val | Ile | Thr | Cys | Ser | Ser | Met |
|---|---|---|---|---|---|---|---|---|---|---|---|---|---|---|---|
| | 115 | | | | | 120 | | | | | 125 | | | | |

| Leu | Ser | Ser | Leu | Cys | Phe | Leu | Gly | Ala | Ile | Ala | Val | Asp | Arg | Tyr | Ile |
|---|---|---|---|---|---|---|---|---|---|---|---|---|---|---|---|
| | 130 | | | | | 135 | | | | | 140 | | | | |

| Ser | Ile | Phe | Tyr | Ala | Leu | Arg | Tyr | His | Ser | Ile | Val | Thr | Leu | Pro | Arg |
|---|---|---|---|---|---|---|---|---|---|---|---|---|---|---|---|
| 145 | | | | | 150 | | | | | 155 | | | | | 160 |

| Ala | Arg | Gln | Ala | Val | Ala | Ala | Ile | Trp | Val | Ala | Ser | Val | Val | Phe | Ser |
|---|---|---|---|---|---|---|---|---|---|---|---|---|---|---|---|
| | | | | 165 | | | | | 170 | | | | | 175 | |

| Thr | Leu | Phe | Ile | Ala | Tyr | Tyr | Asp | His | Val | Ala | Val | Leu | Leu | Cys | Leu |
|---|---|---|---|---|---|---|---|---|---|---|---|---|---|---|---|
| | | | 180 | | | | | 185 | | | | | 190 | | |

| Val | Val | Phe | Phe | Leu | Ala | Met | Leu | Val | Leu | Met | Ala | Val | Leu | Tyr | Val |
|---|---|---|---|---|---|---|---|---|---|---|---|---|---|---|---|
| | | | 195 | | | | | 200 | | | | | 205 | | |

| His | Met | Leu | Ala | Arg | Ala | Cys | Gln | His | Ala | Gln | Gly | Ile | Ala | Arg | Leu |
|---|---|---|---|---|---|---|---|---|---|---|---|---|---|---|---|
| | 210 | | | | | 215 | | | | | 220 | | | | |

| His | Lys | Arg | Gln | Arg | Pro | Val | His | Gln | Gly | Phe | Gly | Leu | Lys | Gly | Ala |
|---|---|---|---|---|---|---|---|---|---|---|---|---|---|---|---|
| 225 | | | | | 230 | | | | | 235 | | | | | 240 |

| Val | Thr | Leu | Thr | Ile | Leu | Leu | Gly | Ile | Phe | Phe | Leu | Cys | Trp | Gly | Pro |
|---|---|---|---|---|---|---|---|---|---|---|---|---|---|---|---|
| | | | | 245 | | | | | 250 | | | | | 255 | |

| Phe | Phe | Leu | His | Leu | Thr | Leu | Ile | Val | Leu | Cys | Pro | Glu | His | Pro | Thr |
|---|---|---|---|---|---|---|---|---|---|---|---|---|---|---|---|
| | | | 260 | | | | | 265 | | | | | 270 | | |

| Cys | Gly | Cys | Ile | Phe | Lys | Asn | Phe | Asn | Leu | Phe | Leu | Ala | Leu | Ile | Ile |
|---|---|---|---|---|---|---|---|---|---|---|---|---|---|---|---|
| | | 275 | | | | | 280 | | | | | 285 | | | |

| Cys | Asn | Ala | Ile | Ile | Asp | Pro | Leu | Ile | Tyr | Ala | Phe | His | Ser | Gln | Glu |
|---|---|---|---|---|---|---|---|---|---|---|---|---|---|---|---|
| | 290 | | | | | 295 | | | | | 300 | | | | |

| Leu | Arg | Arg | Thr | Leu | Lys | Glu | Val | Leu | Thr | Cys | Ser | Cys | Ser | Gln | Asp |
|---|---|---|---|---|---|---|---|---|---|---|---|---|---|---|---|
| 305 | | | | | 310 | | | | | 315 | | | | | 320 |

| Arg | Ala | Leu | Val | Ser | Trp | Asp | Val | Lys | Ser | Leu | Gly | Gly | Ser | Val | Cys |
|---|---|---|---|---|---|---|---|---|---|---|---|---|---|---|---|

|  |  | 325 |  |  | 330 |  |  | 335 |  |

Gln Glu Leu Leu Pro Gln Gln Pro Gln Glu Lys Gly Leu Cys Asp Gln
                    340                 345                 350

Lys Ala Ser Ser Thr Ala Leu Gln Arg Leu Leu Gln Lys Glu Val Lys
            355                 360                 365

Ser Leu Pro Gln Ala Lys Gly Pro Gly Leu Gln Glu Pro Pro
    370                 375                 380

<210> SEQ ID NO 15
<211> LENGTH: 1530
<212> TYPE: DNA
<213> ORGANISM: Homo sapien
<220> FEATURE:
<221> NAME/KEY: misc_feature
<222> LOCATION: (1094)...(1094)
<223> OTHER INFORMATION: n = unknown

<400> SEQUENCE: 15

```
atggctgtgc agggatccca gagaagactt ctgggctccc tcaactccac ccccacagcc      60
atcccccagc tggggctggc tgccaaccag acaggagccc ggtgcctgga ggtgtccatc     120
tctgacgggc tcttcctcag cctggggctg gtgagcttgg tggagaacgc gctggtggtg     180
gccaccatcg ccaagaaccg gaacctgcac tcacccatgt actgcttcat ctgctgcctg     240
gccttgtcgg acctgctggt gagcgggagc aacgtgctgg agacggccgt catcctcctg     300
ctggaggccg tgcactggt ggcccaggct gcggtgctgc agcagctgga caatgtcatt     360
gacgtgatca cctgcagctc catgctgtcc agcctctgct tcctgggcgc catcgccgcg     420
gaccgctaca tctccatctt ctacgcactg cgctaccaca gcatcgtgac cctgccgcgg     480
gcgcggcgag ccgttgcggc catctgggtg gccagtgtcg tcttcagcac gctcttcatc     540
gcctactacg accacgtggc cgtcctgctg tgcctcgtgg tcttcttcct ggctatgctg     600
gtgctcatgg ccgtgctgta cgtccacatg ctggcccggg cctgccagca cgcccagggc     660
atcgcccggc tccacaagag gcagcgcccg gtccaccagg gctttggcct taaaggcgct     720
gtcaccctca ccatcctgct gggcattttc ttcctctgct ggggcccctt cttcctgcat     780
ctcacactca tcgtcctctg ccccgagcac cccacgtgcg gctgcatctt caagaacttc     840
aacctctttc tcgccctcat catctgcaat gccatcatcg acccctcat ctacgccttc     900
acagccagg agctccgcag gacgctcaag gaggtgctga catgctcctg gtgagcgcgg     960
tgcacgcggc tttaagtgtg ctgggcagag ggaggtggtg atattgtgtg gtctggttcc    1020
tgtgtgaccc tgggcagttc cttacctccc tggtccccgt ttgtcaaaga ggatggacta    1080
aatgatctct gaangtgttg aagcgcggac ccttctgggt ccaggagggg gtccctgcaa    1140
aactccaggc aggacttctc accagcagtc gtggggaacg gaggaggaca tggggaggtt    1200
gtggggcctc aggctccggg caccaggggc caacctcagg ctcctaaaga gacattttcc    1260
gcccactcct gggacactcc gtctgctcca atgactgagc agcatccacc ccaccccatc    1320
tttgctgcca gctctcagga ccgtgccctc gtcagctggg atgtgaagtc tctgggtgga    1380
agtgtgtgcc aagagctact cccacagcag ccccaggaga aggggctttg tgaccagaaa    1440
gcttcatcca cagccttgca gcggctcctg caaaaggagg tgaaatccct gcctcaggcc    1500
aagggaccag gtttgcagga gccccctag                                      1530
```

<210> SEQ ID NO 16
<211> LENGTH: 1149
<212> TYPE: DNA

<213> ORGANISM: Homo sapien

<400> SEQUENCE: 16

```
atggctgtgc agggatccca gagaagactt ctgggctccc tcaactccac ccccacagcc      60
atcccccagc tggggctggc tgccaaccag acaggagccc ggtgcctgga ggtgtccatc     120
tctgacgggc tcttcctcag cctggggctg gtgagcttgg tggagaacgc gctggtggtg     180
gccaccatcg ccaagaaccg aacctgcac tcacccatgt actgcttcat ctgctgcctg      240
gccttgtcgg acctgctggt gagcgggagc aacgtgctgg agacggccgt catcctcctg     300
ctggaggccg gtgcactggt ggcccaggct gcggtgctgc agcagctgga caatgtcatt     360
gacgtgatca cctgcagctc catgctgtcc agcctctgct tcctgggcgc catcgccgcg     420
gaccgctaca tctccatctt ctacgcactg cgctaccaca gcatcgtgac cctgccgcgg     480
gcgcggcgag ccgttgcggc catctgggtg ccagtgtcg tcttcagcac gctcttcatc      540
gcctactacg accacgtggc cgtcctgctg tgcctcgtgg tcttcttcct ggctatgctg     600
gtgctcatgg ccgtgctgta cgtccacatg ctggcccggg cctgccagca cgcccagggc     660
atcgcccggc tccacaagag gcagcgcccg gtccaccagg gctttggcct taaaggcgct     720
gtcacccctca ccatcctgct gggcattttc ttcctctgct ggggcccctt cttcctgcat     780
ctcacactca tcgtcctctg ccccgagcac cccacgtgcg gctgcatctt caagaacttc     840
aacctcttc tcgccctcat catctgcaat gccatcatcg accccctcat ctacgccttc     900
cacagccagg agctccgcag gacgctcaag gaggtgctga catgctcctg ctctcaggac     960
cgtgccctcg tcagctggga tgtgaagtct ctgggtggaa gtgtgtgcca agagctactc    1020
ccacagcagc cccaggagaa ggggctttgt gaccagaaag cttcatccac agccttgcag    1080
cggctcctgc aaaaggaggt gaaatccctg cctcaggcca agggaccagg tttgcaggag    1140
ccccctag                                                             1149
```

<210> SEQ ID NO 17
<211> LENGTH: 382
<212> TYPE: PRT
<213> ORGANISM: Homo sapien

<400> SEQUENCE: 17

```
Met Ala Val Gln Gly Ser Gln Arg Arg Leu Leu Gly Ser Leu Asn Ser
  1               5                  10                  15

Thr Pro Thr Ala Ile Pro Gln Leu Gly Leu Ala Ala Asn Gln Thr Gly
                 20                  25                  30

Ala Arg Cys Leu Glu Val Ser Ile Ser Asp Gly Leu Phe Leu Ser Leu
             35                  40                  45

Gly Leu Val Ser Leu Val Glu Asn Ala Leu Val Val Ala Thr Ile Ala
         50                  55                  60

Lys Asn Arg Asn Leu His Ser Pro Met Tyr Cys Phe Ile Cys Cys Leu
 65                  70                  75                  80

Ala Leu Ser Asp Leu Leu Val Ser Gly Ser Asn Val Leu Glu Thr Ala
                 85                  90                  95

Val Ile Leu Leu Leu Glu Ala Gly Ala Leu Val Ala Gln Ala Ala Val
            100                 105                 110

Leu Gln Gln Leu Asp Asn Val Ile Asp Val Ile Thr Cys Ser Ser Met
        115                 120                 125

Leu Ser Ser Leu Cys Phe Leu Gly Ala Ile Ala Ala Asp Arg Tyr Ile
    130                 135                 140
```

```
Ser Ile Phe Tyr Ala Leu Arg Tyr His Ser Ile Val Thr Leu Pro Arg
145                 150                 155                 160

Ala Arg Arg Ala Val Ala Ala Ile Trp Val Ala Ser Val Val Phe Ser
                165                 170                 175

Thr Leu Phe Ile Ala Tyr Tyr Asp His Val Ala Val Leu Leu Cys Leu
            180                 185                 190

Val Val Phe Phe Leu Ala Met Leu Val Leu Met Ala Val Leu Tyr Val
        195                 200                 205

His Met Leu Ala Arg Ala Cys Gln His Ala Gln Gly Ile Ala Arg Leu
210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Leu Cys Trp Gly Pro
                245                 250                 255

Phe Phe Leu His Leu Thr Leu Ile Val Leu Cys Pro Glu His Pro Thr
                260                 265                 270

Cys Gly Cys Ile Phe Lys Asn Phe Asn Leu Phe Leu Ala Leu Ile Ile
            275                 280                 285

Cys Asn Ala Ile Ile Asp Pro Leu Ile Tyr Ala Phe His Ser Gln Glu
290                 295                 300

Leu Arg Arg Thr Leu Lys Glu Val Leu Thr Cys Ser Cys Ser Gln Asp
305                 310                 315                 320

Arg Ala Leu Val Ser Trp Asp Val Lys Ser Leu Gly Ser Val Cys
                325                 330                 335

Gln Glu Leu Leu Pro Gln Gln Pro Gln Glu Lys Gly Leu Cys Asp Gln
            340                 345                 350

Lys Ala Ser Ser Thr Ala Leu Gln Arg Leu Leu Gln Lys Glu Val Lys
            355                 360                 365

Ser Leu Pro Gln Ala Lys Gly Pro Gly Leu Gln Glu Pro Pro
            370                 375                 380
```

<210> SEQ ID NO 18
<211> LENGTH: 1540
<212> TYPE: DNA
<213> ORGANISM: Homo sapien
<220> FEATURE:
<221> NAME/KEY: misc_feature
<222> LOCATION: (1104)...(1104)
<223> OTHER INFORMATION: n = unknown

<400> SEQUENCE: 18

```
atggctgtgc agggatccca gagaagactt ctgggctccc tcaactccac ccccacagcc      60
atcccccagc tggggctggc tgccaaccag acaggagccc ggtgcctgga ggtgtccatc     120
tctgacgggc tcttcctcag cctggggctg gtgagcttgg tggagaacgc gctggtggtg     180
gccaccatcg ccaagaaccg gaacctgcac tcacccatgt actgcttcat ctgctgcctg     240
gccttgtcgg acctgctggt gagcgggagc aacgtgctgg agacggccgt catcctcctg     300
ctggaggccg gtgcactggt ggcccgggct gcggtgctgc agcagctgga caatgtcatt     360
gacgtgatca cctgcagctc catgctgtcc agcctctgct tcctgggcgc atcgccgtg      420 gaccgctaca tctccatctt ctacgcactg cgctaccaca gcatcgtgac cctgcgcgg      480 gcgcggcgag ccgttgcggc cctctgggtg gccagtgtcg tcttcagcac gctcttcatc     540
gcctactacg accacgtggc cgtcctgctg tgcctcgtgg tcttcttcct ggctatgctg     600
gtgctcatgg ccgtgctgta cgtccacatg ctggcccggg cctgccagca cgcccagggc     660
```

-continued

```
atcgcccggc tccacaagag gcagcgcccg gtccaccagg gctttggcct taaaggcgct    720
gtcaccccca ccatcctgct gggcattttc ttcctctgct ggggccccct cttcctgcat    780
ctcacactca tcgtcctctg ccccgagcac cccacgtgcg gctgcatctt caagaacttc    840
aacctctttc tcgccctcat catctgcaat gccttcatcg acccctcat ctacgccttc     900
cacagccagg agctccgcag gacgctcaag gaggtgctga catgctcctg catgctcctg    960
gtgagcgcgg tgcacgcggc tttaagtgtg ctgggcagag ggaggtggtg atattgtgtg   1020
gtctggttcc tgtgtgaccc tgggcagttc cttacctccc tggtcccccgt ttgtcaaaga   1080
ggatggacta aatgatctct gaangtgttg aagcgcggac ccttctgggt ccagggaggg    1140
gtccctgcaa aactccaggc aggacttctc accagcagtc gtggggaacg gaggaggaca    1200
tggggaggtt gtggggcctc aggctccggg caccaggggc caacctcagg ctcctaaaga    1260
gacattttcc gcccactcct gggacactcc gtctgctcca atgactgagc agcatccacc    1320
ccacccatc tttgctgcca gctctcagga ccgtgccctc gtcagctggg atgtgaagtc    1380
tctgggtgga agtgtgtgcc aagagctact cccacagcag ccccaggaga aggggctttg    1440
tgaccagaaa gcttcatcca cagccttgca gcggctcctg caaaaggagg tgaaatccct    1500
gcctcaggcc aagggaccag gtttgcagga gccccctag                           1540
```

<210> SEQ ID NO 19
<211> LENGTH: 1149
<212> TYPE: DNA
<213> ORGANISM: Homo sapien

<400> SEQUENCE: 19

```
atggctgtgc agggatccca gagaagactt ctgggctccc tcaactccac ccccacagcc    60
atccccagc tggggctggc tgccaaccag acaggagccc ggtgcctgga ggtgtccatc    120
tctgacgggc tcttcctcag cctggggctg gtgagcttgg tggagaacgc gctggtggtg    180
gccaccatcg ccaagaaccg gaacctgcac tcacccatgt actgcttcat ctgctgcctg    240
gccttgtcgg acctgctggt gagcgggagc aacgtgctgg agacggccgt catcctcctg    300
ctggaggccg gtgcactggt ggcccgggct gcggtgctgc agcagctgga caatgtcatt    360
gacgtgatca cctgcagctc catgctgtcc agctctgct tcctgggcgc catcgccgtg    420
gaccgctaca tctccatctt ctacgcactg cgctaccaca gcatcgtgac cctgccgcgg    480
gcgcggcgag ccgttgcggc cctctgggtg gccagtgtcg tcttcagcac gctcttcatc    540
gcctactacg accacgtggc cgtcctgctg tgcctcgtgg tcttcttcct ggctatgctg    600
gtgctcatgg ccgtgctgta cgtccacatg ctggcccggg cctgccagca cgcccagggc    660
atcgcccggc tccacaagag gcagcgcccg gtccaccagg gctttggcct taaaggcgct    720
gtcaccccca ccatcctgct gggcattttc ttcctctgct ggggccccct cttcctgcat    780
ctcacactca tcgtcctctg ccccgagcac cccacgtgcg gctgcatctt caagaacttc    840
aacctctttc tcgccctcat catctgcaat gccttcatcg acccctcat ctacgccttc     900
cacagccagg agctccgcag gacgctcaag gaggtgctga catgctcctg ctctcaggac    960
cgtgccctcg tcagctggga tgtgaagtct ctggtggaa gtgtgtgcca agagctactc    1020
ccacagcagc cccaggagaa ggggctttgt gaccagaaag cttcatccac agccttgcag   1080
cggctcctgc aaaaggaggt gaaatccctg cctcaggcca agggaccagg tttgcaggag   1140
ccccctag                                                              1149
```

-continued

```
<210> SEQ ID NO 20
<211> LENGTH: 382
<212> TYPE: PRT
<213> ORGANISM: Homo sapien

<400> SEQUENCE: 20

Met Ala Val Gln Gly Ser Gln Arg Arg Leu Leu Gly Ser Leu Asn Ser
 1               5                  10                  15

Thr Pro Thr Ala Ile Pro Gln Leu Gly Leu Ala Ala Asn Gln Thr Gly
            20                  25                  30

Ala Arg Cys Leu Glu Val Ser Ile Ser Asp Gly Leu Phe Leu Ser Leu
        35                  40                  45

Gly Leu Val Ser Leu Val Glu Asn Ala Leu Val Val Ala Thr Ile Ala
50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Ser Asn Val Leu Glu Thr Ala
                85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
        115                 120                 125

Leu Ser Ser Leu Cys Phe Leu Gly Ala Ile Ala Val Asp Arg Tyr Ile
130                 135                 140

Ser Ile Phe Tyr Ala Leu Arg Tyr His Ser Ile Val Thr Leu Pro Arg
145                 150                 155                 160

Ala Arg Gln Ala Val Ala Ala Ile Trp Val Ala Ser Val Val Phe Ser
                165                 170                 175

Thr Leu Phe Ile Ala Tyr Tyr Asp His Val Ala Val Leu Leu Cys Leu
            180                 185                 190

Val Val Phe Phe Leu Ala Met Leu Val Leu Met Ala Val Leu Tyr Val
        195                 200                 205

His Met Leu Ala Arg Ala Cys Gln His Ala Gln Gly Ile Ala Arg Leu
    210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
            260                 265                 270

Cys Gly Cys Ile Phe Lys Asn Phe Asn Leu Phe Leu Ala Leu Ile Ile
        275                 280                 285

Cys Asn Ala Ile Ile Asp Pro Leu Ile Tyr Ala Phe His Ser Gln Glu
290                 295                 300

Leu Arg Arg Thr Leu Lys Glu Val Leu Thr Cys Ser Arg Ser Gln Asp
305                 310                 315                 320

Arg Ala Leu Val Ser Trp Asp Val Lys Ser Leu Gly Gly Ser Val Cys
                325                 330                 335

Gln Glu Leu Leu Pro Gln Gln Pro Gln Glu Lys Gly Leu Cys Asp Gln
            340                 345                 350

Lys Ala Ser Ser Thr Ala Leu Gln Arg Leu Leu Gln Lys Glu Val Lys
        355                 360                 365

Ser Leu Pro Gln Ala Lys Gly Pro Gly Leu Gln Glu Pro Pro
370                 375                 380
```

<210> SEQ ID NO 21
<211> LENGTH: 1530
<212> TYPE: DNA
<213> ORGANISM: Homo sapien
<220> FEATURE:
<221> NAME/KEY: misc_feature
<222> LOCATION: (1094)...(1094)
<223> OTHER INFORMATION: n = unknown

<400> SEQUENCE: 21

| | | | | | |
|---|---|---|---|---|---|
| atggctgtgc | agggatccca | gagaagactt | ctgggctccc | tcaactccac | ccccacagcc | 60 |
| atcccccagc | tggggctggc | tgccaaccag | acaggagccc | ggtgcctgga | ggtgtccatc | 120 |
| tctgacgggc | tcttcctcag | cctggggctg | gtgagcttgg | tggagaacgc | gctggtggtg | 180 |
| gccaccatcg | ccaagaaccg | gaacctgcac | tcacccatgt | actgcttcat | ctgctgcctg | 240 |
| gccttgtcgg | acctgctggt | gagcgggagc | aacgtgctgg | agacggccgt | catcctcctg | 300 |
| ctggaggccg | gtgcactggt | ggcccgggct | gcggtgctgc | agcagctgga | caatgtcatt | 360 |
| gacgtgatca | cctgcagctc | catgctgtcc | agcctctgct | tcctgggcgc | catcgccgtg | 420 |
| gaccgctaca | tctccatctt | ctacgcactg | cgctaccaca | gcatcgtgac | cctgccgcgg | 480 |
| gcgcggcgag | ccgttgcggc | cctctgggtg | gccagtgtcg | tcttcagcac | gctcttcatc | 540 |
| gcctactacg | accacgtggc | cgtcctgctg | tgcctcgtgt | tcttcttcct | ggctatgctg | 600 |
| gtgctcatgg | ccgtgctgta | cgtccacatg | ctggcccggg | cctgcagca | cgcccagggc | 660 |
| atcgcccggc | tccacaagag | gcagcgcccg | gtccaccagg | gctttggcct | taaaggcgct | 720 |
| gtcaccccca | ccatcctgct | gggcattttc | ttcctctgct | ggggcccctt | cttcctgcat | 780 |
| ctcacactca | tcgtcctctg | ccccgagcac | cccacgtgcg | gctgcatctt | caagaacttc | 840 |
| aacctctttc | tcgccctcat | catctgcaat | gccttcatcg | accccctcat | ctacgccttc | 900 |
| cacagccagg | agctccgcag | gacgctcaag | gaggtgctga | catgctcctg | gtgagcgcgg | 960 |
| tgcacgcggc | tttaagtgtg | ctgggcagag | ggaggtggtg | atattgtgtg | gtctggttcc | 1020 |
| tgtgtgaccc | tgggcagttc | cttacctccc | tggtccccgt | ttgtcaaaga | ggatggacta | 1080 |
| aatgatctct | gaangtgttg | aagcgcggac | ccttctgggt | ccagggaggg | gtccctgcaa | 1140 |
| aactccaggc | aggacttctc | accagcagtc | gtggggaacg | gaggaggaca | tggggaggtt | 1200 |
| gtggggcctc | aggctccggg | caccaggggc | caacctcagg | ctcctaaaga | gacatttttcc | 1260 |
| gcccactcct | gggacactcc | gtctgctcca | atgactgagc | agcatccacc | ccaccccatc | 1320 |
| tttgctgcca | gctctcagga | ccgtgccctc | gtcagctggg | atgtgaagtc | tctgggtgga | 1380 |
| agtgtgtgcc | aagagctact | cccacagcag | cccaggaga | aggggcttttg | tgaccagaaa | 1440 |
| gcttcatcca | cagccttgca | gcggctcctg | caaaaggagg | tgaaatccct | gcctcaggcc | 1500 |
| aagggaccag | gtttgcagga | gccccctag | | | | 1530 |

<210> SEQ ID NO 22
<211> LENGTH: 1149
<212> TYPE: DNA
<213> ORGANISM: Homo sapien

<400> SEQUENCE: 22

| | | | | | |
|---|---|---|---|---|---|
| atggctgtgc | agggatccca | gagaagactt | ctgggctccc | tcaactccac | ccccacagcc | 60 |
| atcccccagc | tggggctggc | tgccaaccag | acaggagccc | ggtgcctgga | ggtgtccatc | 120 |
| tctgacgggc | tcttcctcag | cctggggctg | gtgagcttgg | tggagaacgc | gctggtggtg | 180 |

-continued

```
gccaccatcg ccaagaaccg gaacctgcac tcacccatgt actgcttcat ctgctgcctg    240
gccttgtcgg acctgctggt gagcgggagc aacgtgctgg agacggccgt catcctcctg    300
ctggaggccg gtgcactggt ggcccgggct gcggtgctgc agcagctgga caatgtcatt    360
gacgtgatca cctgcagctc catgctgtcc agcctctgct tcctgggcgc catcgccgtg    420
gaccgctaca tctccatctt ctacgcactg cgctaccaca gcatcgtgac cctgccgcgg    480
gcgcggcgag ccgttgcggc cctctgggtg gccagtgtcg tcttcagcac gctcttcatc    540
gcctactacg accacgtggc cgtcctgctg tgcctcgtgg tcttcttcct ggctatgctg    600
gtgctcatgg ccgtgctgta cgtccacatg ctggcccggg cctgccagca cgcccagggc    660
atcgcccggc tccacaagag gcagcgcccg gtccaccagg gctttggcct taaaggcgct    720 gtcacccca ccatcctgct gggcattttc ttcctctgct ggggccccctt cttcctgcat    780 ctcacactca tcgtcctctg ccccgagcac cccacgtgcg gctgcatctt caagaacttc    840
aacctctttc tcgccctcat catctgcaat gccttcatcg accccctcat ctacgccttc    900
cacagccagg agctccgcag gacgctcaag gaggtgctga catgctcctg ctctcaggac    960
cgtgccctcg tcagctggga tgtgaagtct ctgggtggaa gtgtgtgcca agagctactc   1020
ccacagcagc cccaggagaa ggggctttgt gaccagaaag cttcatccac agccttgcag   1080
cggctcctgc aaaaggaggt gaaatccctg cctcaggcca aggaccaggt tttgcaggag   1140
ccccccctag                                                         1149
```

<210> SEQ ID NO 23
<211> LENGTH: 382
<212> TYPE: PRT
<213> ORGANISM: Homo sapien

<400> SEQUENCE: 23

```
Met Ala Val Gln Gly Ser Gln Arg Arg Leu Leu Gly Ser Leu Asn Ser
  1               5                  10                  15

Thr Pro Thr Ala Ile Pro Gln Leu Gly Leu Ala Ala Asn Gln Thr Gly
             20                  25                  30

Ala Arg Cys Leu Glu Val Ser Ile Ser Asp Gly Leu Phe Leu Ser Leu
         35                  40                  45

Gly Leu Val Ser Leu Val Glu Asn Ala Leu Val Val Ala Thr Ile Ala
     50                  55                  60

Lys Asn Arg Asn Leu His Ser Pro Met Tyr Cys Phe Ile Cys Cys Leu
 65                  70                  75                  80

Ala Leu Ser Asp Leu Leu Val Ser Gly Ser Asn Val Leu Glu Thr Ala
                 85                  90                  95

Val Ile Leu Leu Leu Glu Ala Gly Ala Leu Val Ala Arg Ala Ala Val
                100                 105                 110

Leu Gln Gln Leu Asp Asn Val Ile Asp Val Ile Thr Cys Ser Ser Met
            115                 120                 125

Leu Ser Ser Leu Cys Phe Leu Gly Ala Ile Ala Val Asp Arg Tyr Ile
        130                 135                 140

Ser Ile Phe Tyr Ala Leu Arg Tyr His Ser Ile Val Thr Leu Pro Arg
145                 150                 155                 160

Ala Arg Arg Ala Val Ala Ala Leu Trp Val Ala Ser Val Val Phe Ser
                165                 170                 175

Thr Leu Phe Ile Ala Tyr Tyr Asp His Val Ala Val Leu Leu Cys Leu
            180                 185                 190

Val Val Phe Phe Leu Ala Met Leu Val Leu Met Ala Val Leu Tyr Val
```

```
                195                 200                 205
His Met Leu Ala Arg Ala Cys Gln His Ala Gln Gly Ile Ala Arg Leu
    210                 215                 220

His Lys Arg Gln Arg Pro Val His Gln Gly Phe Gly Leu Lys Gly Ala
225                 230                 235                 240

Val Thr Pro Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
            260                 265                 270

Cys Gly Cys Ile Phe Lys Asn Phe Asn Leu Phe Leu Ala Leu Ile Ile
        275                 280                 285

Cys Asn Ala Phe Ile Asp Pro Leu Ile Tyr Ala Phe His Ser Gln Glu
    290                 295                 300

Leu Arg Arg Thr Leu Lys Glu Val Leu Thr Cys Ser Cys Ser Gln Asp
305                 310                 315                 320

Arg Ala Leu Val Ser Trp Asp Val Lys Ser Leu Gly Gly Ser Val Cys
                325                 330                 335

Gln Glu Leu Leu Pro Gln Pro Gln Glu Lys Gly Leu Cys Asp Gln
            340                 345                 350

Lys Ala Ser Ser Thr Ala Leu Gln Arg Leu Leu Gln Lys Glu Val Lys
        355                 360                 365

Ser Leu Pro Gln Ala Lys Gly Pro Gly Leu Gln Glu Pro Pro
    370                 375                 380

<210> SEQ ID NO 24
<211> LENGTH: 1540
<212> TYPE: DNA
<213> ORGANISM: Homo sapien
<220> FEATURE:
<221> NAME/KEY: misc_feature
<222> LOCATION: (1104)...(1104)
<223> OTHER INFORMATION: n = unknown

<400> SEQUENCE: 24
atggctgtgc agggatccca gagaagactt ctgggctccc tcaactccac ccccacagcc    60
atcccccagc tggggctggc tgccaaccag acaggagccc ggtgcctgga ggtgtccatc   120
tctgacgggc tcttcctcag cctggggctg gtgagcttgg tggagaacgc gctggtggtg   180
gccaccatcg ccaagaaccg gaacctgcac tcacccatgt actgcttcat ctgctgcctg   240
gccttgtcgg acctgctggt gagcgggagc aacgtgctgg agacggccgt catcctcctg   300
ctggaggccg gtgcactggt ggcccgggct gcggtgctgc agcagctgga caatgtcatt   360
gacgtgatca cctgcagctc catgctgtcc agcctctgct tcctgggcgc cgtcgccgtg   420
gaccgctaca tctccatctt ctacgcactg cgctaccaca gcatcgtgac cctgccgcgg   480
gcgcggcaag ccgttgcggc catctgggtg gccagtgtcg tcttcagcac gctcttcatc   540
gcctactacg accacgtggc cgtcctgctg tgcctcgtgg tcttcttcct ggctatgctg   600
gtgctcatgg ccgtgctgta cgtccacatg ctggcccggg cctgccagca cgcccagggc   660
atcgcccggc tccacaagag gcagcgcccg gtccaccagg gctttggcct taaggcgct   720 gtcaccctca ccatcctgct gggcattttc ttcctctgct ggggcccctt cttcctgcat   780
ctcacactca tcgtcctctg ccccgagcac cccacgtgcg gctgcatctt caagaacttc   840
aacctctttc tcgccccat catctgcaac gccatcatcg accccctcat ctacgccttc   900
cacagccagg agctccgcag gacgctcaag gaggtactga catgctcctg catgctcctg   960
```

-continued

```
gtgagcgcgg tgcacgcggc tttaagtgtg ctgggcagag ggaggtggtg atattgtgtg    1020
gtctggttcc tgtgtgaccc tgggcagttc cttacctccc tggtcccgt tgtcaaaga      1080 ggatggacta atgatctct gaangtgttg aagcgcggac ccttctgggt ccagggaggg     1140
gtccctgcaa aactccaggc aggacttctc accagcagtc gtgggaacg gaggaggaca     1200 tggggaggtt gtggggcctc aggctccggg caccaggggc caacctcagg ctcctaaaga    1260
gacattttcc gcccactcct gggacactcc gtctgctcca atgactgagc agcatccacc   1320 ccacccatc tttgctgcca gctctcagga ccgtgccctc gtcagctggg atgtgaagtc    1380
tctgggtgga agtgtgtgcc aagagctact cccacagcag ccccaggaga aggggcttg    1440 tgaccagaaa gcttcatcca cagccttgca gcggctcctg caaaaggagg tgaaatccct    1500
gcctcaggcc aagggaccag gtttgcagga gccccctag                           1540

<210> SEQ ID NO 25
<211> LENGTH: 1149
<212> TYPE: DNA
<213> ORGANISM: Homo sapien

<400> SEQUENCE: 25
atggctgtgc agggatccca gagaagactt ctgggctccc tcaactccac ccccacagcc     60 atccccagc tggggctggc tgccaaccag acaggagccc ggtgcctgga ggtgtccatc     120
tctgacgggc tcttcctcag cctggggctg gtgagcttgg tggagaacgc gctggtggtg    180
gccaccatcg ccaagaaccg gaacctgcac tcacccatgt actgcttcat ctgctgcctg    240
gccttgtcgg acctgctggt gagcgggagc aacgtgctgg agacggccgt catcctcctg    300
ctggaggccg tgcactggt ggcccgggct gcggtgctgc agcagctgga caatgtcatt    360
gacgtgatca cctgcagctc catgctgtcc agcctctgct tcctgggcgc cgtcgccgtg   420
gaccgctaca tctccatctt ctacgcactg cgctaccaca gcatcgtgac cctgccgcgg    480
gcgcggcaag ccgttgcggc catctgggtg gccagtgtcg tcttcagcac gctcttcatc   540
gcctactacg accacgtggc cgtcctgctg tgcctcgtgg tcttcttcct ggctatgctg    600
gtgctcatgg ccgtgctgta cgtccacatg ctggcccggg cctgccagca cgcccagggc    660
atcgcccggc tccacaagag gcagcgcccg gtccaccagg gctttggcct taaaggcgct    720
gtcaccctca ccatcctgct gggcattttc ttcctctgct ggggccccct cttcctgcat    780
ctcacactca tcgtcctctg ccccgagcac cccacgtgcg gctgcatctt caagaacttc    840 aacctcttc tcgcccccat catctgcaac gccatcatcg acccctcat ctacgccttc    900 cacagccagg agctccgcag gacgctcaag gaggtactga catgctcctg ctctcaggac   960
cgtgccctcg tcagctggga tgtgaagtct ctgggtggaa gtgtgtgcca agagctactc   1020
ccacagcagc cccaggagaa ggggctttgt gaccagaaag cttcatccac agccttgcag   1080
cggctcctgc aaaaggaggt gaaatccctg cctcaggcca agggaccagg tttgcaggag   1140
ccccctag                                                             1149

<210> SEQ ID NO 26
<211> LENGTH: 382
<212> TYPE: PRT
<213> ORGANISM: Homo sapien

<400> SEQUENCE: 26

Met Ala Val Gln Gly Ser Gln Arg Arg Leu Leu Gly Ser Leu Asn Ser
 1               5                  10                  15
```

-continued

```
Thr Pro Thr Ala Ile Pro Gln Leu Gly Leu Ala Ala Asn Gln Thr Gly
             20                  25                  30

Ala Arg Cys Leu Glu Val Ser Ile Ser Asp Gly Leu Phe Leu Ser Leu
         35                  40                  45

Gly Leu Val Ser Leu Val Glu Asn Ala Leu Val Val Ala Thr Ile Ala
     50                  55                  60

Lys Asn Arg Asn Leu His Ser Pro Met Tyr Cys Phe Ile Cys Cys Leu
 65                  70                  75                  80

Ala Leu Ser Asp Leu Leu Val Ser Gly Ser Asn Val Leu Glu Thr Ala
                 85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
        115                 120                 125

Leu Ser Ser Leu Cys Phe Leu Gly Ala Val Ala Val Asp Arg Tyr Ile
    130                 135                 140

Ser Ile Phe Tyr Ala Leu Arg Tyr His Ser Ile Val Thr Leu Pro Arg
145                 150                 155                 160

Ala Arg Gln Ala Val Ala Ala Ile Trp Val Ala Ser Val Val Phe Ser
                165                 170                 175

Thr Leu Phe Ile Ala Tyr Tyr Asp His Val Ala Val Leu Leu Cys Leu
            180                 185                 190

Val Val Phe Phe Leu Ala Met Leu Val Leu Met Ala Val Leu Tyr Val
        195                 200                 205

His Met Leu Ala Arg Ala Cys Gln His Ala Gln Gly Ile Ala Arg Leu
    210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
            260                 265                 270

Cys Gly Cys Ile Phe Lys Asn Phe Asn Leu Phe Leu Ala Pro Ile Ile
        275                 280                 285

Cys Asn Ala Ile Ile Asp Pro Leu Ile Tyr Ala Phe His Ser Gln Glu
    290                 295                 300

Leu Arg Arg Thr Leu Lys Glu Val Leu Thr Cys Ser Cys Ser Gln Asp
305                 310                 315                 320

Arg Ala Leu Val Ser Trp Asp Val Lys Ser Leu Gly Gly Ser Val Cys
                325                 330                 335

Gln Glu Leu Leu Pro Gln Gln Pro Gln Glu Lys Gly Leu Cys Asp Gln
            340                 345                 350

Lys Ala Ser Ser Thr Ala Leu Gln Arg Leu Leu Gln Lys Glu Val Lys
        355                 360                 365

Ser Leu Pro Gln Ala Lys Gly Pro Gly Leu Gln Glu Pro Pro
    370                 375                 380

<210> SEQ ID NO 27
<211> LENGTH: 65
<212> TYPE: PRT
<213> ORGANISM: Homo sapien

<400> SEQUENCE: 27

Ser Gln Asp Arg Ala Leu Val Ser Trp Asp Val Lys Ser Leu Gly Gly
  1               5                  10                  15
```

Ser Val Cys Gln Glu Leu Leu Pro Gln Gln Pro Gln Glu Lys Gly Leu
              20                  25                  30

Cys Asp Gln Lys Ala Ser Ser Thr Ala Leu Gln Arg Leu Leu Gln Lys
         35                  40                  45

Glu Val Lys Ser Leu Pro Gln Ala Lys Gly Pro Gly Leu Gln Glu Pro
     50                  55                  60

Pro
65

<210> SEQ ID NO 28
<211> LENGTH: 632
<212> TYPE: DNA
<213> ORGANISM: Homo sapien
<220> FEATURE:
<221> NAME/KEY: misc_feature
<222> LOCATION: (604)...(604)
<223> OTHER INFORMATION: n = unknown
<221> NAME/KEY: misc_feature
<222> LOCATION: (613)...(613)
<223> OTHER INFORMATION: n = unknown
<221> NAME/KEY: misc_feature
<222> LOCATION: (626)...(626)
<223> OTHER INFORMATION: n = unknown

<400> SEQUENCE: 28
tttttgatgc tgagtcacat ttattaccag actttcctgg ccccatgctc acaggcactg      60
gtcactgagt caggcatttg cacgggctgt ctgcttgggc gactgctgca ggaaagcagg     120
ctgaggccca gtgcccagtc tgagccttag aaccggccct caggagggtc cagcctcaca     180
ccactagggg ggctcctgca aacctggtcc cttggcctga ggaggattt cacctccttt      240 tgcaggagcc gctgcaaggc tgttggatga agctttctgg tcacaaagcc ccttctcctg     300
gggctgctgt gggagtagct cttggcacac acttccaccc agagacttca catcccagct     360
gacgagggca cggtcctgag agcaggagca cgtcagcacc tccttgagcg tcctgcgacg     420
tcctggctgt ggaaggcgta gatgaggggg tcgatgatgg cattgcagat gatgagggcg     480
agaaagaggt tgaaagttct tgaagatgca gccgacgtgg ggtgctcggg gcagaggacg     540
atgagtgtga gatgcaggaa gaggggggccc cagcagagga gaaattgcca acaggattgg     600
tganggtgaa gcngctttta agccanagcc ct                                   632

<210> SEQ ID NO 29
<211> LENGTH: 551
<212> TYPE: DNA
<213> ORGANISM: Homo sapien
<220> FEATURE:
<221> NAME/KEY: misc_feature
<222> LOCATION: (88)...(88)
<223> OTHER INFORMATION: n = unknown
<221> NAME/KEY: misc_feature
<222> LOCATION: (381)...(381)
<223> OTHER INFORMATION: n = unknown
<221> NAME/KEY: misc_feature
<222> LOCATION: (483)...(483)
<223> OTHER INFORMATION: n = unknown

<400> SEQUENCE: 29
aacaaacttt ggtaagtagt gaatggcaaa ggctcagggg gtttgcagca ggacctcctt      60
ggggtcagat ctgccagcct cgggttgnct ttcagacccc tcatcgtcta tgaggcatcc     120
tgtaagtgca gctgtggcca gggcttgcat atgcaatcaa ttcctgattc acctagttct     180
tggcaggaag agaaaatact cgttaatcag aggactaaac aatccaaaag cgcattctct     240

-continued

```
ctctgggaat ggaatataat ttatatttct gttgctattg aattatcctt ctaattccac      300
tggactaaac ttaataccag taatactaaa attttgtttt gggcaaagcg acttgaagga      360
ggagtcagtg gcgcactaat ngctgactgt gaaaaataaa cacctctgag atcaagaatc      420
ccacagtgag agctaggatt tgaaggtatc cagagattgc aaaactctgt gactaacagc      480 aanttttttaa ccagggcaaa ccaaaccact cctacttgga cttaaacctc aatcatttag    540
atttcattcc c                                                           551

<210> SEQ ID NO 30
<211> LENGTH: 355
<212> TYPE: DNA
<213> ORGANISM: Homo sapien

<400> SEQUENCE: 30
aaatgatctc tgaaagtgtt gaagcgcgga cccttctggg tcccggaggg gtccctgcaa       60
aactccaggc aggacttctc accagcagtc gtggggaacc gaggaggaca tggggaggtt      120
gtggggcctc aggctccggg caccaggggc caacctcagg ctcctaaaga gacattttcc      180
gcccacatcc tgggacactc cgtctgctcc aatgactgag cagcatccac cccacccat      240 ctttgctgcc agctctcagg accgtgcgct cgtcagctgg gatgtgaagt ctctgggtgg      300
aagtgtgtgc aagagctac tctcacagca gccccaggag aagggctttt gtgac            355

<210> SEQ ID NO 31
<211> LENGTH: 263
<212> TYPE: DNA
<213> ORGANISM: Homo sapien

<400> SEQUENCE: 31
cgggtgatgc tgagtcacat ttattaccag actttcctgg ccccatgctc acaggcactg       60
gtcactgagt caggcatttg ccagggctgt ctgcttgggc gactgctgca tgaaagcagg      120
ctgaggcccc agtgcccagt ctgagcctta gaaccggccc tcaggagggc tcagccctat     180
accactaggg gggctcctgc aaacctggtc ccttggcctg aggcagggat ttcacctcct     240
tttgcaggag ccgctgcaag gct                                              263

<210> SEQ ID NO 32
<211> LENGTH: 24
<212> TYPE: DNA
<213> ORGANISM: Artificial Sequence
<220> FEATURE:
<223> OTHER INFORMATION: oligonucleotide

<400> SEQUENCE: 32
tctcacactc atcgtcctct gccc                                              24

<210> SEQ ID NO 33
<211> LENGTH: 24
<212> TYPE: DNA
<213> ORGANISM: Artificial Sequence
<220> FEATURE:
<223> OTHER INFORMATION: oligonucleotide

<400> SEQUENCE: 33
catcgcctac tacgaccacg tggc                                              24

<210> SEQ ID NO 34
<211> LENGTH: 24
<212> TYPE: DNA
<213> ORGANISM: Artificial Sequence
```

```
<220> FEATURE:
<223> OTHER INFORMATION: oligonucleotide

<400> SEQUENCE: 34
cgctgcaagg ctgttggatg aagc                                              24

<210> SEQ ID NO 35
<211> LENGTH: 24
<212> TYPE: DNA
<213> ORGANISM: Artificial Sequence
<220> FEATURE:
<223> OTHER INFORMATION: oligonucleotide

<400> SEQUENCE: 35
gtgggagtag ctcttggcac acac                                              24

<210> SEQ ID NO 36
<211> LENGTH: 41
<212> TYPE: DNA
<213> ORGANISM: Artificial Sequence
<220> FEATURE:
<223> OTHER INFORMATION: oligonucleotide

<400> SEQUENCE: 36
gggcccgaat cgccgccat ggctgtgcag ggatcccaga g                            41

<210> SEQ ID NO 37
<211> LENGTH: 40
<212> TYPE: DNA
<213> ORGANISM: Artificial Sequence
<220> FEATURE:
<223> OTHER INFORMATION: oligonucleotide

<400> SEQUENCE: 37
ggcacggtcc tgagagcagg agcatgtcag cacctccttg                             40

<210> SEQ ID NO 38
<211> LENGTH: 39
<212> TYPE: DNA
<213> ORGANISM: Artificial Sequence
<220> FEATURE:
<223> OTHER INFORMATION: oligonucleotide

<400> SEQUENCE: 38
ctgacatgct cctgctctca ggaccgtgcc ctcgtcagc                              39

<210> SEQ ID NO 39
<211> LENGTH: 38
<212> TYPE: DNA
<213> ORGANISM: Artificial Sequence
<220> FEATURE:
<223> OTHER INFORMATION: oligonucleotide

<400> SEQUENCE: 39
agtttagcgg ccgcctaggg gggctcctgc aaacctgg                               38

<210> SEQ ID NO 40
<211> LENGTH: 42
<212> TYPE: DNA
<213> ORGANISM: Artificial Sequence
<220> FEATURE:
<223> OTHER INFORMATION: oligonucleotide

<400> SEQUENCE: 40
gatcgaattc gccgccatgg ctgtgcaggg atcccagaga ag                          42
```

<210> SEQ ID NO 41
<211> LENGTH: 33
<212> TYPE: DNA
<213> ORGANISM: Artificial Sequence
<220> FEATURE:
<223> OTHER INFORMATION: oligonucleotide

<400> SEQUENCE: 41
gatcgaattc ctagggggc tcctgcaaac ctg                33

<210> SEQ ID NO 42
<211> LENGTH: 35
<212> TYPE: DNA
<213> ORGANISM: Artificial Sequence
<220> FEATURE:
<223> OTHER INFORMATION: oligonucleotide

<400> SEQUENCE: 42
gatcgaattc gtgcccagtc tgagccttag aaccg             35

<210> SEQ ID NO 43
<211> LENGTH: 317
<212> TYPE: PRT
<213> ORGANISM: Homo sapien

<400> SEQUENCE: 43

Met Ala Val Gln Gly Ser Gln Arg Arg Leu Leu Gly Ser Leu Asn Ser
 1               5                  10                  15

Thr Pro Thr Ala Ile Pro Gln Leu Gly Leu Ala Ala Asn Gln Thr Gly
            20                  25                  30

Ala Arg Cys Leu Glu Val Ser Ile Ser Asp Gly Leu Phe Leu Ser Leu
        35                  40                  45

Gly Leu Val Ser Leu Val Glu Asn Ala Leu Val Val Ala Thr Ile Ala
    50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Thr Asn Val Leu Glu Thr Ala
                85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
        115                 120                 125

Leu Ser Ser Leu Cys Phe Leu Gly Ala Ile Ala Val Asp Arg Tyr Ile
    130                 135                 140

Ser Ile Phe Tyr Ala Leu Arg Tyr His Ser Ile Val Thr Leu Pro Arg
145                 150                 155                 160

Ala Pro Arg Ala Val Ala Ala Ile Trp Val Ala Ser Val Val Phe Ser
                165                 170                 175

Thr Leu Phe Ile Ala Tyr Tyr Asp His Val Ala Val Leu Leu Cys Leu
            180                 185                 190

Val Val Phe Phe Leu Ala Met Leu Val Leu Met Ala Val Leu Tyr Val
        195                 200                 205

His Met Leu Ala Arg Ala Cys Gln His Ala Gln Gly Ile Ala Arg Leu
    210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
            260                 265                 270

Cys Gly Cys Ile Phe Lys Asn Phe Asn Leu Phe Leu Ala Leu Ile Ile
            275                 280                 285

Cys Asn Ala Ile Ile Asp Pro Leu Ile Tyr Ala Phe His Ser Gln Glu
            290                 295                 300

Leu Arg Arg Thr Leu Lys Glu Val Leu Thr Cys Ser Trp
305                 310                 315

<210> SEQ ID NO 44
<211> LENGTH: 317
<212> TYPE: PRT
<213> ORGANISM: Homo sapien

<400> SEQUENCE: 44

Met Ala Val Gln Gly Ser Gln Arg Arg Leu Leu Gly Ser Leu Asn Ser
1                   5                   10                  15

Thr Pro Thr Ala Ile Pro Gln Leu Gly Leu Ala Ala Asn Gln Thr Gly
            20                  25                  30

Ala Arg Cys Leu Glu Val Ser Ile Ser Asp Gly Leu Phe Leu Ser Leu
            35                  40                  45

Gly Leu Val Ser Leu Val Glu Asn Ala Leu Val Val Ala Thr Ile Ala
    50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Ser Asn Val Leu Glu Thr Ala
                85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
            115                 120                 125

Leu Ser Ser Leu Cys Phe Leu Gly Ala Ile Ala Val Asp Arg Tyr Ile
    130                 135                 140

Ser Ile Phe Tyr Ala Leu Arg Tyr His Ser Ile Val Thr Leu Pro Arg
145                 150                 155                 160

Ala Arg Gln Ala Val Ala Ala Ile Trp Val Ala Ser Val Val Phe Ser
            165                 170                 175

Thr Leu Phe Ile Ala Tyr Tyr Asp His Val Ala Val Leu Leu Cys Leu
            180                 185                 190

Val Val Phe Phe Leu Ala Met Leu Val Leu Met Ala Val Leu Tyr Val
            195                 200                 205

His Met Leu Ala Arg Ala Cys Gln His Ala Gln Gly Ile Ala Arg Leu
    210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
            245                 250                 255

Phe Phe Leu His Leu Thr Leu Ile Val Leu Cys Pro Glu His Pro Thr
            260                 265                 270

Cys Gly Cys Ile Phe Lys Asn Phe Asn Leu Phe Leu Ala Leu Ile Ile
            275                 280                 285

Cys Asn Ala Ile Ile Asp Pro Leu Ile Tyr Ala Phe His Ser Gln Glu
            290                 295                 300

Leu Arg Arg Thr Leu Lys Glu Val Leu Thr Cys Ser Trp

<210> SEQ ID NO 45
<211> LENGTH: 962
<212> TYPE: DNA
<213> ORGANISM: Homo sapien

<400> SEQUENCE: 45

```
atggctgtgc agggatccca gagaagactt ctgggctccc tcaactccac ccccacagcc      60
atcccccagc tggggctggc tgccaaccag acaggagccc ggtgcctgga ggtgtccatc     120
tctgacgggc tcttcctcag cctggggctg gtgagcttgg tggagaacgc gctggtggtg     180
gccaccatcg ccaagaaccg gaacctgcac tcacccatgt actgcttcat ctgctgcctg     240
gccttgtcgg acctgctggt gagcgggagc aacgtgctgg agacggccgt catcctcctg     300
ctggaggccg gtgcactggt ggcccgggct gcggtgctgc agcagctgga caatgtcatt     360
gacgtgatca cctgcagctc catgctgtcc agcctctgct cctgggcgc catcgccgtg      420
gaccgctaca tctccatctt ctacgcactg cgctaccaca gcatcgtgac cctgccgcgg     480
gcgcggcgag ccgttgcggc cctctgggtg gccagtgtcg tcttcagcac gctcttcatc     540
gcctactacg accacgtggc cgtcctgctg tgcctcgtgg tcttcttcct ggctatgctg     600
gtgctcatgg ccgtgctgta cgtccacatg ctggcccggg cctgccagca cgcccagggc     660
atcgcccggc tccacaagag gcagcgcccg gtccaccagg gctttggcct taaaggcgct     720
gtcacccca ccatcctgct gggcatttc ttcctctgct ggggccctt cttcctgcat        780
ctcacactca tcgtcctctg ccccgagcac cccacgtgcg gctgcatctt caagaacttc     840
aacctctttc tcgccctcat catctgcaat gccttcatcg accccctcat ctacgccttc     900
cacagccagg agctccgcag gacgctcaag gaggtgctga catgctcctg gtagcttggt     960
ga                                                                    962
```

<210> SEQ ID NO 46
<211> LENGTH: 297
<212> TYPE: PRT
<213> ORGANISM: Homo sapien

<400> SEQUENCE: 46

Met Ala Val Gln Gly Ser Gln Arg Arg Leu Leu Gly Ser Leu Asn Ser
1               5                   10                  15

Thr Pro Thr Ala Ile Pro Gln Leu Gly Leu Ala Ala Asn Gln Thr Gly
            20                  25                  30

Ala Arg Cys Leu Glu Val Ser Ile Ala Thr Ile Ala Lys Asn Arg Asn
        35                  40                  45

Leu His Ser Pro Met Tyr Cys Phe Ile Cys Cys Leu Ala Leu Ser Asp
    50                  55                  60

Leu Leu Val Ser Gly Ser Asn Val Leu Glu Thr Ala Val Ile Leu Leu
65                  70                  75                  80

Leu Glu Ala Gly Ala Leu Val Ala Arg Ala Ala Val Leu Gln Gln Leu
                85                  90                  95

Asp Asn Val Ile Asp Val Ile Thr Cys Ser Ser Met Leu Ser Ser Leu
            100                 105                 110

Cys Phe Leu Gly Ala Ile Ala Val Asp Arg Tyr Ile Ser Ile Phe Tyr
        115                 120                 125

Ala Leu Arg Tyr His Ser Ile Val Thr Leu Pro Arg Ala Arg Arg Ala
    130                 135                 140

-continued

```
Val Ala Ala Leu Trp Val Ala Ser Val Val Phe Ser Thr Leu Phe Ile
145                 150                 155                 160

Ala Tyr Tyr Asp His Val Ala Val Leu Leu Cys Leu Val Val Phe Phe
            165                 170                 175

Leu Ala Met Leu Val Leu Met Ala Val Leu Tyr Val His Met Leu Ala
            180                 185                 190

Arg Ala Cys Gln His Ala Gln Gly Ile Ala Arg Leu His Lys Arg Gln
        195                 200                 205

Arg Pro Val His Gln Gly Phe Gly Leu Lys Gly Ala Val Thr Pro Thr
    210                 215                 220

Ile Leu Leu Gly Ile Phe Phe Leu Cys Trp Gly Pro Phe Phe Leu His
225                 230                 235                 240

Leu Thr Leu Ile Val Leu Cys Pro Glu His Pro Thr Cys Gly Cys Ile
                245                 250                 255

Phe Lys Asn Phe Asn Leu Phe Leu Ala Leu Ile Ile Cys Asn Ala Phe
            260                 265                 270

Ile Asp Pro Leu Ile Tyr Ala Phe His Ser Gln Glu Leu Arg Arg Thr
        275                 280                 285

Leu Lys Glu Val Leu Thr Cys Ser Trp
    290                 295
```